US010927346B2

(12) United States Patent
Valamehr et al.

(10) Patent No.: US 10,927,346 B2
(45) Date of Patent: Feb. 23, 2021

(54) ENHANCED IMMUNE EFFECTOR CELLS AND USE THEREOF

(71) Applicant: Fate Therapeutics, Inc., San Diego, CA (US)

(72) Inventors: Bahram Valamehr, San Diego, CA (US); Ryan Bjordahl, San Diego, CA (US); Jode Goodridge, San Diego, CA (US); Tom Tong Lee, San Diego, CA (US)

(73) Assignee: FATE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/576,411

(22) Filed: Sep. 19, 2019

(65) Prior Publication Data

US 2020/0069734 A1 Mar. 5, 2020

Related U.S. Application Data

(63) Continuation of application No. PCT/US2018/067289, filed on Dec. 21, 2018.

(60) Provisional application No. 62/774,052, filed on Nov. 30, 2018, provisional application No. 62/649,781, filed on Mar. 29, 2018, provisional application No. 62/609,827, filed on Dec. 22, 2017.

(51) Int. Cl.

| | |
|---|---|
| ***C12N 5/0783*** | (2010.01) |
| ***A61K 35/17*** | (2015.01) |
| ***A61K 45/06*** | (2006.01) |
| ***C12N 5/074*** | (2010.01) |
| ***C12N 15/90*** | (2006.01) |
| ***C12N 15/85*** | (2006.01) |
| ***C12N 5/0789*** | (2010.01) |

(52) U.S. Cl.

CPC ............ *C12N 5/0646* (2013.01); *A61K 35/17* (2013.01); *A61K 45/06* (2013.01); *C12N 5/0636* (2013.01); *C12N 5/0647* (2013.01); *C12N 5/0696* (2013.01); *C12N 15/85* (2013.01); *C12N 15/907* (2013.01); *C12N 2310/20* (2017.05); *C12N 2506/45* (2013.01); *C12N 2800/80* (2013.01)

(58) Field of Classification Search

CPC ............ C12N 15/0646; C12N 15/0636; C12N 15/0647; C12N 15/907; C12N 15/85; C12N 2510/00; C12N 2506/45; A61K 35/17

See application file for complete search history.

(56) References Cited

U.S. PATENT DOCUMENTS

| | | | |
|---|---|---|---|
| 6,140,081 A | 10/2000 | Barbas | |
| 6,352,694 B1 | 3/2002 | June et al. | |
| 6,453,242 B1 | 9/2002 | Eisenberg et al. | |
| 6,534,261 B1 | 3/2003 | Cox, III et al. | |
| 7,888,121 B2 | 2/2011 | Urnov et al. | |
| 7,972,854 B2 | 7/2011 | Miller et al. | |
| 8,409,577 B2 | 4/2013 | Thompson et al. | |
| 9,447,194 B2 | 9/2016 | Jensen | |
| 9,587,020 B2 | 3/2017 | Wu et al. | |
| 2004/0101519 A1 | 5/2004 | June et al. | |
| 2006/0034810 A1 | 2/2006 | Riley et al. | |
| 2009/0191164 A1 | 7/2009 | Majeti et al. | |
| 2010/0267145 A1 | 10/2010 | Mihara | |
| 2011/0145940 A1 | 6/2011 | Voytas et al. | |
| 2014/0134142 A1 | 5/2014 | Smith et al. | |
| 2014/0219975 A1 | 8/2014 | June et al. | |
| 2014/0221319 A1* | 8/2014 | Sinclair | A61K 31/353 514/150 |
| 2015/0140665 A1 | 5/2015 | Calos et al. | |
| 2016/0046700 A1 | 2/2016 | Foster et al. | |
| 2016/0058857 A1 | 3/2016 | Spencer et al. | |
| 2017/0073643 A1 | 3/2017 | Valamehr et al. | |
| 2017/0166877 A1 | 6/2017 | Bayle et al. | |
| 2017/0183407 A1 | 6/2017 | Cooper et al. | |
| 2018/0236053 A1* | 8/2018 | Dusseaux | C07K 16/2896 |

FOREIGN PATENT DOCUMENTS

| | | |
|---|---|---|
| WO | WO-98/53058 A1 | 11/1998 |
| WO | WO-98/53059 A1 | 11/1998 |
| WO | WO-98/53060 A1 | 11/1998 |
| WO | WO-02/016536 A1 | 2/2002 |
| WO | WO-03/016496 A2 | 2/2003 |
| WO | WO-03/016496 A3 | 2/2003 |
| WO | WO-2011/159726 A2 | 12/2011 |
| WO | WO-2011/159726 A3 | 12/2011 |
| WO | WO-2014/165707 A2 | 10/2014 |
| WO | WO-2014/165707 A3 | 10/2014 |
| WO | WO-2015/148926 A1 | 10/2015 |
| WO | WO-2015/148926 A9 | 10/2015 |

(Continued)

OTHER PUBLICATIONS

Kumar et al. World J Stem Cell 7(2):315-328, 2015 (Year: 2015).*
Lu et al. Reprod Dom Anim 47(suppl. 4):72-76,2012 (Year: 2012).*
Cockayne et al. Blood 92(4):1324-1333, 1998 (Year: 1998).*
Casneuf, T. et al. (Oct. 24, 2017). "Effects of daratumumab on natural killer cells and impact on clinical outcomes in relapsed or refractory multiple myeloma," *Blood Adv* 1(23):2105-2114.
Donnelly, M.L. et al. (May 2001). "The 'cleavage' activities of foot-and-mouth disease virus 2A site-directed mutants and naturally occurring '2A-like' sequences," *J Gen Virol* 82(Pt 5):1027-1041.

(Continued)

*Primary Examiner* — Marcia S Noble
(74) *Attorney, Agent, or Firm* — Mintz, Levin, Cohn, Ferris, Glovsky and Popeo, P.C.

(57) ABSTRACT

Provided are methods and compositions for obtaining functionally enhanced derivative effector cells obtained from directed differentiation of genomically engineered iPSCs. The derivative cells provided herein have stable and functional genome editing that delivers improved or enhanced therapeutic effects. Also provided are therapeutic compositions and the used thereof comprising the functionally enhanced derivative effector cells alone, or with antibodies or checkpoint inhibitors in combination therapies.

22 Claims, 15 Drawing Sheets

Specification includes a Sequence Listing.

(56) References Cited

FOREIGN PATENT DOCUMENTS

| | | | |
|---|---|---|---|
| WO | WO-2016/205711 | A1 | 12/2016 |
| WO | WO-2017/078807 | A1 | 5/2017 |
| WO | WO-2017/078807 | A9 | 5/2017 |
| WO | WO-2017/079673 | A1 | 5/2017 |
| WO | WO-2019/075057 | A1 | 4/2019 |
| WO | WO-2019/126748 | A1 | 6/2019 |

OTHER PUBLICATIONS

Fate Therapeutics (Nov. 10, 2018). "Programmed Cellular Immunotherapies: Natural Killer Cell Franchise Update," located at <https://fatetherapeutics.com/wp-content/uploads/2018/12/SITC-NK100-FINAL.pdf> pp. 1-58.

Fate Therapeutics (Oct. 2018). "Programmed Cellular Immunotherapies: Corporate Overview," located at <https://fatetherapeutics.com/wp-content/uploads/2018/10/FATE-Investor-Presentation-20181001.pdf> pp. 1-44.

International Search Report dated Apr. 23, 2019, for PCT Application No. PCT/US2018/067289, 8 pages.

Hedge, M. et al. (Aug. 1, 2016, e-published Jul. 18, 2016). "Tandem CAR T cells targeting HER2 and IL13Rα2 mitigate tumor antigen escape," *J Clin Invest* 126(8):3036-3052.

Ryan, M.D. et al. (Nov. 1991). "Cleavage of foot-and-mouth disease virus polyprotein is mediated by residues located within a 19 amino acid sequence," *J Gen Virol* 72(Pt 11)2727-2732.

Written Opinion dated Apr. 23, 2019, for PCT Application No. PCT/US2018/067289, 11 pages.

* cited by examiner

ENHANCED IMMUNE EFFECTOR CELLS AND USE THEREOF

RELATED APPLICATION

This application claims priority to U.S. Provisional Application Ser. No. 62/609,827, filed Dec. 22, 2017, U.S. Provisional Application Ser. No. 62/649,781, filed Mar. 29, 2018, and U.S. Provisional Application Ser. No. 62/774,052, filed Nov. 30, 2018, the disclosures of which are hereby incorporated by reference in their entirety.

SEQUENCE LISTING

The material in the accompanying Sequence Listing is hereby incorporated by reference in its entirety. The accompanying Sequence Listing file, named "1505926146_1_13601-196-228_ST25", was created on Sep. 18, 2019 and is 35,625 bytes in size.

FIELD OF THE INVENTION

The present disclosure is broadly concerned with the field of off-the-shelf immunocellular products. More particularly, the present disclosure is concerned with the strategies for developing multifunctional effector cells capable of delivering therapeutically relevant properties in vivo. The cell products developed under the present disclosure address critical limitations of patient-sourced cell therapies.

BACKGROUND OF THE INVENTION

The field of adoptive cell therapy is currently focused on using patient- and donor-sourced cells, which makes it particularly difficult to achieve consistent manufacturing of cancer immunotherapies and to deliver therapies to all patients who may benefit. There is also the need to improve the efficacy and persistence of adoptively transferred lymphocytes to promote favorable patient outcome. Lymphocytes such as T cells and natural killer (NK) cells are potent anti-tumor effectors that play an important role in innate and adaptive immunity. However, the use of these immune cells for adoptive cell therapies remain to be challenging and have unmet needs for improvement. Therefore, there are significant opportunities remain to harness the full potential of T and NK cells, or other lymphocytes in adoptive immunotherapy.

SUMMARY OF THE INVENTION

There is a need for functionally improved effector cells that address issues ranging from response rate, cell exhaustion, loss of transfused cells (survival and/or persistence), tumor escape through target loss or lineage switch, tumor targeting precision, off-target toxicity, off-tumor effect, to efficacy against solid tumors, i.e., tumor microenvironment and related immune suppression, recruiting, trafficking and infiltration.

It is an object of the present invention to provide methods and compositions to generate derivative non-pluripotent cells differentiated from a single cell derived iPSC (induced pluripotent stem cell) clonal line, which iPSC line comprises one or several genetic modifications in its genome. Said one or several genetic modifications include DNA insertion, deletion, and substitution, and which modifications are retained and remain functional in subsequently derived cells after differentiation, expansion, passaging and/or transplantation.

The iPSC derived non-pluripotent cells of the present application include, but not limited to, CD34 cells, hemogenic endothelium cells, HSCs (hematopoietic stem and progenitor cells), hematopoietic multipotent progenitor cells, T cell progenitors, NK cell progenitors, T cells, NKT cells, NK cells, and B cells. The iPSC derived non-pluripotent cells of the present application comprise one or several genetic modifications in their genome through differentiation from an iPSC comprising the same genetic modifications. The engineered clonal iPSC differentiation strategy for obtaining genetically engineered derivative cells requires that the developmental potential of the iPSC in a directed differentiation is not adversely impacted by the engineered modality in the iPSC, and also that the engineered modality functions as intended in the derivative cell. Further, this strategy overcomes the present barrier in engineering primary lymphocytes, such as T cells or NK cells obtained from peripheral blood, as such cells are difficult to engineer, with engineering of such cells often lacking reproducibility and uniformity, resulting in cells exhibiting poor cell persistence with high cell death and low cell expansion. Moreover, this strategy avoids production of a heterogenous effector cell population otherwise obtained using primary cell sources which are heterogenous to start with.

Some aspects of the present invention provide genome-engineered iPSCs obtained using a method comprising (I), (II) or (III), reflecting a strategy of genomic engineering subsequently to, simultaneously with, and prior to the reprogramming process, respectively:

(I): genetically engineering iPSCs by one or both of (i) and (ii), in any order: (i) introducing into iPSCs one or more construct(s) to allow targeted integration at selected site(s); (ii) (a) introducing into iPSCs one or more double stranded break(s) at selected site(s) using one or more endonuclease capable of selected site recognition; and (b) culturing the iPSCs of step (I)(ii)(a) to allow endogenous DNA repair to generate targeted in/dels at the selected site(s); thereby obtaining genome-engineered iPSCs capable of differentiation into partially or fully differentiated cells.

(II): genetically engineering reprogramming non-pluripotent cells to obtain the genome-engineered iPSCs comprising: (i) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate reprogramming of the non-pluripotent cells; and (ii) introducing into the reprogramming non-pluripotent cells of step (II)(i) one or both of (a) and (b), in any order: (a) one or more construct(s) to allow targeted integration at selected site(s); (b) one or more double stranded break(s) at a selected site using at least one endonuclease capable of selected site recognition, then the cells of step (II)(ii)(b) are cultured to allow endogenous DNA repair to generate targeted in/dels at the selected site(s); as such the obtained genome-engineered iPSCs comprise at least one functional targeted genomic editing, and said genome-engineered iPSCs are capable of differentiation into partially or fully differentiated cells.

(III): genetically engineering non-pluripotent cells for reprogramming to obtain genome-engineered iPSCs comprising (i) and (ii): (i) introducing into non-pluripotent cells one or both of (a) and (b), in any order: (a) one or more construct(s) to allow targeted integration at selected site(s); (b) one or more double stranded break(s) at a selected site using at least one endonuclease capable of selected site recognition, wherein the cells of step (III)(i)(b) are cultured to allow endogenous DNA repair to generate targeted in/dels at the selected sites; and (ii) contacting the cells of step (III)(i) with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted editing at selected sites; thereby obtaining genome-engineered iPSCs comprising at least one functional targeted genomic editing, and said genome-engineered iPSCs are capable of being differentiated into partially differentiated cells or fully-differentiated cells.

In one embodiment of the above method, the at least one targeted genomic editing at one or more selected sites comprises insertion of one or more exogenous polynucleotides encoding safety switch proteins, targeting modalities, receptors, signaling molecules, transcription factors, pharmaceutically active proteins and peptides, drug target candidates, or proteins promoting engraftment, trafficking, homing, viability, self-renewal, persistence, and/or survival of the genome-engineered iPSCs or derivative cells thereof. In some embodiments, the exogenous polynucleotides for insertion are operatively linked to (1) one or more exogenous promoters comprising CMV, EF1α, PGK, CAG, UBC, or other constitutive, inducible, temporal-, tissue-, or cell type-specific promoters; or (2) one or more endogenous promoters comprised in the selected sites comprising AAVS1, CCR5, ROSA26, collagen, HTRP, H11, beta-2 microglobulin, GAPDH, TCR or RUNX1, or other locus meeting the criteria of a genome safe harbor. In some embodiments, the genome-engineered iPSCs generated using the above method comprise one or more different exogenous polynucleotides encoding protein comprising caspase, thymidine kinase, cytosine deaminase, modified EGFR, or B-cell CD20, wherein when the genome-engineered iPSCs comprise two or more suicide genes, the suicide genes are integrated in different safe harbor locus comprising AAVS1, CCR5, ROSA26, collagen, HTRP, H11, H11, beta-2 microglobulin, GAPDH, TCR or RUNX1. In one embodiment, the exogenous polynucleotide encodes a partial or full peptide of IL2, IL4, IL6, IL7, IL9, IL10, IL11, IL12, IL15, IL18, IL21, and/or respective receptors thereof. In some embodiments, the partial or full peptide of IL2, IL4, IL6, IL7, IL9, IL10, IL11, IL12, IL15, IL18, IL21, and/or respective receptors thereof encoded by the exogenous polynucleotide is in a form of fusion protein.

In some other embodiments, the genome-engineered iPSCs generated using the method provided herein comprise in/del at one or more endogenous genes associated with targeting modality, receptors, signaling molecules, transcription factors, drug target candidates, immune response regulation and modulation, or proteins suppressing engraftment, trafficking, homing, viability, self-renewal, persistence, and/or survival of the iPSCs or derivative cells thereof. In some embodiments, the endogenous gene for disruption comprises at least one of B2M, TAP1, TAP2, Tapasin, NLRC5, PD1, LAGS, TIM3, RFXANK, CIITA, RFX5, RFXAP, and any gene in the chromosome 6p21 region.

In yet some other embodiments, the genome-engineered iPSCs generated using the method provided herein comprise a caspase encoding exogenous polynucleotide at AAVS1 locus, and a thymidine kinase encoding exogenous polynucleotide at H11 locus.

In still some other embodiments, approach (I), (II) and/or (III) further comprises: contacting the genome-engineered iPSCs with a small molecule composition comprising a MEK inhibitor, a GSK3 inhibitor and a ROCK inhibitor, to maintain the pluripotency of the genomic-engineered iPSCs. In one embodiments, the obtained genome engineered iPSCs comprising at least one targeted genomic editing are functional, are differentiation potent, and are capable of differentiating into non-pluripotent cells comprising the same functional genomic editing.

The present invention also provides the followings.

One aspect of the present application provides a cell or a population thereof, wherein the cell is an induced pluripotent cell (iPSC), a clonal iPSC, or an iPS cell line cell, or a derivative cell obtained from differentiating any of the above said iPSC; and wherein any of the above said cell comprises at least a CD38 knockout or a polynucleotide encoding an IL15/IL15Rα fusion protein without an intracellular domain (IL15Δ). In some embodiments of the obtained derivative cell from iPSC differentiation, the derivative cell is a hematopoietic cell, including, but not limited to, CD34 cells, hemogenic endothelium cells, HSCs (hematopoietic stem and progenitor cells), hematopoietic multipotent progenitor cells, T cell progenitors, NK cell progenitors, T cells, NKT cells, NK cells, and B cells; which hematopoietic cell (i.e., derivative CD34 cell, derivative hemogenic endothelium cells derivative hematopoietic stem and progenitor cell, derivative hematopoietic multipotent progenitor cell, derivative T cell progenitor, derivative NK cell progenitor, derivative T cell, derivative NKT cell, derivative NK cell, or derivative B cell) comprises longer telomeres in comparison to its native counterpart cell obtained from peripheral blood, umbilical cord blood, or any other donor tissues.

In some embodiments of said iPSC and its derivative cell comprising a CD38 knockout or a polynucleotide encoding an IL15/IL15Rα fusion protein without an intracellular domain (IL15Δ), the cell further comprises one or more of the following genomic editing: (i) B2M null or low; (ii) CIITA null or low; (iii) introduced expression of HLA-G or non-cleavable HLA-G; (iv) a high affinity non-cleavable CD16 (hnCD16) or a variant thereof; (v) a chimeric antigen receptor (CAR), (vi) a partial or full peptide of a cell surface expressed exogenous cytokine or a receptor thereof; (vii) at least one of the genotypes listed in Table 1; (viii) deletion or reduced expression in at least one of TAP1, TAP2, Tapasin, NLRC5, PD1, LAG3, TIM3, RFXANK, CIITA, RFX5, RFXAP, and any gene in the chromosome 6p21 region; and (ix) introduced or increased expression in at least one of HLA-E, 41BBL, CD3ζ, CD4, CD8, CD16, CD47, CD113, CD131, CD137, CD80, PDL1, $A_{2A}R$, CAR, TCR, Fc receptor, an engager, and a surface triggering receptor for coupling with bi- or multi-specific or universal engager.

In some embodiments of said iPSC and its derivative cell comprising at least a CD38 knockout or a polynucleotide encoding an IL15/IL15Rα fusion protein without an intracellular domain (IL15Δ), and optional additional genomic editing as described above and throughout this application, the cell may comprise (i) one or more exogenous polynucleotides integrated in one safe harbor locus; or (ii) more than two exogenous polynucleotides integrated in different safe harbor loci; or (iii) a polynucleotide encoding an IL15Δ comprising an amino acid sequence of at least 75%, 80%, 85%, 90%, 95% or 99% identity to SEQ ID NOs: 17, 19 or 21. In some embodiments, the safe harbor locus comprises at least one of AAVS1, CCR5, ROSA26, collagen, HTRP, H11, beta-2 microglobulin, GAPDH, TCR or RUNX1. In one particular embodiment, the safe harbor locus TCR is a constant region of TCR alpha.

In some embodiments of the cell or population thereof, the cell comprising at least a CD38 knockout or an IL15Δ, and one or more of the additional genomic editing above is a derivative NK or a derivative T cell, and the derivative NK or a derivative T cell has at least one of the following characteristics including, but not limited to: (i) improved persistency and/or survival; (ii) increased resistance to native immune cells; (iii) increased cytotoxicity; (iv) improved tumor penetration; (v) enhanced or acquired ADCC; (vi) enhanced ability in migrating, and/or activating or recruiting bystander immune cells, to tumor sites; (vii) enhanced ability to reduce tumor immunosuppression; (viii) improved ability in rescuing tumor antigen escape; and (ix) reduced fratricide, when compared to its native counterpart NK or T cell obtained from peripheral blood, umbilical cord blood, or any other donor tissues.

In one embodiment of the cell or population thereof, the cell comprising a CD38 knockout or an IL15Δ further comprises a high affinity non-cleavable CD16 (hnCD16) or a variant thereof. Some embodiments of the high affinity non-cleavable CD16 (hnCD16) or a variant thereof comprises at least any one of the followings: (a) F176V and S197P in ectodomain domain of CD16; (b) a full or partial ectodomain originated from CD64; (c) a non-native (or non-CD16) transmembrane domain; (d) a non-native (or non-CD16) intracellular domain; (e) a non-native (or non-CD16) signaling domain; (f) a non-native stimulatory domain; and (g) transmembrane, signaling, and stimulatory domains that are not originated from CD16, and are originated from a same or different polypeptide. In some embodiments, the non-native transmembrane domain is derived from CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor (TCR) polypeptide. In some embodiments, the non-native stimulatory domain is derived from CD27, CD28, 4-1BB, OX40, ICOS, PD-1, LAG-3, 2B4, BTLA, DAP10, DAP12, CTLA-4, or NKG2D polypeptide. In some other embodiments, the non-native signaling domain is derived from CD3ζ, 2B4, DAP10, DAP12, DNAM1, CD137 (41BB), IL21, IL7, IL12, IL15, NKp30, NKp44, NKp46, NKG2C, or NKG2D polypeptide. In some particular embodiments of a hnCD16 variant, the non-native transmembrane domain is derived from NKG2D, the non-native stimulatory domain is derived from 2B4, and the non-native signaling domain is derived from CD3ζ.

In one embodiment of the cell or population thereof, the cell comprising a CD38 knockout or an IL15Δ further comprises a chimeric antigen receptor (CAR), and wherein the CAR could be any one or more of the followings: (i) T cell specific or NK cell specific; (ii) bi-specific antigen binding CAR; (iii) a switchable CAR; (iv) a dimerized CAR; (v) a split CAR; (vi) a multi-chain CAR; (vii) an inducible CAR; (viii) co-expressed with another CAR; (ix) co-expressed with a partial or full peptide of a cell surface expressed exogenous cytokine or a receptor thereof, optionally in separate constructs or in a bi-cistronic construct; (xi) co-expressed with a checkpoint inhibitor, optionally in separate constructs or in a bi-cistronic construct; (xii) is specific to CD19 or BCMA; and/or (xiii) is specific to any one of ADGRE2, carbonic anhydrase IX (CA1X), CCRI, CCR4, carcinoembryonic antigen (CEA), CD3ζ, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein2 (EGP 2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBCI, TRBC2, vascular endothelial growth factor R2 (VEGF-R2), Wilms tumor protein (WT-1), and a pathogen antigen.

In some of the embodiments, in which a checkpoint inhibitor is co-expressed with a CAR, the checkpoint inhibitor is an antagonist to one or more checkpoint molecules comprising PD-1, PDL-1, TIM-3, TIGIT, LAG-3, CTLA-4, 2B4, 4-1BB, 4-1BBL, A2aR, BATE, BTLA, CD39, CD47, CD73, CD94, CD96, CD160, CD200, CD200R, CD274, CEACAM1, CSF-1R, Foxp1, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR. The checkpoint inhibitor co-expressed with the CAR could be an antibody, or humanized or Fc modified variants or fragments and functional equivalents and biosimilars thereof, specific to any of the above checkpoint molecules. In some embodiments, the CAR of any one of (i) to (ix) may be inserted at TRAC locus. In some embodiments, the CAR of any one of (i) to (ix) inserted at TRAC locus may be driven by an endogenous promoter of TCR. In some embodiments, the insertion of the CAR of any one of (i) to (ix) at TRAC locus leads TCR knockout.

In one embodiment of the cell or population thereof, the cell comprising a CD38 knockout further comprises a partial or full peptide of a cell surface expressed exogenous cytokine or a receptor thereof, and wherein the exogenous cytokine or a receptor thereof may comprise at least one of IL2, IL4, IL6, IL7, IL9, IL10, IL11, IL12, IL15, IL18, IL21, and respective receptor thereof; or may comprise at least one of: (i) co-expression of IL15 and IL15Rα by using a self-cleaving peptide; (ii) a fusion protein of IL15 and IL15Rα; (iii) an IL15/IL15Rα fusion protein with intracellular domain of IL15Rα truncated; (iv) a fusion protein of IL15 and membrane bound Sushi domain of IL15Rα; (v) a fusion protein of IL15 and IL15Rβ; (vi) a fusion protein of IL15 and common receptor γC, wherein the common receptor γC is native or modified; and (vii) a homodimer of IL15Rβ; wherein any one of (i)-(vii) can be co-expressed with a CAR in separate constructs or in a bi-cistronic construct. In some embodiments, the partial or full peptide of a cell surface exogenous cytokine or a receptor is transiently expressed in the cell provided herein.

In another embodiment of the cell or population thereof, the cell comprises a partial or full peptide of a cell surface expressed exogenous cytokine or a receptor, wherein the cytokine may comprise at least one of IL2, IL4, IL6, IL7, IL9, IL10, IL11, IL12, IL15, IL18, IL21, and respective receptor thereof. In an embodiment of the cell or population thereof comprising IL15 cytokine or receptor, the cell may comprise at least one of: (i) co-expression of IL15 and IL15Rα by using a self-cleaving peptide; (ii) a fusion protein of IL15 and IL15Rα; (iii) an IL15/IL15Rα fusion protein with intracellular domain of IL15Rα truncated; (iv) a fusion protein of IL15 and membrane bound Sushi domain of IL15Rα; (v) a fusion protein of IL15 and IL15Rβ; (vi) a fusion protein of IL15 and common receptor γC, wherein the common receptor γC is native or modified; and (vii) a homodimer of IL15Rβ; wherein any one of (i)-(vii) can be co-expressed with a CAR in separate constructs or in a bi-cistronic construct. In some embodiments, the partial or full peptide of a cell surface exogenous cytokine or a receptor is transiently expressed in the cell provided herein. In one embodiment, the cell or population thereof comprises a polynucleotide encoding an IL15Δ comprising an amino acid sequence of at least 75%, 80%, 85%, 90%, 95% or 99% identity to SEQ ID NOs: 17, 19 or 21. In one embodiment of the cell or population thereof, the cell comprising an IL15Δ may further comprise one or more of B2M null or low; CIITA null or low; introduced expression of HLA-G or non-cleavable HLA-G; a high affinity non-cleavable CD16 (hnCD16) or a variant thereof; a chimeric antigen receptor (CAR), a partial or full peptide of a cell surface expressed exogenous cytokine or a receptor thereof, wherein the cytokine is not IL15; at least one of the genotypes listed in Table 1; deletion or reduced expression in at least one of TAP1, TAP2, Tapasin, NLRC5, PD1, LAG3, TIM3, RFXANK, CIITA, RFX5, RFXAP, and any gene in the chromosome 6p21 region; and introduced or increased expression in at least one of HLA-E, 41BBL, CD3ζ, CD4, CD8, CD16, CD47, CD113, CD131, CD137, CD80, PDL1, $A_{2A}$R, CAR, TCR, Fc receptor, an engager, and surface triggering receptor for coupling with bi- or multi-specific or universal engagers. In an embodiment of a cell or population thereof comprising both an IL15Δ and a CAR, the IL15Δ can be co-expressed with a CAR in separate constructs or in a bi-cistronic construct.

In one embodiment of the cell or population thereof, the cell comprising a CD38 knockout or an IL15Δ is a derivative NK or a derivative T cell, wherein the derivative NK cell is capable of recruiting, and/or migrating T cells to tumor sites, and wherein the derivative NK or the derivative T cell is capable of reducing tumor immunosuppression in the presence of one or more checkpoint inhibitors. In some embodiments, the checkpoint inhibitors are antagonists to one or more checkpoint molecules comprising PD-1, PDL-1, TIM-3, TIGIT, LAG-3, CTLA-4, 2B4, 4-1BB, 4-1BBL, A2aR, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR. In some other embodiments, the checkpoint inhibitors comprise either (a) one or more of atezolizumab, avelumab, durvalumab, ipilimumab, IPH4102, IPH43, IPH33, lirimumab, monalizumab, nivolumab, pembrolizumab, and their derivatives or functional equivalents; or (b) at least one of atezolizumab, nivolumab, and pembrolizumab.

Another aspect of the present application provides a composition comprising any of the cells or populations thereof as described above, and throughout this application. In some embodiments, the iPSC or iPSC derived cells (derivative cells) may comprise any one of the genotypes listed in Table 1 of this application. In some embodiments, the iPSC or derivative cell therefrom comprises CD38 knockout (CD38−/−). In some embodiments, the iPSC or derivative cell therefrom comprises an IL15Δ. In some embodiments, the iPSC or derivative cell therefrom comprises hnCD16 and CD38 knockout. In some embodiments, the iPSC or derivative cell therefrom comprises hnCD16 and an IL15Δ. In some embodiments, the iPSC or derivative cell therefrom comprises hnCD16, CD38 knockout, and an IL15Δ. In some embodiments, the iPSC or derivative cell therefrom comprises hnCD16, CD38−/−, and a CAR. In some embodiments, the iPSC or derivative cell therefrom comprises hnCD16, IL15Δ, and a CAR. In some embodiments, the iPSC or derivative cell therefrom comprises hnCD16, IL15Δ, CD38−/−, and a CAR. In some embodiments, the iPSC or derivative cell therefrom comprises hnCD16, CD38−/−, a CAR, and a partial or full peptide of a cell surface expressed exogenous cytokine or a receptor thereof as provided above and throughout this application. In some embodiments of cells comprising hnCD16, CD38−/−, and a CAR, the CAR is specific to CD19. In some embodiments of cells comprising hnCD16, IL15Δ, and a CAR, the CAR is specific to CD19. In some embodiments of cells comprising hnCD16, IL15Δ, CD38−/−, and a CAR, the CAR is specific to CD19. In some other embodiments of cells comprising hnCD16, CD38−/−, and a CAR, the CAR is specific to CD269 (BCMA). In some other embodiments of cells comprising hnCD16, IL15Δ, and a CAR, the CAR is specific to CD269 (BCMA). In some other embodiments of cells comprising hnCD16, IL15Δ, CD38−/−, and a CAR, the CAR is specific to CD269 (BCMA). In yet some other embodiments, the CAR is specific to any one of ADGRE2, carbonic anhydrase IX (CA1X), CCRI, CCR4, carcinoembryonic antigen (CEA), CD3ζ, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBCI, TRBC2, vascular endothelial growth factor R2 (VEGF-R2), Wilms tumor protein (WT-1), and various pathogen antigen known in the art.

Accordingly, a further aspect of the present application provides a composition for therapeutic use, which comprises, in addition to any of the derivative cell as provided herein, one or more therapeutic agents. In some embodiments of the composition for therapeutic use, the therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). In some embodiments of the composition for therapeutic use, the checkpoint inhibitor used with the provided cells comprises one or more antagonists checkpoint molecules comprising PD-1, PDL-1, TIM-3, TIGIT, LAG-3, CTLA-4, 2B4, 4-1BB, 4-1BBL, A2aR, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR. In some embodiments of the composition for therapeutic use, the checkpoint inhibitor used with the provided cells comprises one or more of atezolizurnab, avelumab, durvalumab, ipilimumab, IPH4102, IPH43, IPH33, lirimumab, monalizurnab, nivolumab, pembrolizumab, and their derivatives or functional equivalents. In some other embodiments of the composition for therapeutic use, the checkpoint inhibitor used with the provided cells comprises at least one of atezolizumab, nivolumab, and pembrolizumab. In some embodiments of the composition for therapeutic use, the therapeutic agents comprise one or more of venetoclax, azacitidine, and pomalidomide.

In some embodiments of the composition for therapeutic use, the antibody used with the provided cells comprises any one of the anti-CD20, anti-HER2, anti-CD52, anti-EGFR, anti-CD123, anti-GD2, anti-PDL1, and/or anti-CD38 antibody. In some embodiments of the composition for therapeutic use, the antibody used with the provided cells comprises one or more of rituximab, veltuzumab, ofatumumab, ublituximab, ocaratuzumab, obinutuzumab, trastuzumab, pertuzumab, alemtuzumab, certuximab, dinutuximab, avelumab, daratumumab, isatuximab, MOR202, 7G3, CSL362, elotuzumab, and their humanized or Fc modified variants or fragments and their functional equivalents and biosimilars. In still some other embodiments of the composition for therapeutic use, the antibody used with the provided cells comprises daratumumab.

The present application also provides a therapeutic use of the cell or therapeutic composition as described herein by introducing the composition to a subject suitable for adoptive cell therapy. In some embodiments, the subject suitable for and in need of the adoptive cell therapy has an autoimmune disorder; a hematological malignancy; a solid tumor; cancer, or a virus infection.

A further aspect of the present application provides a method of manufacturing the derivative cell as described herein, and the method comprises differentiating an iPSC comprising CD38 knockout or an IL15Δ, and optionally one or more of: (i) B2M null or low; (ii) CIITA null or low; (iii) introduced expression of HLA-G or non-cleavable HLA-G; (iv) a high affinity non-cleavable CD16 (hnCD16) or a variant thereof; (v) a chimeric antigen receptor (CAR); (vi) a partial or full peptide of a cell surface expressed exogenous cytokine or a receptor thereof; and (vii) at least one of the genotypes listed in Table 1; (viii) deletion or reduced expression in at least one of TAP1, TAP2, Tapasin, NLRC5, PD1, LAG3, TIM3, RFXANK, CIITA, RFX5, RFXAP, and any gene in the chromosome 6p21 region; and (ix) introduced or increased expression in at least one of HLA-E, 41BBL, CD3ζ, CD4, CD8, CD16, CD47, CD113, CD131, CD137, CD80, PDL1, $A_{2A}$R, CAR, TCR, Fc receptor, an engager, and surface triggering receptor for coupling with bi- or multi-specific or universal engagers.

In some embodiments of the manufacturing method, the method further comprises genomically engineering a clonal iPSC to knock out CD38 or to knock in an IL15Δ, and optionally to knock out B2M and CIITA, or to introduce expression of HLA-G or non-cleavable HLA-G, a high affinity non-cleavable CD16 or a variant thereof, a CAR, and/or a partial or full peptide of a cell surface expressed exogenous cytokine or a receptor thereof; and the CAR and the partial or full peptide of a cell surface expressed exogenous cytokine or a receptor thereof are co-expressed in separate constructs or in a bi-cistronic construct. In some embodiments of the manufacturing method, the genomic engineering of an iPSC comprises targeted editing. In some embodiments, the targeted editing comprises deletion, insertion, or in/del. In some embodiments, the targeted editing is carried out by CRISPR, ZFN, TALEN, homing nuclease, homology recombination, or any other functional variation of these methods.

The present application further provides CRISPR mediated editing of clonal iPSCs, thereby producing edited clonal iPSCs comprising CD38 knockout or an IL15Δ knockin, or at least one of the genotypes listed in Table 1. In some embodiments of the CRISPR mediated editing, the obtained CD38 knockout is bi-allelic. In some embodiments of the CRISPR mediated editing, the CD38 knockout is a nucleic acid cleavage between a first and a second target sequence, and wherein the targeting sequences comprise SEQ ID NO: 3 and SEQ ID NO: 4, respectively. In some embodiments of the CRISPR mediated editing, the obtained IL15Δ knock-in comprises a polynucleotide encoding an IL15Δ comprising an amino acid sequence of at least 75%, 80%, 85%, 90%, 95% or 99% identity to SEQ ID NOs: 17, 19 or 21. In some embodiments of the CRISPR mediated editing above, the editing further comprises an insertion of a CAR at TRAC locus, and/or wherein the CAR is driven by an endogenous promoter of TCR, and/or wherein the TCR is knocked out by the CAR insertion.

Additional aspects of the present application provide a method of improving anti-CD38 antibody treatment comprising administering to a subject under the treatment effector cells without CD38 expression. In some embodiments of the anti-CD38 antibody treatment, the anti-CD38 antibody may be daratumumab, isatuximab, or MOR202, or any of the humanized or Fc modified variants or fragments, functional equivalents and biosimilars thereof. The effector cells provided for a method of improving anti-CD38 antibody treatment, in some embodiments, comprise derivative hematopoietic cells comprising derivative NK cells or derivative T cells; and the derivative NK cells or derivative T cells comprise a CD38 knockout, a high affinity non-cleavable CD16 or a variant thereof, and optionally comprise (i) B2M and CIITA knockout; (ii) introduced expression of HLA-G or non-cleavable HLA-G, a CAR, and/or a partial or full peptide of a cell surface expressed exogenous cytokine or a receptor thereof wherein the CAR and a partial or full peptide of a cell surface expressed exogenous cytokine or a receptor thereof is co-expressed in separate constructs or in a bi-cistronic construct; and/or (iii) at least one of the genotypes listed in Table 1. In some embodiments of the method improving an anti-CD38 antibody treatment, the method reduces the anti-CD38 antibody induced effector cell reduction in the subject under such treatment.

Still, another aspect of the present application provides a method of reducing or preventing allorejection against allogenic effector cells by using a CD38 specific antagonist, wherein the allogenic effector cells comprise CD38 knockout, and wherein the CD38 specific antagonist is capable of suppressing activated T and B cells in a recipient of the allogenic effector cells. In some embodiments, the CD38 specific antagonist is an anti-CD38 antibody, a CD38 specific engager, or a CD38 chimeric antigen receptor (CAR). In some other embodiment, the anti-CD38 antibody is daratumumab, isatuximab, or MOR202, or any of the humanized or Fc modified variants or fragments, functional equivalents and biosimilars thereof. In yet another embodiment, the anti-CD38 antibody is daratumumab, and the provided method herein confers a novel use of daratumumab.

Various objects and advantages of the compositions and methods as provided herein will become apparent from the following description taken in conjunction with the accompanying drawings wherein are set forth, by way of illustration and example, certain embodiments of this invention.

DETAILED DESCRIPTION OF THE INVENTION

Figure 1:
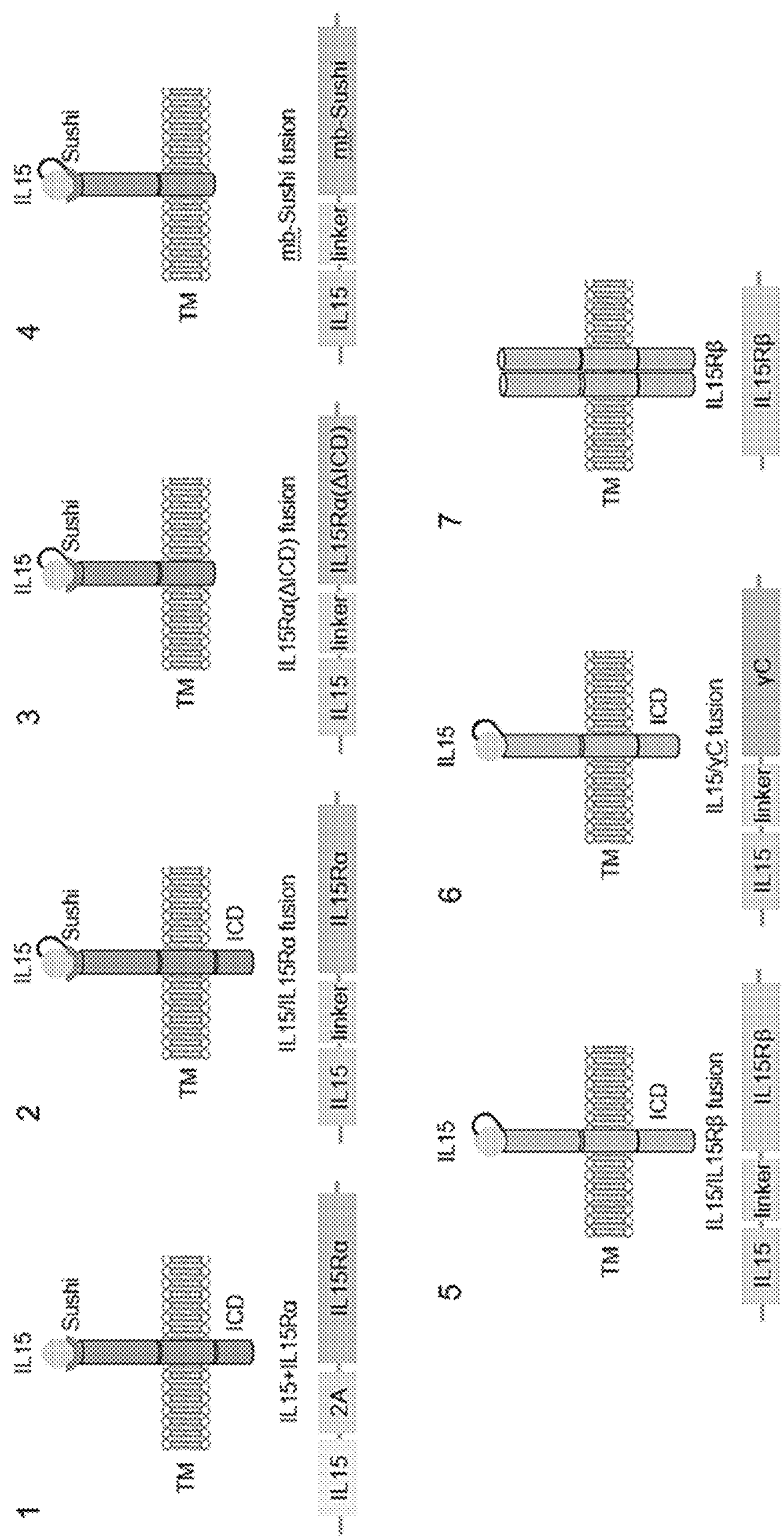
FIG. 1 is a graphic representation of several construct designs for cell surface expressed cytokine in iPSC derived cells. IL15 is used as an illustrative example, which can be replaced with other desirable cytokines.

Genomic modification of iPSCs (induced pluripotent stem cells) includes polynucleotide insertion, deletion and substitution. Exogenous gene expression in genome-engineered iPSCs often encounters problems such as gene silencing or reduced gene expression after prolonged clonal expansion of the original genome-engineered iPSCs, after cell differentiation, and in dedifferentiated cell types from the cells derived from the genome-engineered iPSCs. On the other hand, direct engineering of primary immune cells such as T or NK cells is challenging, and presents a hurdle to the preparation and delivery of engineered immune cells for adoptive cell therapy. The present invention provides an efficient, reliable, and targeted approach for stably integrating one or more exogenous genes, including suicide genes and other functional modalities, which provide improved therapeutic properties relating to engraftment, trafficking, homing, migration, cytotoxicity, viability, maintenance, expansion, longevity, self-renewal, persistence, and/or survival, into iPSC derivative cells, including but not limited to HSCs (hematopoietic stem and progenitor cell), T cell progenitor cells, NK cell progenitor cells, T cells, NKT cells, NK cells.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition functionally inert, but at a low concentration. Similar meaning can be applied to the term "absence of," where referring to the absence of a particular substance or its source thereof of a composition.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, iPSCs, means that the stem cells are produced from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta, i.e., are not totipotent.

As used herein, the term "multipotent stem cell" refers to a cell that has the developmental potential to differentiate into cells of one or more germ layers (ectoderm, mesoderm and endoderm), but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60/81, TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the "primed" or "metastable" state of pluripotency akin to the epiblast stem cells (EpiSC) of the late blastocyst, and the "Naïve" or "Ground" state of pluripotency akin to the inner cell mass of the early/preimplantation blastocyst. While both pluripotent states exhibit the characteristics as described above, the naïve or ground state further exhibits: (i) pre-inactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical inter-cell spacing.

As used herein, the term "subject" refers to any animal, preferably a human patient, livestock, or other domesticated animal.

A "pluripotency factor," or "reprogramming factor," refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate," or "maintain," refers to the sustaining, propagating (growing) and/or differentiating of cells outside of tissue or the body, for example in a sterile plastic (or coated plastic) cell culture dish or flask. "Cultivation," or "maintaining," may utilize a culture medium as a source of nutrients, hormones and/or other factors helpful to propagate and/or sustain the cells.

As used herein, the term "mesoderm" refers to one of the three germinal layers that appears during early embryogenesis and which gives rise to various specialized cell types including blood cells of the circulatory system, muscles, the heart, the dermis, skeleton, and other supportive and connective tissues.

As used herein, the term "definitive hemogenic endothelium" (HE) or "pluripotent stem cell-derived definitive hemogenic endothelium" (iHE) refers to a subset of endothelial cells that give rise to hematopoietic stem and progenitor cells in a process called endothelial-to-hematopoietic transition. The development of hematopoietic cells in the embryo proceeds sequentially from lateral plate mesoderm through the hemangioblast to the definitive hemogenic endothelium and hematopoietic progenitors.

The term "hematopoietic stem and progenitor cells," "hematopoietic stem cells," "hematopoietic progenitor cells," or "hematopoietic precursor cells" refers to cells which are committed to a hematopoietic lineage but are capable of further hematopoietic differentiation and include, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). The term "definitive hematopoietic stem cell" as used herein, refers to CD34+ hematopoietic cells capable of giving rise to both mature myeloid and lymphoid cell types including T cells, NK cells and B cells. Hematopoietic cells also include various subsets of primitive hematopoietic cells that give rise to primitive erythrocytes, megakarocytes and macrophages.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells. A T cell can be any T cell, such as a cultured T cell, e.g., a primary T cell, or a T cell from a cultured T cell line, e.g., Jurkat, SupT1, etc., or a T cell obtained from a mammal. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. Additional types of helper T cells include cells such as Th3 (Treg), Th17, Th9, or Tfh cells. Additional types of memory T cells include cells such as central memory T cells (Tcm cells), effector memory T cells (Tem cells and TEMRA cells). The T cell can also refer to a genetically engineered T cell, such as a T cell modified to express a T cell receptor (TCR) or a chimeric antigen receptor (CAR). The T cell can also be differentiated from a stem cell or progenitor cell.

"CD4+ T cells" refers to a subset of T cells that express CD4 on their surface and are associated with cell-mediated immune response. They are characterized by the secretion profiles following stimulation, which may include secretion of cytokines such as IFN-gamma, TNF-alpha, IL2, IL4 and IL10. "CD4" are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibility complex) class II-restricted immune responses. On T-lymphocytes they define the helper/inducer subset.

"CD8+ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

As used herein, the term "NK cell" or "Natural Killer cell" refer to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3- and CD56+, expressing at least one of NKG2C and CD57, and optionally, CD16, but lack expression of one or more of the following: PLZF, SYK, FceRγ, and EAT-2. In some embodiments, isolated subpopulations of CD56+ NK cells comprise expression of CD16, NKG2C, CD57, NKG2D, NCR ligands, NKp30, NKp40, NKp46, activating and inhibitory KIRs, NKG2A and/or DNAM-1. CD56+ can be dim or bright expression.

As used herein, the term "NKT cells" or "natural killer T cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are recognized. Invariant or type I NKT cells express a very limited TCR repertoire—a canonical α-chain (Vα24-Jα18 in humans) associated with a limited spectrum of β chains (Vβ11 in humans). The second population of NKT cells, called non-classical or non-invariant type II NKT cells, display a more heterogeneous TCR αβ usage. Type I NKT cells are considered suitable for immunotherapy. Adaptive or invariant (type I) NKT cells can be identified with the expression of at least one or more of the following markers, TCR Va24-Ja18, Vb11, CD1d, CD3ζ, CD4, CD8, aGalCer, CD161 and CD56.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, isolated from a tissue or biopsy sample. The term also includes a cell that is removed from at least one, some or all components as the cell is found in non-naturally occurring environments, for example, isolated form a cell culture or cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cell compositions, substantially pure cell compositions and cells cultured in a medium that is non-naturally occurring. Isolated cells may be obtained from separating the desired cells, or populations thereof, from other substances or cells in the environment, or from removing one or more other cell populations or subpopulations from the environment.

As used herein, the term "purify" or the like refers to increasing purity. For example, the purity can be increased to at least 50%, 60%, 70%, 80%, 90%, 95%, 99%, or 100%.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "construct" refers to a macromolecule or complex of molecules comprising a polynucleotide to be delivered to a host cell, either in vitro or in vivo. A "vector," as used herein refers to any nucleic acid construct capable of directing the delivery or transfer of a foreign genetic material to target cells, where it can be replicated and/or expressed. The term "vector" as used herein comprises the construct to be delivered. A vector can be a linear or a circular molecule. A vector can be integrating or non-integrating. The major types of vectors include, but are not limited to, plasmids, episomal vector, viral vectors, cosmids, and artificial chromosomes. Viral vectors include, but are not limited to, adenovirus vector, adeno-associated virus vector, retrovirus vector, lentivirus vector, Sendai virus vector, and the like.

By "integration" it is meant that one or more nucleotides of a construct is stably inserted into the cellular genome, i.e., covalently linked to the nucleic acid sequence within the cell's chromosomal DNA. By "targeted integration" it is meant that the nucleotide(s) of a construct is inserted into the cell's chromosomal or mitochondrial DNA at a pre-selected site or "integration site". The term "integration" as used herein further refers to a process involving insertion of one or more exogenous sequences or nucleotides of the construct, with or without deletion of an endogenous sequence or nucleotide at the integration site. In the case, where there is a deletion at the insertion site, "integration" may further comprise replacement of the endogenous sequence or a nucleotide that is deleted with the one or more inserted nucleotides.

As used herein, the term "exogenous" is intended to mean that the referenced molecule or the referenced activity is introduced into, or non-native to, the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e. a polypeptide found in nature) or fragment thereof; a variant polypeptide (i.e. a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or antisense orientation.

As used herein, the term "genetic imprint" refers to genetic or epigenetic information that contributes to preferential therapeutic attributes in a source cell or an iPSC, and is retainable in the source cell derived iPSCs, and/or the iPSC-derived hematopoietic lineage cells. As used herein, "a source cell" is a non-pluripotent cell that may be used for generating iPSCs through reprogramming, and the source cell derived iPSCs may be further differentiated to specific cell types including any hematopoietic lineage cells. The source cell derived iPSCs, and differentiated cells therefrom are sometimes collectively called "derived" or "derivative" cells depending on the context. For example, derivative effector cells, or derivative NK cells or derivative T cells, as used throughout this application are cells differentiated from an iPSC, as compared to their primary counterpart obtained from natural/native sources such as peripheral blood, umbilical cord blood, or other donor tissues. As used herein, the genetic imprint(s) conferring a preferential therapeutic attribute is incorporated into the iPSCs either through reprogramming a selected source cell that is donor-, disease-, or treatment response-specific, or through introducing genetically modified modalities to iPSC using genomic editing. In the aspect of a source cell obtained from a specifically selected donor, disease or treatment context, the genetic imprint contributing to preferential therapeutic attributes may include any context specific genetic or epigenetic modifications which manifest a retainable phenotype, i.e. a preferential therapeutic attribute, that is passed on to derivative cells of the selected source cell, irrespective of the underlying molecular events being identified or not. Donor-, disease-, or treatment response-specific source cells may comprise genetic imprints that are retainable in iPSCs and derived hematopoietic lineage cells, which genetic imprints include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

The term "enhanced therapeutic property" as used herein, refers to a therapeutic property of a cell that is enhanced as compared to a typical immune cell of the same general cell type. For example, an NK cell with an "enhanced therapeutic property" will possess an enhanced, improved, and/or augmented therapeutic property as compared to a typical, unmodified, and/or naturally occurring NK cell. Therapeutic properties of an immune cell may include, but are not limited to, cell engraftment, trafficking, homing, viability, self-renewal, persistence, immune response regulation and modulation, survival, and cytotoxicity. Therapeutic properties of an immune cell are also manifested by antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

As used herein, the term "engager" refers to a molecule, e.g. a fusion polypeptide, which is capable of forming a link between an immune cell, e.g. a T cell, a NK cell, a NKT cell, a B cell, a macrophage, a neutrophil, and a tumor cell; and activating the immune cell. Examples of engagers include, but are not limited to, bi-specific T cell engagers (BiTEs), bi-specific killer cell engagers (BiKEs), tri-specific killer cell engagers, or multi-specific killer cell engagers, or universal engagers compatible with multiple immune cell types.

As used herein, the term "surface triggering receptor" refers to a receptor capable of triggering or initiating an immune response, e.g. a cytotoxic response. Surface triggering receptors may be engineered, and may be expressed on effector cells, e.g. a T cell, a NK cell, a NKT cell, a B cell, a macrophage, a neutrophil. In some embodiments, the surface triggering receptor facilitates bi- or multi-specific antibody engagement between the effector cells and specific target cell e.g. a tumor cell, independent of the effector cell's natural receptors and cell types. Using this approach, one may generate iPSCs comprising a universal surface triggering receptor, and then differentiate such iPSCs into populations of various effector cell types that express the universal surface triggering receptor. By "universal", it is meant that the surface triggering receptor can be expressed in, and activate, any effector cells irrespective of the cell type, and all effector cells expressing the universal receptor can be coupled or linked to the engagers having the same epitope recognizable by the surface triggering receptor, regardless of the engager's tumor binding specificities. In some embodiments, engagers having the same tumor targeting specificity are used to couple with the universal surface triggering receptor. In some embodiments, engagers having different tumor targeting specificity are used to couple with the universal surface triggering receptor. As such, one or multiple effector cell types can be engaged to kill one specific type of tumor cells in some case, and to kill two or more types of tumors in some other cases. A surface triggering receptor generally comprises a co-stimulatory domain for effector cell activation and an anti-epitope that is specific to the epitope of an engager. A bi-specific engager is specific to the anti-epitope of a surface triggering receptor on one end, and is specific to a tumor antigen on the other end.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis, DNA replication, growth arrest, transcriptional and post-transcriptional genetic regulation and/or antibody-mediated depletion. In some instance, the safety switch protein is activated by an exogenous molecule, e.g. a prodrug, that when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

As used herein, the term "pharmaceutically active proteins or peptides" refer to proteins or peptides that are capable of achieving a biological and/or pharmaceutical effect on an organism. A pharmaceutically active protein has healing curative or palliative properties against a disease and may be administered to ameliorate relieve, alleviate, reverse or lessen the severity of a disease. A pharmaceutically active protein also has prophylactic properties and is used to prevent the onset of a disease or to lessen the severity of such disease or pathological condition when it does emerge. Pharmaceutically active proteins include an entire protein or peptide or pharmaceutically active fragments thereof. It also includes pharmaceutically active analogs of the protein or peptide or analogs of fragments of the protein or peptide. The term pharmaceutically active protein also refers to a plurality of proteins or peptides that act cooperatively or synergistically to provide a therapeutic benefit. Examples of pharmaceutically active proteins or peptides include, but are not limited to, receptors, binding proteins, transcription and translation factors, tumor growth suppressing proteins, antibodies or fragments thereof, growth factors, and/or cytokines.

As used herein, the term "signaling molecule" refers to any molecule that modulates, participates in, inhibits, activates, reduces, or increases, the cellular signal transduction. Signal transduction refers to the transmission of a molecular signal in the form of chemical modification by recruitment of protein complexes along a pathway that ultimately triggers a biochemical event in the cell. Signal transduction pathways are well known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "targeting modality" refers to a molecule, e.g., a polypeptide, that is genetically incorporated into a cell to promote antigen and/or epitope specificity that includes but not limited to i) antigen specificity as it related to a unique chimeric antigen receptor (CAR) or T cell receptor (TCR), ii) engager specificity as it related to monoclonal antibodies or bispecific engager, iii) targeting of transformed cell, iv) targeting of cancer stem cell, and v) other targeting strategies in the absence of a specific antigen or surface molecule.

As used herein, the term "specific" or "specificity" can be used to refer to the ability of a molecule, e.g., a receptor or an engager, to selectively bind to a target molecule, in contrast to non-specific or non-selective binding.

The term "adoptive cell therapy" as used herein refers to a cell-based immunotherapy that, as used herein, relates to the transfusion of autologous or allogenic lymphocytes, identified as T or B cells, genetically modified or not, that have been expanded ex vivo prior to said transfusion.

A "therapeutically sufficient amount", as used herein, includes within its meaning a non-toxic but sufficient and/or effective amount of the particular therapeutic and/or pharmaceutical composition to which it is referring to provide a desired therapeutic effect. The exact amount required will vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate the lineage-specific differentiation. "Embryoid bodies" are three-dimensional clusters that have been shown to mimic embryo development as they give rise to numerous lineages within their three-dimensional area. Through the differentiation process, typically few hours to days, simple EBs (for example, aggregated pluripotent stem cells elicited to differentiate) continue maturation and develop into a cystic EB at which time, typically days to few weeks, they are further processed to continue differentiation. EB formation is initiated by bringing pluripotent stem cells into close proximity with one another in three-dimensional multilayered clusters of cells, typically this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to differentiation medium that provides eliciting cues towards the lineage of choice. EB-based culture of pluripotent stem cells typically results in generation of differentiated cell populations (ectoderm, mesoderm and endoderm germ layers) with modest proliferation within the EB cell cluster. Although proven to facilitate cell differentiation, EBs, however, give rise to heterogeneous cells in variable differentiation state because of the inconsistent exposure of the cells in the three-dimensional structure to differentiation cues from the environment. In addition, EBs are laborious to create and maintain. Moreover, cell differentiation through EB is accompanied with modest cell expansion, which also contributes to low differentiation efficiency.

In comparison, "aggregate formation," as distinct from "EB formation," can be used to expand the populations of pluripotent stem cell derived cells. For example, during aggregate-based pluripotent stem cell expansion, culture media are selected to maintain proliferation and pluripotency. Cells proliferation generally increases the size of the aggregates forming larger aggregates, these aggregates can be routinely mechanically or enzymatically dissociated into smaller aggregates to maintain cell proliferation within the culture and increase numbers of cells. As distinct from EB culture, cells cultured within aggregates in maintenance culture maintain markers of pluripotency. The pluripotent stem cell aggregates require further differentiation cues to induce differentiation.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation for differentiation initiation. Because monolayer culturing does not mimic embryo development such as EB formation, differentiation towards specific lineages are deemed as minimal as compared to all three germ layer differentiation in EB.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell type, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

"Functional" as used in the context of genomic editing or modification of iPSC, and derived non-pluripotent cells differentiated therefrom, or genomic editing or modification of non-pluripotent cells and derived iPSCs reprogrammed therefrom, refers to (1) at the gene level—successful knocked-in, knocked-out, knocked-down gene expression, transgenic or controlled gene expression such as inducible or temporal expression at a desired cell development stage, which is achieved through direct genomic editing or modification, or through "passing-on" via differentiation from or reprogramming of a starting cell that is initially genomically engineered; or (2) at the cell level—successful removal, adding, or altering a cell function/characteristics via (i) gene expression modification obtained in said cell through direct genomic editing, (ii) gene expression modification maintained in said cell through "passing-on" via differentiation from or reprogramming of a starting cell that is initially genomically engineered; (iii) down-stream gene regulation in said cell as a result of gene expression modification that only appears in an earlier development stage of said cell, or only appears in the starting cell that gives rise to said cell via differentiation or reprogramming; or (iv) enhanced or newly attained cellular function or attribute displayed within the mature cellular product, initially derived from the genomic editing or modification conducted at the iPSC, progenitor or dedifferentiated cellular origin.

"HLA deficient", including HLA-class I deficient, or HLA-class II deficient, or both, refers to cells that either lack, or no longer maintain, or have reduced level of surface expression of a complete MHC complex comprising a HLA class I protein heterodimer and/or a HLA class II heterodimer, such that the diminished or reduced level is less than the level naturally detectable by other cells or by synthetic methods.

"Modified HLA deficient iPSC," as used herein, refers to HLA deficient iPSC that is further modified by introducing genes expressing proteins related but not limited to improved differentiation potential, antigen targeting, antigen presentation, antibody recognition, persistence, immune evasion, resistance to suppression, proliferation, costimulation, cytokine stimulation, cytokine production (autocrine or paracrine), chemotaxis, and cellular cytotoxicity, such as non-classical HLA class I proteins (e.g., HLA-E and HLA-G), chimeric antigen receptor (CAR), T cell receptor (TCR), CD16 Fc Receptor, BCL11b, NOTCH, RUNX1, IL15, 41BB, DAP10, DAP12, CD24, CD3z, 41BBL, CD47, CD113, and PDL1. The cells that are "modified HLA deficient" also include cells other than iPSCs.

"Fc receptors," abbreviated FcR, are classified based on the type of antibody that they recognize. For example, those that bind the most common class of antibody, IgG, are called Fc-gamma receptors (FcγR), those that bind IgA are called Fc-alpha receptors (FcαR) and those that bind IgE are called Fc-epsilon receptors (FcεR). The classes of FcR's are also distinguished by the cells that express them (macrophages, granulocytes, natural killer cells, T and B cells) and the signaling properties of each receptor. Fc-gamma receptors (FcγR) includes several members, FcγRI (CD64), FcγRIIA (CD32), FcγRIIB (CD32), FcγRIIIA (CD16a), FcγRIIIB (CD16b), which differ in their antibody affinities due to their different molecular structure.

"Chimeric Fc Receptor," abbreviated as CFcR, are terms used to describe engineered Fc receptors having their native transmembrane and/or intracellular signaling domains modified, or replaced with non-native transmembrane and/or intracellular signaling domains. In some embodiments of the chimeric Fc receptor, in addition to having one of, or both, transmembrane and signaling domains being non-native, one or more stimulatory domains can be introduced to the intracellular portion of the engineered Fc receptor to enhance cell activation, expansion and function upon triggering of the receptor. Unlike chimeric antigen receptor (CAR) which contains antigen binding domain to target antigen, the chimeric Fc receptor binds to an Fc fragment, or the Fc region of an antibody, or the Fc region comprised in an engager or a binding molecule and activating the cell function with or without bringing the targeted cell close in vicinity. For example, a Fey receptor can be engineered to comprise selected transmembrane, stimulatory, and/or signaling domains in the intracellular region that respond to the binding of IgG at the extracellular domain, thereby generating a CFcR. In one example, a CFcR is produced by engineering CD16, a Fcγreceptor, by replacing its transmembrane domain and/or intracellular domain. To further improve the binding affinity of the CD16 based CFcR, the extracellular domain of CD64 or the high-affinity variants of CD16 (F176V, for example) can be incorporated. In some embodiments of the CFcR where high affinity CD16 extracellular domain is involved, the proteolytic cleavage site comprising a serine at position 197 is eliminated or is replaced such at the extracellular domain of the receptor is non-cleavable, i.e., not subject to shedding, thereby obtaining a hnCD16 based CFcR.

CD16, a FcγR receptor, has been identified to have two isoforms, Fc receptors FcγRIIIa (CD16a) and FcγRIIIb (CD16b). CD16a is a transmembrane protein expressed by NK cells, which binds monomeric IgG attached to target cells to activate NK cells and facilitate antibody-dependent cell-mediated cytotoxicity (ADCC). "High affinity CD16," "non-cleavable CD16," or "high affinity non-cleavable CD16 (hnCD16)," as used herein, refers to a natural or non-natural variant of CD16. The wildtype CD16 has low affinity and is subject to extodomain shedding, a proteolytic cleavage process that regulates the cells surface density of various cell surface molecules on leukocytes upon NK cell activation. F176V and F158V are exemplary CD16 polymorphic variants having high affinity. A CD16 variant having the cleavage site (position 195-198) in the membrane-proximal region (position 189-212) altered or eliminated is not subject to shedding. The cleavage site and the membrane-proximal region are described in detail in WO2015148926, the complete disclosures of which are incorporated herein by reference. The CD16 S197P variant is an engineered non-cleavable version of CD16. A CD16 variant comprising both F158V and S197P has high affinity and is non-cleavable. Another exemplary high affinity and non-cleavable CD16 (hnCD16) variant is an engineered CD16 comprising an ectodomain originated from one or more of the 3 exons of the CD64 ectodomain.

I. Cells and Compositions Useful for Adoptive Cell Therapies with Enhanced Properties Provided herein is a strategy to systematically engineer the regulatory circuitry of a clonal iPSC without impacting the differentiation potency of the iPSC and cell development biology of the iPSC and its derivative cells, while enhancing the therapeutic properties of the derivative cells. The derivative cells are functionally improved and suitable for adoptive cell therapies following a combination of selective modalities being introduced to the cells at the level of iPSC through genomic engineering. It was unclear, prior to this invention, whether altered iPSCs comprising one or more provided genetic editing still have the capacity to enter cell development, and/or to mature and generate functional differentiated cells while retaining modulated activities. Unanticipated failures during directed cell differentiation from iPSCs have been attributed to aspects including, but not limited to, development stage specific gene expression or lack thereof, requirements for HLA complex presentation, protein shedding of introduced surface expressing modalities, and need for reconfiguration of differentiation protocols enabling phenotypic and/or functional change in the cell. The present application has shown that the one or more selected genomic modifications as provided herein does not negatively impact iPSC differentiation potency, and the functional effector cells derived from the engineered iPSC have enhanced and/or acquired therapeutic properties attributable to the individual or combined genomic modifications retained in the effector cells following the iPSC differentiation.

1. CD38 Knockout

Cell surface molecule CD38 is highly upregulated in multiple hematologic malignancies derived from both lymphoid and myeloid lineages, including multiple myeloma and a CD20 negative B-cell malignancy, which makes it an attractive target for antibody therapeutics to deplete cancer cell. Antibody mediated cancer cell depletion is usually attributable to a combination of direct cell apoptosis induction and activation of immune effector mechanisms such as ADCC (antibody-dependent cell-mediated cytotoxicity). In addition to ADCC, the immune effector mechanisms in concert with the therapeutic antibody may also include phagocytosis (ADCP) and/or complement-dependent cytotoxicity (CDC).

Other than being highly expressed on malignant cells, CD38 is also expressed on plasma cells as well as on NK cells, and activated T and B cells. During hematopoiesis, CD38 is expressed on $CD34^+$ stem cells and lineage-committed progenitors of lymphoid, erythroid, and myeloid, and during the final stages of maturation which continues through the plasma cell stage. As a type II transmembrane glycoprotein, CD38 carries out cell functions as both a receptor and a multifunctional enzyme involved in the production of nucleotide-metabolites. As an enzyme, CD38 catalyzes the synthesis and hydrolysis of the reaction from $NAD^+$ to ADP-ribose, thereby producing secondary messengers CADPR and NAADP which stimulate release of calcium from the endoplasmic reticulum and lysosomes, critical for the process of cell adhesion which process is calcium dependent. As a receptor, CD38 recognizes CD31 and regulates cytokine release and cytotoxicity in activated NK cells. CD38 is also reported to associate with cell surface proteins in lipid rafts, to regulate cytoplasmic $Ca^{2+}$ flux, and to mediate signal transduction in lymphoid and myeloid cells.

In malignancy treatment, systemic use of CD38 antigen binding receptor transduced T cells have been shown to lyse the CD38+ fractions of CD34+ hematopoietic progenitor cells, monocytes, NK cells, T cells and B cells, leading to incomplete treatment responses and reduced or eliminated efficacy because of the impaired recipient immune effector cell function. In addition, in multiple myeloma patients treated with daratumumab, a CD38 specific antibody, NK cell reduction in both bone marrow and peripheral blood was observed, although other immune cell types, such as T cells and B cells, were unaffected despite their CD38 expression (Casneuf et al., Blood Advances. 2017; 1(23):2105-2114). Without being limited by theories, the present application provides a strategy to leverage the full potential of CD38 targeted cancer treatment by overcoming CD38 specific antibody and/or CD38 antigen binding domain induced effector cell depletion or reduction through fratricide. In addition, since CD38 is upregulated on activated lymphocytes such as T or B cells, by suppressing activation of these lymphocytes using CD38 specific antibody such as daratumumab in the recipient of allogeneic effector cells, the allorejection against these effector cells would be reduced and/or prevented and thereby increasing effector cell survival and persistency. As such, the present application also provides a strategy to enhance effector cell persistency and/or survival through reducing or preventing allorejection by using CD38 specific antibody, a secreted CD38 specific engager or a CD38 CAR (chimeric antigen receptor) against activation of recipient T and B cells. Specifically, the strategies as provided include generating a CD38 knockout iPSC line and obtaining CD38 null ($CD38^{-/-}$) derivative effector cells through directed differentiation of the engineered iPSC line. Prior to this application, it was unknown whether disrupting CD38 in iPSC would perturb any of the aspects, including iPSC differentiation, derivative cell phenotype and effector cell function, considering that CD38 plays many key roles in cell developmental biology and cell function as described above.

In one embodiment as provided herein, the CD38 knockout in an iPSC line is a bi-allelic knockout. As disclosed herein, the provided CD38 null iPSC line is capable of directed differentiation to produce functional derivative hematopoietic cells including, but not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages. In some embodiments, when an anti-CD38 antibody is used to induce ADCC or an anti-CD38 CAR is used for targeted cell killing, the $CD38^{-/-}$ iPSC and/or its derivative effector cells thereof are not eliminated by the anti-CD38 antibody or the anti-CD38 CAR, thereby increasing the iPSC and its effector cell persistence and/or survival in the presence of, and/or after exposure to, such therapeutic agents. In some embodiments, the effector cell has increased persistence and/or survival in vivo in the presence of, and/or after exposure to, such therapeutic agents. In some embodiments, the CD38 null effector cells are NK cells derived from iPSCs. In some embodiments, the CD38 null effector cells are T cells derived from iPSCs. In some embodiments, the CD38 null iPSC and derivative cells comprise one or more additional genomic editing as described herein, including but not limited to, hnCD16 expression, CAR expression, cytokine/cytokine receptor expression, HLA I and/or HLAII knock out, and additional modalities as provided.

2. hnCD16 Knock-In

CD16 has been identified as two isoforms, Fc receptors FcγRIIIa (CD16a; NM_000569.6) and FcγRIIIb (CD16b; NM_000570.4). CD16a is a transmembrane protein expressed by NK cells, which binds monomeric IgG attached to target cells to activate NK cells and facilitate antibody-dependent cell-mediated cytotoxicity (ADCC). CD16b is exclusively expressed by human neutrophils. "High affinity CD16," "non-cleavable CD16," or "high affinity non-cleavable CD16," as used herein, refers to various CD16 variants. The wildtype CD16 has low affinity and is subject to ectodomain shedding, a proteolytic cleavage process that regulates the cells surface density of various cell surface molecules on leukocytes upon NK cell activation. F176V (also called F158V in some publications) is an exemplary CD16 polymorphic variant having high affinity; whereas S197P variant is an example of genetically engineered non-cleavable version of CD16. An engineered CD16 variant comprising both F176V and S197P has high affinity and is non-cleavable, which was described in greater detail in WO2015/148926, and the complete disclosure of which is incorporated herein by reference. In addition, a chimeric CD16 receptor with the ectodomain of CD16 essentially replaced with at least a portion of CD64 ectodomain can also achieve the desired high affinity and non-cleavable features of a CD16 receptor capable of carrying out ADCC. In some embodiments, the replacement ectodomain of a chimeric CD16 comprises one or more of EC1, EC2, and EC3 exons of CD64 (UniPRotKB P12314 or its isoform or polymorphic variant).

As such, a high-affinity non-cleavable CD16 receptor (hnCD16), in some embodiments, comprises both F176V and S197P; and in some embodiments, comprises F176V and with the cleavage region eliminated. In some other embodiments, a hnCD16 comprises a sequence having identity of at least 50%, 55%, 60%, 65%, 70%, 75%, 80%, 85%, 90%, 95%, 99%, 100%, or any percentage in-between, when compared to any of the exemplary sequences, SEQ ID NOs. 7, 8 and 9, each comprises at least a portion of CD64 ectodomain. SEQ ID NOs. 7, 8 and 9 are encoded respectively by exemplifying SEQ ID NOs. 10-12. As used herein and throughout the application, the percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm recognized in the art.

SEQ ID NO. 7:
MWFLTTLLLWVPVDGQVDTTKAVITLQPPWVSVFQEETVTLHCEVLHLPGSSSTQWFLNGT

ATQTSTPSYRITSASVNDSGEYRCQRGLSGRSDPIQLEIHRGWLLLQVSSRVFTEGEPLAL

RCHAWKDKLVYNVLYYRNGKAFKFFHWNSNLTILKTNISHNGTYHCSGMGKHRYTSAGISV

TVKELFPAPVLNASVTSPLLEGNLVTLSCETKLLLQRPGLQLYFSFYMGSKTLRGRNTSSE

YQILTARREDSGLYWCEAATEDGNVLKRSPELELQVLGLQLPTPVWFHY*QVSFCLVMVLLF*

*AVDTGLYFSVKTNIRSSTRDWKDHKFKWRKDPQDK*
(340 a.a. CD64 domain-based construction; CD16TM; CD16ICD)

SEQ ID NO. 8
MWFLTTLLLWVPVDGQVDTTKAVITLQPPWVSVFQEETVTLHCEVLHLPGSSSTQWFLNGT

ATQTSTPSYRITSASVNDSGEYRCQRGLSGRSDPIQLEIHRGWLLLQVSSRVFTEGEPLAL

RCHAWKDKLVYNVLYYRNGKAFKFFHWNSNLTILKTNISHNGTYHCSGMGKHRYTSAGISV

TVKELFPAPVLNASVTSPLLEGNLVTLSCETKLLLQRPGLQLYFSFYMGSKTLRGRNTSSE

YQILTARREDSGLYWCEAATEDGNVLKRSPELELQVLGLFFPPGY*QVSFCLVMVLLFAVDT*

*GLYFSVKTNIRSSTRDWKDHKFKWRKDPQDK*
(336 a.a. CD64 exon-based construction; CD16TM; CD16ICD)

SEQ ID NO. 9
MWFLTTLLLWVPVDGQVDTTKAVITLQPPWVSVFQEETVTLHCEVLHLPGSSSTQWFLNG

TATQTSTPSYRITSASVNDSGEYRCQRGLSGRSDPIQLEIHRGWLLLQVSSRVFTEGEPL

ALRCHAWKDKLVYNVLYYRNGKAFKFFHWNSNLTILKTNISHNGTYHCSGMGKHRYTSAG

ISVTVKELFPAPVLNASVTSPLLEGNLVTLSCETKLLLQRPGLQLYFSFYMGSKTLRGRN

TSSEYQILTARREDSGLYWCEAATEDGNVLKRSPELELQVLGFFPPGY*QVSFCLVMVLLF*

*AVDTGLYFSVKTNIRSSTRDWKDRKFKWRKDPQDK*
(335 a.a. CD64 exon-based construction; CD16TM; CD16ICD)

SEQ ID NO. 10
cttggagaca acatgtggtt cttgacaact ctgctccttt gggttccagt tgatgggcaa gtggacacca caaaggcagt gatcactttg cagcctccat gggtcagcgt gttccaagag gaaaccgtaa ccttgcattg tgaggtgctc catctgcctg ggagcagctc tacacagtgg tttctcaatg gcacagccac tcagacctcg acccccagct acagaatcac ctctgccagt gtcaatgaca gtggtgaata caggtgccag agaggtctct cagggcgaag tgaccccata cagctggaaa tccacagagg ctggctacta ctgcaggtct ccagcagagt cttcacggaa ggagaacctc tggccttgag gtgtcatgcg tggaaggata agctggtgta caatgtgctt tactatcgaa atggcaaagc ctttaagttt ttccactgga attctaacct caccattctg aaaaccaaca taagtcacaa tggcacctac cattgctcag gcatgggaaa gcatcgctac acatcagcag gaatatctgt cactgtgaaa gagctatttc cagctccagt gctgaatgca -continued

```
tctgtgacat ccccactcct ggaggggaat ctggtcaccc tgagctgtga aacaaagttg
ctcttgcaga ggcctggttt gcagctttac ttctccttct acatgggcag caagaccctg
cgaggcagga acacatcctc tgaataccaa atactaactg ctagaagaga agactctggg
ttatactggt gcgaggctgc cacagaggat ggaaatgtcc ttaagcgcag ccctgagttg
gagcttcaag tgcttggcct ccagttacca actcctgtct ggtttcatta ccaagtctct
ttctgcttgg tgatggtact cctttttgca gtggacacag gactatattt ctctgtgaag
acaaacattc gaagctcaac aagagactgg aaggaccata aatttaaatg gagaaaggac
cctcaagaca aa
```

SEQ ID NO. 11

```
cttggagaca acatgtggtt cttgacaact ctgctccttt gggttccagt tgatgggcaa
gtggacacca caaaggcagt gatcactttg cagcctccat gggtcagcgt gttccaagag
gaaaccgtaa ccttgcattg tgaggtgctc catctgcctg ggagcagctc tacacagtgg
tttctcaatg gcacagccac tcagacctcg acccccagct acagaatcac ctctgccagt
gtcaatgaca gtggtgaata caggtgccag agaggtctct cagggcgaag tgaccccata
cagctggaaa tccacagagg ctggctacta ctgcaggtct ccagcagagt cttcacggaa
ggagaacctc tggccttgag gtgtcatgcg tggaaggata agctggtgta caatgtgctt
tactatcgaa atggcaaagc ctttaagttt ttccactgga attctaacct caccattctg
aaaaccaaca taagtcacaa tggcacctac cattgctcag gcatgggaaa gcatcgctac
acatcagcag gaatatctgt cactgtgaaa gagctatttc cagctccagt gctgaatgca
tctgtgacat ccccactcct ggaggggaat ctggtcaccc tgagctgtga aacaaagttg
ctcttgcaga ggcctggttt gcagctttac ttctccttct acatgggcag caagaccctg
cgaggcagga acacatcctc tgaataccaa atactaactg ctagaagaga agactctggg
ttatactggt gcgaggctgc cacagaggat ggaaatgtcc ttaagcgcag ccctgagttg
gagcttcaag tgcttggttt gttctttcca cctgggtacc aagtctcttt ctgcttggtg
atggtactcc tttttgcagt ggacacagga ctatatttct ctgtgaagac aaacattcga
agctcaacaa gagactggaa ggaccataaa tttaaatgga gaaaggaccc tcaagacaaa
```

SEQ ID NO. 12

```
atgtggttct tgacaactct gctcctttgg gttccagttg atgggcaagt ggacaccaca
aaggcagtga tcactttgca gcctccatgg gtcagcgtgt tccaagagga aaccgtaacc
ttgcactgtg aggtgctcca tctgcctggg agcagctcta cacagtggtt tctcaatggc
acagccactc agacctcgac ccccagctac agaatcacct ctgccagtgt caatgacagt
ggtgaataca ggtgccagag aggtctctca gggcgaagtg accccataca gctggaaatc
cacagaggct ggctactact gcaggtctcc agcagagtct tcacggaagg agaacctctg
gccttgaggt gtcatgcgtg gaaggataag ctggtgtaca atgtgcttta ctatcgaaat
ggcaaagcct ttaagttttt ccactggaac tctaacctca ccattctgaa aaccaacata
agtcacaatg gcacctacca ttgctcaggc atgggaaagc atcgctacac atcagcagga
atatctgtca ctgtgaaaga gctatttcca gctccagtgc tgaatgcatc tgtgacatcc
ccactcctgg aggggaatct ggtcaccctg agctgtgaaa caaagttgct cttgcagagg
cctggtttgc agctttactt ctccttctac atgggcagca agaccctgcg aggcaggaac
acatcctctg aataccaaat actaactgct agaagagaag actctgggtt atactggtgc
gaggctgcca cagaggatgg aaatgtcctt aagcgcagcc ctgagttgga gcttcaagtg
cttggcttct ttccacctgg gtaccaagtc tctttctgct tggtgatggt actccttttt
```

-continued

```
gcagtggaca caggactata tttctctgtg aagacaaaca ttcgaagctc aacaagagac

tggaaggacc ataaatttaa atggagaaag gaccctcaag acaaa
```

Accordingly, provided herein are clonal iPSCs genetically engineered to comprise, among other editing as contemplated and described herein, a high-affinity non-cleavable CD16 receptor (hnCD16), wherein the genetically engineered iPSCs are capable of differentiating into effector cells comprising the hnCD16 introduced to the iPSCs. In some embodiments, the derived effector cells comprising hnCD16 are NK cells. In some embodiments, the derived effector cells comprising hnCD16 are T cells. The exogenous hnCD16 expressed in iPSC or derivative cells thereof has high affinity in binding to not only ADCC antibodies or fragments thereof, but also to bi-, tri-, or multi-specific engagers or binders that recognize the CD16 or CD64 extracellular binding domains of said hnCD16. The bi-, tri-, or multi-specific engagers or binders are further described below in this application (see section I.7). As such, the present application provides a derivative effector cell or a cell population thereof, preloaded with one or more pre-selected ADCC antibody through high-affinity binding with the extracellular domain of the hnCD16 expressed on the derivative effector cell, in an amount sufficient for therapeutic use in a treatment of a condition, a disease, or an infection as further detailed in section V. below, wherein said hnCD16 comprises an extracellular binding domain of CD64, or of CD16 having F176V and S197P.

In some other embodiments, the native CD16 transmembrane- and/or the intracellular-domain of a hnCD16 is further modified or replaced, such that a chimeric Fc receptor (CFcR) is produced to comprise a non-native transmembrane domain, a non-native stimulatory domain and/or a non-native signaling domain. The term “non-native” used herein means that the transmembrane, stimulatory or signaling domain are derived from a different receptor other than the receptor which provides the extracellular domain. In the illustration here, the CFcR based on CD16 or variants thereof does not have a transmembrane, stimulatory or signaling domain that is derived from CD16. In some embodiments, the exogenous hnCD16 based CFcR comprises a non-native transmembrane domain derived from CD3D, CD3E, CD3G, CD3c CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C NKG2D, T cell receptor polypeptide. In some embodiments, the exogenous hnCD16 based CFcR comprises a non-native stimulatory/inhibitory domain derived from CD27, CD28, 4-1BB, OX40, ICOS, PD-1, LAG-3, 2B4, BTLA, DAP10, DAP12, CTLA-4, or NKG2D polypeptide. In some embodiments, the exogenous hnCD16 based CFcR comprises a non-native signaling domain derived from CD3ζ, 2B4, DAP10, DAP12, DNAM1, CD137 (41BB), IL21, IL7, IL12, IL15, NKp30, NKp44, NKp46, NKG2C, or NKG2D polypeptide. In one embodiment of hnCD16, the provided chimeric receptor comprises a transmembrane domain and a signaling domain both derived from one of IL7, IL12, IL15, NKp30. NKp44, NKp46, NKG2C, and NKG2D polypeptide. One particular embodiment of the hnCD16 based chimeric Fc receptor comprises a transmembrane domain of NKG2D, a stimulatory domain of 2B4, and a signaling domain of CD3ζ; wherein the extracellular domain of the hnCD16 is derived from a full length or partial sequence of the extracellular domain of CD64 or CD16, wherein the extracellular domain of CD16 comprises F176V and S197P. Another embodiment of the hnCD16 based chimeric Fc receptor comprises a transmembrane domain and a signaling domain of CD3ζ; wherein the extracellular domain of the hnCD16 is derived from a full length or partial sequence of the extracellular domain of CD64 or CD16, wherein the extracellular domain of CD16 comprises F176V and S197P.

The various embodiments of hnCD16 based chimeric Fc receptor as described above are capable of binding, with high affinity, to the Fc region of an antibody or fragment thereof; or to the Fc region of a bi-, tri-, or multi-specific engager or binder. Upon binding, the stimulatory and/or signaling domains of the chimeric receptor enable the activation and cytokine secretion of the effector cells, and the killing of the tumor cells targeted by the antibody, or said bi-, tri-, or multi-specific engager or binder having a tumor antigen binding component as well as the Fc region. Without being limited by theory, through the non-native transmembrane, stimulatory and/or signaling domains, or through an engager binding to the ectodomain, of the hnCD16 based chimeric Fc receptor, the CFcR could contribute to effector cells' killing ability while increasing the effector cells' proliferation and/or expansion potential. The antibody and the engager can bring tumor cells expressing the antigen and the effector cells expressing the CFcR into a close proximity, which also contributes to the enhanced killing of the tumor cells. Exemplary tumor antigen for bi-, tri-, multi-specific engager or binders include, but are not limited to, B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, and ROR1. Some non-limiting exemplary bi-, tri-, multi-specific engager or binders suitable for engaging effector cells expressing the hnCD16 based CFcR in attacking tumor cells include CD16 (or CD64)-CD30, CD16 (or CD64)-BCMA, CD16 (or CD64)-IL15-EPCAM, and CD16 (or CD64)-IL15-CD33.

Unlike the endogenous CD16 receptor expressed by primary NK cells which gets cleaved from the cellular surface following NK cell activation, the various non-cleavable versions of CD16 in derivative NK avoids CD16 shedding and maintains constant expression. In derivative NK cell, non-cleavable CD16 increases expression of TNFa and CD107a indicative of improved cell functionality. Non-cleavable CD16 also enhances the antibody-dependent cell-mediated cytotoxicity (ADCC), and the engagement of bi-, tri-, or multi-specific engagers. ADCC is a mechanism of NK cell mediated lysis through the binding of CD16 to antibody-coated target cells. The additional high affinity characteristics of the introduced hnCD16 in derived NK cell also enables in vitro loading of ADCC antibody to the NK cell through hnCD16 before administering the cell to a subject in need of a cell therapy. As provided, the hnCD16 may comprise F176V and S197P in some embodiments, or may comprise a full or partial ectodomain originated from CD64 as exemplified by SEQ ID NO: 7, 8 or 9, or may further comprises at least one of non-native transmembrane domain, stimulatory domain and signaling domain. As disclosed, the present application also provides a derivative NK cell or a cell population thereof, preloaded with one or more pre-selected ADCC antibody in an amount sufficient for therapeutic use in a treatment of a condition, a disease, or an infection as further detailed in section V. below. In some embodiments, the derived NK cells comprising hnCD16 further comprise CD38 knockout. In some embodiments, the derived NK cells comprising hnCD16 and CD38 knockout are preloaded with anti-CD38 antibody. In some embodiments, the preloaded anti-CD38 antibody is daratumumab.

Unlike primary NK cells, mature T cells from a primary source (i.e., natural/native sources such as peripheral blood, umbilical cord blood, or other donor tissues) do not express CD16. It was unexpected that iPSC comprising an expressed exogenous non-cleavable CD16 did not impair the T cell developmental biology and was able to differentiate into functional derivative T cells that not only express the exogenous CD16, but also are capable of carrying out function through an acquired ADCC mechanism. This acquired ADCC in the derivative T cell can additionally be used as an approach for dual targeting and/or to rescue antigen escape often occurred with CAR-T cell therapy, where the tumor relapses with reduced or lost CAR-T targeted antigen expression or expression of a mutated antigen to avoid recognition by the CAR (chimerical antigen receptor). When said derivative T cell comprises acquired ADCC through exogenous CD16 expression, and when an antibody targets a different tumor antigen from the one targeted by the CAR, the antibody can be used to rescue CAR-T antigen escape and reduce or prevent relapse or recurrence of the targeted tumor often seen in CAR-T treatment. Such a strategy to reduce and/or prevent antigen escape while achieving dual targeting is equally applicable to NK cells expressing one or more CARs. The various CARs that can be used in this antigen escape reduction and prevention strategy is further delineated below.

As such, the present invention provides a derivative T cell comprising an exogenous CD16. In a further provided embodiment, the derivative T cell obtained herein comprises CD38 knockout in addition to the expression of an hnCD16. In some embodiments, the hnCD16 comprised in the derivative T cell comprises F176V and S197P. In some other embodiments, the hnCD16 comprised in the derivative T cell comprises a full or partial ectodomain originated from CD64 as exemplified by SEQ ID NO: 7, 8 or 9; or may further comprises at least one of non-native transmembrane domain, stimulatory domain and signaling domain. As explained, such derivative T cells have an acquired mechanism to target tumors with a monoclonal antibody meditated by ADCC to enhance the therapeutic effect of the antibody. As disclosed, the present application also provides a derivative T cell, or a cell population thereof, preloaded with one or more pre-selected ADCC antibody in an amount sufficient for therapeutic use in a treatment of a condition, a disease, or an infection as further detailed in section V below. In some other embodiments, the derivative T cells expressing a hnCD16 is also CD38 null, such that the cells can avoid being eliminated when in the presence of a therapeutics targeting the tumor antigen CD38. In one embodiment, said therapeutics targeting the tumor antigen CD38 is an anti-CD38 antibody. In another embodiment, said therapeutics targeting the tumor antigen CD38 is a CAR comprising a CD38 binding region, for example, an anti-CD38 scFV.

3. CAR Expression

Applicable to the genetically engineered iPSC and derivative effector cell thereof may be any CAR design known in the art. CAR, a chimerical antigen receptor, is a fusion protein generally including an ectodomain that comprises an antigen recognition region, a transmembrane domain, and an endo-domain. In some embodiments, the ectodomain can further include a signal peptide or leader sequence and/or a spacer. In some embodiments, the endo-domain can further comprise a signaling peptide that activates the effector cell expressing the CAR. In some embodiments, the antigen recognition domain can specifically bind an antigen. In some embodiments, the antigen recognition domain can specifically bind an antigen associated with a disease or pathogen. In some embodiments, the disease-associated antigen is a tumor antigen, wherein the tumor may be a liquid or a solid tumor. In some embodiments, the CAR is suitable to activate either T or NK cells expressing said CAR. In some embodiments, the CAR is NK cell specific for comprising NK-specific signaling components. In certain embodiments, said T cells are derived from a CAR expressing iPSCs, and the derivative T cells may comprise T helper cells, cytotoxic T cells, memory T cells, regulatory T cells, natural killer T cells, αβ T cells, γδ T cells, or a combination thereof. In certain embodiments, said NK cells are derived from a CAR expressing iPSCs.

In certain embodiments, said antigen recognition region comprises a murine antibody, a human antibody, a humanized antibody, a camel Ig, a shark heavy-chain-only antibody (VNAR), Ig NAR, a chimeric antibody, a recombinant antibody, or antibody fragment thereof. Non-limiting examples of antibody fragment include Fab, Fab', F(ab)'2, F(ab)'3, Fv, single chain antigen binding fragment (scFv), $(scFv)_2$, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody. Non-limiting examples of antigen that may be targeted by a CAR include ADGRE2, carbonic anhydrase IX (CA1X), CCRI, CCR4, carcinoembryonic antigen (CEA), CD3ζ, CD5, CD7, CD8, CD10, CD19, CD20, CD22, CD30, CD33, CD34, CD38, CD41, CD44, CD44V6, CD49f, CD56, CD70, CD74, CD99, CD123, CD133, CD138, CD269 (BCMA), CD S, CLEC12A, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBCI, TRBC2, vascular endothelial growth factor R2 (VEGF-R2), Wilms tumor protein (WT-1), and various pathogen antigen known in the art. Non-limiting examples of pathogen includes virus, bacteria, fungi, parasite and protozoa capable of causing diseases.

In some embodiments, the transmembrane domain of a CAR comprises a full length or at least a portion of the native or modified transmembrane region of CD3D, CD3E, CD3G, CD3c CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, T cell receptor polypeptide.

In some embodiments, the signaling peptide of the endodomain (or intracellular domain) comprises a full length or at least a portion of a polypeptide of CD3ζ, 2B4, DAP10, DAP12, DNAM1, CD137 (41BB), IL21, IL7, IL12, IL15, NKp30, NKp44, NKp46, NKG2C, or NKG2D. In one embodiment, the signaling peptide of a CAR comprises an amino acid sequence that is at least about 85%, about 90%, about 95%, about 96%, about 97%, about 98%, or about 99% identity to at least one ITAM (immunoreceptor tyrosine-based activation motif) of CD3ζ.

In certain embodiments, said endo-domain further comprises at least one costimulatory signaling region. Said costimulatory signaling region can comprise a full length or at least a portion of a polypeptide of CD27, CD28, 4-1BB, OX40, ICOS, PD-1, LAG-3, 2B4, BTLA, DAP10, DAP12, CTLA-4, or NKG2D, or any combination thereof.

In one embodiment, the CAR applicable to the cells provided in this application comprises a co-stimulatory domain derived from CD28, and a signaling domain comprising the native or modified ITAM1 of CD3ζ, represented by an amino acid sequence of at least about 85%, about 90%, about 95%, about 96%, about 97%, about 98%, or about 99% identity to SEQ ID NO: 13. In a further embodiment, the CAR comprising a co-stimulatory domain derived from CD28, and a native or modified ITAM1 of CD3t also comprises a hinge domain and trans-membrane domain derived from CD28, wherein an scFv may be connected to the trans-membrane domain through the hinge, and the CAR comprises an amino acid sequence of at least about 85%, about 90%, about 95%, about 96%, about 97%, about 98%, or about 99% identity to SEQ ID NO: 14.

SEQ ID NO: 13

RSKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLFNE

LQKDKMAEAFSEIGMKGERRRGKGHDGLFQGLSTATKDTFDALHMQALPPR (153 a.a. CD28 co-stim + CD3ζITAM)

SEQ ID NO: 14

*IEVMYPPPYLDNEKSNGTIIHVKGKHLCPSPLFPGPSKP*FWVLVVVGGVLA

CYSLLVTVAFIIFWVRSKRSRLLHSDYMNMTPRRPGPTRKHYQPYAPPRDF

AAYRSRVKFSRSADAPAYQQGQNQLYNELNLGRREEYDVLDKRRGRDPEMG

GKPRRKNPQEGLFNELQKDKMAEAFSEIGMKGERRRGKGHDGLFQGLSTAT

KDTFDALHMQALPPR (219 a.a. CD28 hinge + CD28 TM + CD28 co-stim + CD3ζITAM)

In another embodiment, the CAR applicable to the cells provided in this application comprises a transmembrane domain derived from NKG2D, a co-stimulatory domain derived from 2B4, and a signaling domain comprising the native or modified CD3ζ, represented by an amino acid sequence of at least about 85%, about 90%, about 95%, about 96%, about 97%, about 98%, or about 99% identity to SEQ ID NO: 15. Said CAR comprising a transmembrane domain derived from NKG2D, a co-stimulatory domain derived from 2B4, and a signaling domain comprising the native or modified CD3ζ may further comprise a CD8 hinge, wherein the amino acid sequence of such a structure is of at least about 85%, about 90%, about 95%, about 96%, about 97%, about 98%, or about 99% identity to SEQ ID NO: 16.

SEQ ID NO: 15

SNLFVASWIAVMIIFRIGMAVAIFCCFFFPSWRRKRKEKQSETSPKEFLTI

YEDVKDLKTRRNHEQEQTFPGGGSTIYSMIQSQSSAPTSQEPAYTLYSLIQ

PSRKSGSRKRNHSPSFNSTIYEVIGKSQPKAQNPARLSRKELENFDVYSRV

KFSRSADAPAYKQGQNQLYNELNLGRREEYDVLDKRRGRDPEMGGKPRRKN

PQEGLYNELQKDKMAEAYSEIGMKGERRRGKGHDGLYQGLSTATKDTYDAL

HMQALPPR (263 a.a NKG2D TM + 2B4 + CD3ζ)

SEQ ID NO: 16

*TTTPAPRPPTPAPTIASQPLSLRPEACRPAAGGAVHTRGLDFACD*SNLFVA

SWIAVMIIFRIGMAVAIFCCFFFPSWRRKRKEKQSETSPKEFLTIYEDVKD

LKTRRNHEQEQTFPGGGSTIYSMIQSQSSAPTSQEPAYTLYSLIQPSRKSG

SRKRNHSPSFNSTIYEVIGKSQPKAQNPARLSRKELENFDVYSRVKFSRSA

DAPAYKQGQNQLYNELNLGRREEYDVLDKRRGRDPEMGGKPRRKNPQEGLY

NELQKDKMAEAYSEIGMKGERRRGKGHDGLYQGLSTATKDTYDAL

HMQALPPR (308 a.a CD8 hinge + NKG2D TM + 2B4 + CD3ζ)

Non-limiting CAR strategies further include heterodimeric, conditionally activated CAR through dimerization of a pair of intracellular domain (see for example, U.S. Pat. No. 9,587,020); split CAR, where homologous recombination of antigen binding, hinge, and endo-domains to generate a CAR (see for example, U.S. Pub. No. 20170183407); multi-chain CAR that allows non-covalent link between two transmembrane domains connected to an antigen binding domain and a signaling domain, respectively (see for example, U.S. Pub. No. 20140134142); CARs having bispecific antigen binding domain (see for example, U.S. Pat. No. 9,447,194), or having a pair of antigen binding domains recognizing same or different antigens or epitopes (see for example, U.S. Pat. No. 8,409,577), or a tandem CAR (see for example, Hegde et al., *J Clin Invest.* 2016;126(8):3036-3052); inducible CAR (see for example, U.S. Pub. Nos. 20160046700, 20160058857, 20170166877); switchable CAR (see for example, U.S. Pub. No: 20140219975); and any other designs known in the art.

Provided herein therefore include derivative cells obtained from differentiating genomically engineered iPSCs, wherein both the iPSCs and the derivative cells comprise one or more CARs along with additional modified modalities, including, but not limited to, CD38 knockout and/or hnCD16. In one particular embodiment, the iPSC and its derivative cells comprises CD38 knockout, hnCD16, and a CAR targeting a selected tumor or viral antigen, wherein the derivative cells are NK or T cells, and wherein the derivative cells may be used with, through hnCD16 binding, one or more ADCC antibodies or a bi-, tri- or multi-specific engager that target a tumor antigen different from the one targeted by CAR to avoid or to reduce tumor antigen escape while achieving dual targeting of the same tumor. In a further embodiment, the iPSC and its derivative T cells comprising a CAR have the CAR inserted in a TCR constant region, leading to TCR knock out, and placing CAR expression under the control of the endogenous TCR promoter. In some embodiments, derivative TCR null CAR-T cell derived from engineered iPSCs further comprise hnCD16 having an ectodomain native to CD16 (F176V and/or S197P) or derived from CD64, and native or non-native transmembrane, stimulatory and signaling domains. In another embodiment, the iPSC and its derivative NK cells comprising a CAR have the CAR inserted in the NKG2A locus or NKG2D locus, leading to NKG2A or NKG2D knock out, and placing CAR expression under the control of the endogenous NKG2A or NKG2D promoter.

4. Exogenously Introduced cytokine and/or cytokine Signaling

By avoiding systemic high-dose administration of clinically relevant cytokines, the risk of dose-limiting toxicities due to such a practice is reduced while cytokine mediated cell autonomy being established. To achieve lymphocyte autonomy without the need to additionally administer soluble cytokines, a partial or full peptide of one or more of IL2, IL4, IL6, IL7, IL9, IL10, IL11, IL12, IL15, IL18, IL21, and/or their respective receptor is introduced to the cell to enable cytokine signaling with or without the expression of the cytokine itself, thereby maintaining or improving cell growth, proliferation, expansion, and/or effector function with reduced risk of cytokine toxicities. In some embodiments, the introduced cytokine and/or its respective native or modified receptor for cytokine signaling are expressed on the cell surface. In some embodiments, the cytokine signaling is constitutively activated. In some embodiments, the activation of the cytokine signaling is inducible. In some embodiments, the activation of the cytokine signaling is transient and/or temporal.

FIG. 1 presents several construct designs using IL15 as an illustrative example. The transmembrane (TM) domain of any of the designs in FIG. 1 can be native to IL15 receptor, or may be modified or replaced with transmembrane domain of any other membrane bound proteins.

Design 1: IL15 and IL15Rα are co-expressed by using a self-cleaving peptide, mimicking trans-presentation of IL15, without eliminating cis-presentation of IL15.

Design 2: IL15Rα is fused to IL15 at the C-terminus through a linker, mimicking trans-presentation without eliminating cis-presentation of IL15 as well as ensuring IL15 membrane-bound.

Design 3: IL15Rα with truncated intracellular domain is fused to IL15 at the C-terminus through a linker, mimicking trans-presentation of IL15, maintaining IL15 membrane-bound, and additionally eliminating cis-presentation and/or any other potential signal transduction pathways mediated by a normal IL15R through its intracellular domain. The intracellular domain of IL15Rα has been deemed as critical for the receptor to express in the IL15 responding cells, and for the responding cells to expand and function. Such a truncated construct comprises an amino acid sequence of at least 75%, 80%, 85%, 90%, 95% or 99% identity to SEQ ID NO: 17, which may be encoded by an exemplary nucleic acid sequence represented by SEQ ID NO:18. In one embodiment of the truncated IL15/IL15Rα, the construct does not comprise the last 4 amino acid "KSRQ" of SEQ ID NO:17, and comprises an amino acid sequence of at least 75%, 80%, 85%, 90%, 95% or 99% identity to SEQ ID NO: 21.

SEQ ID NO: 17

```
MDWTWILFLVAAATRVHSGIHVFILGCFSAGLPKTEANWVNVISDLKKIED

LIQSMHIDATLYTESDVHPSCKVTAMKCFLLELQVISLESGDASIHDTVEN
```

-continued

```
LIILANNSLSSNGNVTESGCKECEELEEKNIKEFLQSFVHIVQMFINTSSG

GGSGGGGSGGGGSGGGGSGGGSLQITCPPPMSVEHADIWVKSYSLYSRERY

ICNSGFKRKAGTSSLTECVLNKATNVAHWTTPSLKCIRDPALVHQRPAPPS

TVTTAGVTPQPESLSPSGKEPAASSPSSNNTAATTAAIVPGSQLMPSKSPS

TGTTEISSHESSHGTPSQTTAKNWELTASASHQPPGVYPQGHSDTTVAIST

STVLLCGLSAVSLLACYLKSRQ
(379 a.a.; signal and linker peptides are under-
lined)
```

SEQ ID NO: 18

```
ATGGACTGGACCTGGATTCTGTTCCTGGTCGCGGCTGCAACGCGAGTCCAT

AGCGGTATCCATGTTTTTATTCTTGGGTGTTTTTCTGCTGGGCTGCCTAAG

ACCGAGGCCAACTGGGTAAATGTCATCAGTGACCTCAAGAAAATAGAAGAC

CTTATACAAAGCATGCACATTGATGCTACTCTCTACACTGAGTCAGATGTA

CATCCCTCATGCAAAGTGACGGCCATGAAATGTTTCCTCCTCGAACTTCAA

GTCATATCTCTGGAAAGTGGCGACGCGTCCATCCACGACACGGTCGAAAAC

CTGATAATACTCGCTAATAATAGTCTCTCTTCAAATGGTAACGTAACCGAG

TCAGGTTGCAAAGAGTGCGAAGAGTTGGAAGAAAAAAACATAAAGGAGTTC

CTGCAAAGTTTCGTGCACATTGTGCAGATGTTCATTAATACCTCTAGCGGC

GGAGGATCAGGTGGCGGTGGAAGCGGAGGTGGAGGCTCCGGTGGAGGAGGT

AGTGGCGGAGGTTCTCTTCAAATAACTTGTCCTCCACCGATGTCCGTAGAA

CATGCGGATATTTGGGTAAAATCCTATAGCTTGTACAGCCGAGAGCGGTAT

ATCTGCAACAGCGGCTTCAAGCGGAAGGCCGGCACAAGCAGCCTGACCGAG

TGCGTGCTGAACAAGGCCACCAACGTGGCCCACTGGACCACCCCTAGCCTG

AAGTGCATCAGAGATCCCGCCCTGGTGCATCAGCGGCCTGCCCCTCCAAGC

ACAGTGACAACAGCTGGCGTGACCCCCCAGCCTGAGAGCCTGAGCCCTTCT

GGAAAAGAGCCTGCCGCCAGCAGCCCCAGCAGCAACAATACTGCCGCCACC

ACAGCCGCCATCGTGCCTGGATCTCAGCTGATGCCCAGCAAGAGCCCTAGC

ACCGGCACCACCGAGATCAGCAGCCACGAGTCTAGCCACGGCACCCCATCT

CAGACCACCGCCAAGAACTGGGAGCTGACAGCCAGCGCCTCTCACCAGCCT

CCAGGCGTGTACCCTCAGGGCCACAGCGATACCACAGTGGCCATCAGCACC

TCCACCGTGCTGCTGTGTGGACTGAGCGCCGTGTCACTGCTGGCCTGCTAC

CTGAAGTCCAGACAGTGA
(1140 n.a.)
```

SEQ ID NO: 21

```
MDWTWILFLVAAATRVHSGIHVFILGCFSAGLPKTEANWVNVISDLKKIED

LIQSMHIDATLYTESDVHPSCKVTAMKCFLLELQVISLESGDASIHDTVEN

LIILANNSLSSNGNVTESGCKECEELEEKNIKEFLQSFVHIVQMFINTSSG

GGSGGGGSGGGGSGGGGSGGGSLQITCPPPMSVEHADIWVKSYSLYSRERY

ICNSGFKRKAGTSSLTECVLNKATNVAHWTTPSLKCIRDPALVHQRPAPPS

TVTTAGVTPQPESLSPSGKEPAASSPSSNNTAATTAAIVPGSQLMPSKSPS

TGTTEISSHESSHGTPSQTTAKNWELTASASHQPPGVYPQGHSDTTVAIST

STVLLCGLSAVSLLACYL
(375 a.a.; signal and linker peptides are under-
lined)
```

One having ordinary skill in the art would appreciate that the signal peptide and the linker sequences above are illustrative and in no way limit their variations suitable for use as a signal peptide or linker. There are many suitable signal peptide or linker sequences known and available to those in the art. The ordinary skilled in the art understands that the signal peptide and/or linker sequences may be substituted for another sequence without altering the activity of the functional peptide led by the signal peptide or linked by the linker.

Design 4: Since Design 3 construct was shown to be functional in promoting effector cell survival and expansion, demonstrating that the cytoplasmic domain of IL15Rα can be omitted without negatively impacting the autonomous feature of the effector cell equipped with IL15 in such a design, Design 4 is a construct providing another working alternative of Design 3, from which essentially the entire IL15Rα is removed except for the Sushi domain fused with IL15 at one end and a transmembrane domain on the other (mb-Sushi), optionally with a linker between the Sushi domain and the trans-membrane domain. The fused IL15/mb-Sushi is expressed at cell surface through the transmembrane domain of any membrane bound protein. With a construct such as Design 4, unnecessary signaling through IL15Rα, including cis-presentation, is eliminated when only the desirable trans-presentation of IL15 is retained. In some embodiments, the component comprising IL15 fused with Sushi domain comprises an amino acid sequence of at least 75%, 80%, 85%, 90%, 95% or 99% identity to SEQ ID NO: 19, which may be encoded by an exemplary nucleic acid sequence represented by SEQ ID NO: 20.

SEQ ID NO: 19

MDWTWILFLVAAATRVHSGIHVFILGCFSAGLPKTEANWVNVISDLKKIED
LIQSMHIDATLYTESDVHPSCKVTAMKCFLLELQVISLESGDASIHDTVEN
LIILANNSLSSNGNVTESGCKECEELEEKNIKEFLQSFVHIVQMFINTSSG
GGSGGGGSGGGGSGGGGSGGGSLQITCPPPMSVEHADIWVKSYSLYSRERY
ICNSGFKRKAGTSSLTECVLNKATNVAHWTTPSLKCIR (242 a.a.; signal and linker peptides are underlined)

SEQ ID NO: 20

ATGGACTGGACCTGGATTCTGTTCCTGGTCGCGGCTGCAACGCGAGTCCAT
AGCGGTATCCATGTTTTTATTCTTGGGTGTTTTTCTGCTGGGCTGCCTAAG
ACCGAGGCCAACTGGGTAAATGTCATCAGTGACCTCAAGAAAATAGAAGAC
CTTATACAAAGCATGCACATTGATGCTACTCTCTACACTGAGTCAGATGTA
CATCCCTCATGCAAAGTGACGGCCATGAAATGTTTCCTCCTCGAACTTCAA
GTCATATCTCTGGAAAGTGGCGACGCGTCCATCCACGACACGGTCGAAAAC
CTGATAATACTCGCTAATAATAGTCTCTCTTCAAATGGTAACGTAACCGAG
TCAGGTTGCAAAGAGTGCGAAGAGTTGGAAGAAAAAAACATAAAGGAGTTC
CTGCAAAGTTTCGTGCACATTGTGCAGATGTTCATTAATACCTCTAGCGGC
GGAGGATCAGGTGGCGGTGGAAGCGGAGGTGGAGGCTCCGGTGGAGGAGGT
AGTGGCGGAGGTTCTCTTCAAATAACTTGTCCTCCACCGATGTCCGTAGAA
CATGCGGATATTTGGGTAAAATCCTATAGCTTGTACAGCCGAGAGCGGTAT
ATCTGCAACAGCGGCTTCAAGCGGAAGGCCGGCACAAGCAGCCTGACCGAG
TGCGTGCTGAACAAGGCCACCAACGTGGCCCACTGGACCACCCCTAGCCTG
AAGTGCATCAGA (726 n.a.)

One having ordinary skill in the art would appreciate that the signal peptide and the linker sequences above are illustrative and in no way limit their variations suitable for use as a signal peptide or linker. There are many suitable signal peptide or linker sequences known and available to those in the art. The ordinary skilled in the art understands that the signal peptide and/or linker sequences may be substituted for another sequence without altering the activity of the functional peptide led by the signal peptide or linked by the linker.

Design 5: A native or modified IL15Rβ is fused to IL15 at the C-terminus through a linker, enabling constitutive signaling and maintaining IL15 membrane-bound and trans-representation.

Design 6: A native or modified common receptor γC is fused to IL15 at the C-terminus through a linker for constitutive signaling and membrane bound trans-presentation of the cytokine. The common receptor γC is also called the common gamma chain or CD132, also known as IL2 receptor subunit gamma or IL2RG. γC is a cytokine receptor sub-unit that is common to the receptor complexes for many interleukin receptors, including, but not limited to, IL2, IL4, IL7, IL9, IL15 and IL21 receptor.

Design 7: Engineered IL15Rβ that forms homodimer in absence of IL15 is useful for producing constitutive signaling of the cytokine.

In some embodiments, one or more of cytokine IL2, IL4, IL6, IL7, IL9, IL10, IL11, IL12, IL15, IL18 and IL21, and/or receptors thereof, may be introduced to iPSC using one or more of the designs in FIG. 1, and to its derivative cells upon iPSC differentiation. In some embodiments, IL2 or IL15 cell surface expression and signaling is through the construct illustrated in any one of Designs 1-7. In some embodiments, IL4, IL7, IL9, or IL21 cell surface expression and signaling is through the construct illustrated in Design 5, 6, or 7, by using either a common receptor or a cytokine specific receptor. In some embodiments, IL7 surface expression and signaling is through the construct illustrated in Design 5, 6, or 7, by using either a common receptor or a cytokine specific receptor, such as an IL4 receptor. The transmembrane (TM) domain of any of the designs in FIG. 1 can be native to respective cytokine receptor, or may be modified or replaced with transmembrane domain of any other membrane bound proteins.

In iPSCs and derivative cells therefrom comprising both CAR and exogenous cytokine and/or cytokine receptor signaling, the CAR and IL may be expressed in separate construct, or may be co-expressed in a bi-cistronic construct comprising both CAR and IL. In some further embodiments, IL15 in a form represented by any of the construct designs in FIG. 1 can be linked to either the 5' or the 3' end of a CAR expression construct through a self-cleaving 2A coding sequence, illustrated as, for example, CAR-2A-IL15 or IL15-2A-CAR. As such, the IL15 and CAR are in a single open reading frame (ORF). In one embodiment, the CAR-2A-IL15 or IL15-2A-CAR construct comprises IL15 in Design 3 of FIG. 1. In another embodiment, the CAR-2A-IL15 or IL15-2A-CAR construct comprises IL15 in Design 3 of FIG. 1. In yet another embodiment, the CAR-2A-IL15 or IL15-2A-CAR construct comprises IL15 in Design 7 of FIG. 1. When CAR-2A-IL15 or IL15-2A-CAR is expressed, the self-cleaving 2A peptide allows the expressed CAR and IL15 dissociate, and the dissociated IL15 can then be presented at cell surface. The CAR-2A-IL15 or IL15-2A-CAR bi-cistronic design allows a coordinated CAR and IL15 expression both in timing and quantity, and under the same control mechanism that may be chosen to incorporate, for example, an inducible promoter for the expression of the single ORF. Self-cleaving peptides are found in members of the Picornaviridae virus family, including aphthoviruses such as foot-and-mouth disease virus (FMDV), equine rhinitis A virus (ERAV), Thosea asigna virus (TaV) and porcine tescho virus-1 (PTV-I) (Donnelly, M L, et al, J. Gen. Virol, 82, 1027-101 (2001); Ryan, M D, et al., J. Gen. Virol., 72, 2727-2732 (2001)), and cardioviruses such as Theilovirus (e.g., Theiler's murine encephalomyelitis) and encephalomyocarditis viruses. The 2 A peptides derived from FMDV, ERAV, PTV-I, and TaV are sometimes also referred to as "F2A", "E2A", "P2A", and "T2A", respectively.

The bi-cistronic CAR-2A-IL15 or IL15-2A-CAR embodiment as disclosed herein for IL15 is also contemplated for expression of any other cytokine provided herein, for example, IL2, IL4, IL6, IL7, IL9, IL10, IL11, IL12, IL18, and IL21. In some embodiments, IL2 cell surface expression and signaling is through the construct illustrated in any of the Designs 1-7. In some other embodiments, IL4, IL7, IL9, or IL21 cell surface expression and signaling is through the construct illustrated in Design 5, 6, or 7, either using a common receptor and/or a cytokine specific receptor.

5. HLA-I- and HLA-II-Deficiency

Multiple HLA class I and class II proteins must be matched for histocompatibility in allogeneic recipients to avoid allogeneic rejection problems. Provided herein is an iPSC cell line with eliminated or substantially reduced expression of both HLA class I and HLA class II proteins. HLA class I deficiency can be achieved by functional deletion of any region of the HLA class I locus (chromosome 6p21), or deletion or reducing the expression level of HLA class-I associated genes including, not being limited to, beta-2 microglobulin (B2M) gene, TAP 1 gene, TAP 2 gene and Tapasin. For example, the B2M gene encodes a common subunit essential for cell surface expression of all HLA class I heterodimers. B2M null cells are HLA-I deficient. HLA class II deficiency can be achieved by functional deletion or reduction of HLA-II associated genes including, not being limited to, RFXANK, CIITA, RFX5 and RFXAP. CIITA is a transcriptional coactivator, functioning through activation of the transcription factor RFX5 required for class II protein expression. CIITA null cells are HLA-II deficient. Provided herein is an iPSC line and its derivative cells with both B2M and CIITA knocked out, wherein the obtained derivative effector cells enable allogeneic cell therapies by eliminating the need for MHC (major histocompatibility complex) matching, and avoid recognition and killing by host (allogeneic) T cells.

For some cell types, a lack of class I expression leads to lysis by NK cells. To overcome this "missing self" response, HLA-G may be optionally knocked in to avoid NK cell recognition and killing of the HLA-I and HLA-II deficient effector cells derived from an engineered iPSC. In one embodiment, the HLA-I and HLA-II deficient iPSC and its derivative cells further comprise CD38 knock-out, and optionally one or more of hnCD16, CAR and IL, without adversely impacting the differentiation potential of the iPSC and function of the derived effector cells including derivative T and NK cells.

6. Genetically Engineered iPSC Line and Derivative Cells Provided Herein

In light of the above, the present application provides a $CD38^{-/-}$ (also referred to as "CD38 null" or CD38 knockout herein) iPSC, cell line cell, or a population thereof, and derived functional derivative cells comprising CD38 knockout obtained from differentiation of the $CD38^{-/-}$ iPSC. In some embodiments, the functional derivative cells are hematopoietic cells include, but are not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages. In some embodiments, the functional derivative hematopoietic cells comprise effector cells such as T, NK, and regulatory cells.

Further provided herein is an iPSC comprising a CD38 knockout, and a polynucleotide encoding a high affinity non-cleavable CD16 (hnCD16), wherein the iPSC is capable of directed differentiation to produce functional derivative hematopoietic cells. In some embodiments, when an anti-CD38 antibody is used to induce the hnCD16 mediated enhanced ADCC, the iPSC and/or its derivative effector cells can target the CD38 expressing (tumor) cells without causing effector cell elimination, i.e., reduction or depletion of CD38 expressing effector cells, thereby increasing the iPSC and its effector cell persistence and/or survival. In some embodiments, the effector cell has increased persistence and/or survival in vivo in the presence of anti-CD38 therapeutic agents, which may be an anti-CD38 antibody or a CAR binding CD38. In some embodiments, the effector cells comprise T cells. iPSC derived T cells comprising CD38 null and hnCD16 experience reduced cell depletion in the presence of anti-CD38 antibodies or anti-CD38 CARs; have acquired ADCC, providing an additional mechanism for tumor killing mediated by T cells. In some embodiments, the effector cells comprise NK cells. iPSC derived NK cells comprising CD38 null and hnCD16 have enhanced cytotoxicity and have reduced NK cell fractricide in the presence of anti-CD38 antibodies or anti-CD38 CARs.

An iPSC comprising a CD38 knockout, and a polynucleotide encoding a target specific chimeric antigen receptor (CAR) is provided herein, wherein the iPSC is capable of directed differentiation to produce functional derivative effector cells. In one embodiment, the CAR comprised in the iPSC and its derivative effector cells comprising CD38 knockout targets tumor cell surface protein CD38, yet the CD38-CAR does not lead to elimination of iPSCs and/or its derivative effector cells with CD38 knocked out. In some embodiments, the CAR comprised in the iPSC and its derivative effector cells comprising CD38 knockout does not target CD38. In some embodiments, the CAR expressing-, CD38 null-derivative effector cells can be used with an anti-CD38 antibody to induce ADCC without causing effector cell elimination, thereby increasing the iPSC and its effector cell persistence and/or survival. In some embodiments, the effector cell has increased persistence and/or survival in vivo in a combinational treatment.

Additionally provided is an iPSC comprising a CD38 knockout, and a polynucleotide encoding at least one exogenous cytokine and/or its receptor (IL) to enable cytokine signaling contributing to cell survival, persistence and/or expansion, wherein the iPSC line is capable of directed differentiation to produce functional derivative hematopoietic cells having improved survival, persistency, expansion, and effector cell function. The exogenously introduced cytokine signaling(s) comprise the signaling of any one, or two, or more of IL2, IL4, IL6, IL7, IL9, IL10, IL11, IL12, IL15, IL18, and IL21. In some embodiments, the introduced partial or full peptide of cytokine and/or its respective receptor for cytokine signaling are expressed on the cell surface. In some embodiments, the cytokine signaling is constitutively activated. In some embodiments, the activation of the cytokine signaling is inducible. In some embodiments, the activation of the cytokine signaling is transient and/or temporal. In some embodiments, the transient/temporal expression of a cell surface cytokine/cytokine receptor is through a retrovirus, Sendai virus, an adenovirus, an episome, mini-circle, or RNAs including mRNA. In some embodiments, the exogenous cell surface cytokine and/or receptor comprised in the CD38$^{-/-}$ iPSC or derivative cells thereof enables IL7 signaling. In some embodiments, the exogenous cell surface cytokine and/or receptor comprised in the CD38$^{-/-}$ iPSC or derivative cells thereof enables IL10 signaling. In some embodiments, the exogenous cell surface cytokine and/or receptor comprised in the CD38$^{-/-}$ iPSC or derivative cells thereof enables IL15 signaling. In some embodiments of said CD38$^{-/-}$ IL iPSC, the IL15 expression is through construct 3 of FIG. 1. In some embodiments of said CD38$^{-/-}$ IL iPSC, the IL15 expression is through construct 4 of FIG. 1. Said CD38$^{-/-}$ IL iPSC and its derivative cells of the above embodiments are capable of maintaining or improving cell growth, proliferation, expansion, and/or effector function autonomously without contacting additionally supplied soluble cytokines in vitro or in vivo. In some embodiments, CD38$^{-/-}$ IL iPSC and its derivative effector cells can be used with an anti-CD38 antibody to induce ADCC without causing effector cell elimination, thereby synergistically increasing the iPSC and its effector cell persistence and/or survival.

Also provided is an iPSC comprising a CD38 knockout, a B2M knockout and a CIITA knockout, and optionally, a polynucleotide encoding HLA-G, wherein the iPSC is capable of directed differentiation to produce functional derivative hematopoietic cells. Said CD38$^{-/-}$ B2M$^{-/-}$ iPSC and its derivative effector cells are both HLA-I and HLA-II deficient, and can be used with an anti-CD38 antibody to induce ADCC without causing effector cell elimination, thereby increasing the iPSC and its effector cell persistence and/or survival. In some embodiments, the effector cell has increased persistence and/or survival in vivo.

In view of the above, provided herein include an iPSC comprising a CD38 knockout, and optionally one, two, three or all four of: hnCD16, CAR, an exogenous cytokine/receptor, and B2M/CIITA knockout; wherein when B2M is knocked out, a polynucleotide encoding HLA-G is optionally introduced, and wherein the iPSC is capable of directed differentiation to produce functional derivative hematopoietic cells. Also included in this application are functional iPSC derivative hematopoietic cells comprising a CD38 knockout, and optionally one, two, three or all four of: hnCD16, B2M/CIITA knockout, CAR, and an exogenous cytokine/receptor; wherein when B2M is knocked out, a polynucleotide encoding HLA-G is optionally introduced, and wherein the derivative hematopoietic cells include, but are not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages.

Another aspect provided herein includes an iPSC or iPSC derived cells comprising a truncated fusion protein of IL15 and IL15Rα, wherein the fusion protein does not comprise an intracellular domain. Shown as "IL15Rα(ΔICD) fusion" and "IL5/mb-Sushi" in FIG. 1, these embodiments are further collectively abbreviated as IL15Δ in Table 1 and throughout this application. In some embodiments, the truncated IL15/IL15Rα fusion protein lacking intracellular domain comprises an amino acid sequence of at least 75%, 80%, 85%, 90%, 95% or 99% identity to SEQ ID NOs: 17, 19 or 21. In some embodiments, the truncated IL15/IL15Rα fusion protein lacking intracellular domain comprises an amino acid sequence of SEQ ID NO: 17. In some embodiments, the truncated IL15/IL15Rα fusion protein lacking intracellular domain comprises an amino acid sequence of SEQ ID NO: 19. In some embodiments, the truncated IL15/IL15Rα fusion protein lacking intracellular domain comprises an amino acid sequence of SEQ ID NO: 21. In yet some other embodiments, the iPSC or iPSC derived cells comprising a truncated IL15/IL15Rα fusion protein lacking intracellular domain (IL15Δ) further comprise one or more of: CD38 knockout, hnCD16, CAR, an exogenous cytokine/receptor, and B2M/CIITA knockout; wherein when B2M is knocked out, a polynucleotide encoding HLA-G is optionally introduced, and wherein the iPSC is capable of directed differentiation to produce functional derivative hematopoietic cells, and wherein the derivative hematopoietic cells include, but are not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages.

As such, the present application provides iPSCs and its functional derivative hematopoietic cells, which comprise any one of the following genotypes in Table 1. Unless specified as IL15Δ, which is detailed above as a truncated fusion protein of IL15 and IL15Rα but without an intracellular domain, "IL", as provided in Table 1 stands for one of IL2, IL4, IL6, IL7, IL9, IL10, IL11, IL12, IL15, IL18, and IL21, depending on which specific cytokine/receptor expression is selected. Further, when iPSCs and its functional derivative hematopoietic cells have a genotype comprising both CAR and IL, the CAR and IL are comprised in a bi-cistronic expression cassette comprising a 2A sequence. As comparison, in some other embodiments, CAR and IL are in separate expression cassettes comprised in iPSCs and its functional derivative hematopoietic cells. In one particular embodiment, comprised in the iPSCs and its functional derivative effector cells expressing both CAR and IL, is IL15 in a construct 3 or 4 of FIG. 1, wherein the IL15 construct is comprised in an expression cassette with, or separate from, the CAR.

TABLE 1

| Applicable Genotypes of the Cells Provided: | |
|---|---|
| 1 | CD38$^{-/-}$ |
| 2 | CD38$^{-/-}$ hnCD16 |
| 3 | CD38$^{-/-}$ CAR |
| 4 | CD38$^{-/-}$ IL |
| 5 | CD38$^{-/-}$ CAR IL |
| 6 | CD38$^{-/-}$ hnCD16 CAR |
| 7 | CD38$^{-/-}$ hnCD16 IL |
| 8 | CD38$^{-/-}$ hnCD16 CAR IL |
| 9 | CD38$^{-/-}$ B2M$^{-/-}$CIITA$^{-/-}$ |
| 10 | CD38$^{-/-}$ B2M$^{-/-}$ CIITA$^{-/-}$ HLA-G |
| 11 | CD38$^{-/-}$ hnCD16 B2M$^{-/-}$ CIITA$^{-/-}$ |
| 12 | CD38$^{-/-}$ hnCD16 B2M$^{-/-}$ CIITA$^{-/-}$HLA-G |
| 13 | CD38$^{-/-}$ B2M$^{-/-}$ CIITA$^{-/-}$ CAR |
| 14 | CD38$^{-/-}$ B2M$^{-/-}$ CIITA$^{-/-}$ HLA-G CAR |
| 15 | CD38$^{-/-}$ B2M$^{-/-}$ CIITA$^{-/-}$ IL |
| 16 | CD38$^{-/-}$ B2M$^{-/-}$ CIITA$^{-/-}$ HLA-G IL |
| 17 | CD38$^{-/-}$ hnCD16 B2M$^{-/-}$ CIITA$^{-/-}$CAR |
| 18 | CD38$^{-/-}$ hnCD16 B2M$^{-/-}$ CIITA$^{-/-}$HLA-G CAR |
| 19 | CD38$^{-/-}$ hnCD16 B2M$^{-/-}$ CIITA$^{-/-}$ IL |

TABLE 1-continued

| Applicable Genotypes of the Cells Provided: | |
|---|---|
| 20 | CD38$^{-/-}$ hnCD16 B2M$^{-/-}$ CIITA$^{-/-}$ HLA-G IL |
| 21 | CD38$^{-/-}$ B2M$^{-/-}$ CIITA$^{-/-}$ CAR IL |
| 22 | CD38$^{-/-}$ B2M$^{-/-}$ CIITA$^{-/-}$ HLA-G CAR IL |
| 23 | CD38$^{-/-}$ hnCD16 B2M$^{-/-}$ CIITA$^{-/-}$ CAR IL |
| 24 | CD38$^{-/-}$ hnCD16 B2M$^{-/-}$ CIITA$^{-/-}$ HLA-G CAR IL |
| 25 | IL15Δ |
| 26 | IL15Δ hnCD16 |
| 27 | IL15Δ CAR |
| 28 | IL15Δ hnCD16 CAR |
| 29 | IL15Δ hnCD16 |
| 30 | IL15Δ hnCD16 CAR |
| 31 | IL15Δ B2M$^{-/-}$CIITA$^{-/-}$ |
| 32 | IL15Δ B2M$^{-/-}$ CIITA$^{-/-}$ HLA-G |
| 33 | IL15Δ hnCD16 B2M$^{-/-}$ CIITA$^{-/-}$ |
| 34 | IL15Δ hnCD16 B2M$^{-/-}$ CIITA$^{-/-}$HLA-G |
| 35 | IL15Δ B2M$^{-/-}$ CIITA$^{-/-}$ CAR |
| 36 | IL15Δ B2M$^{-/-}$ CIITA$^{-/-}$ HLA-G CAR |
| 37 | IL15Δ B2M$^{-/-}$ CIITA$^{-/-}$ |
| 38 | IL15Δ B2M$^{-/-}$ CIITA$^{-/-}$ HLA-G |
| 39 | IL15Δ hnCD16 B2M$^{-/-}$ CIITA$^{-/-}$CAR |
| 40 | IL15Δ hnCD16 B2M$^{-/-}$ CIITA$^{-/-}$HLA-G CAR |
| 41 | IL15Δ hnCD 16 B2M$^{-/-}$ CIITA$^{-/-}$ |
| 42 | IL15Δ hnCD16 B2M$^{-/-}$ CIITA$^{-/-}$ HLA-G |
| 43 | IL15Δ B2M$^{-/-}$ CIITA$^{-/-}$ CAR |
| 44 | IL15Δ B2M$^{-/-}$ CIITA$^{-/-}$ HLA-G CAR |
| 45 | IL15Δ hnCD16 B2M$^{-/-}$ CIITA$^{-/-}$ CAR |
| 46 | IL15Δ hnCD16 B2M$^{-/-}$ CIITA$^{-/-}$ HLA-G CAR |

7. Additional Modifications

In some embodiments, the iPSC, and its derivative effector cells comprising any one of the genotypes in Table 1 may additionally comprise deletion or reduced expression in at least one of TAP1, TAP2, Tapasin, NLRC5, PD1, LAG3, TIM3, RFXANK, RFX5, RFXAP, and any gene in the chromosome 6p21 region; or introduced or increased expression in at least one of HLA-E, 41BBL, CD3ζ, CD4, CD8, CD47, CD113, CD131, CD137, CD80, PDL1, $A_{2A}$R, TCR, Fc receptor, an engager, and surface triggering receptor for coupling with bi-, multi-specific or universal engagers.

Bi- or multi-specific engagers are fusion proteins consisting of two or more single-chain variable fragments (scFvs) of different antibodies, with at least one scFv binds to an effector cell surface molecule, and at least another to a tumor cell via a tumor specific surface molecule. The exemplary effector cell surface molecules, or surface triggering receptor, that can be used for bi- or multi-specific engager recognition, or coupling, include, but are not limited to, CD3ζ, CD28, CD5, CD16, NKG2D, CD64, CD32, CD89, NKG2C, and a chimeric Fc receptor as disclosed herein. In some embodiments, the CD16 expressed on the surface of effector cells for engager recognition is a hnCD16, comprising CD16 (containing F176V and optionally S197P) or CD64 extracellular domain, and native or non-native transmembrane, stimulatory and/or signaling domains as described in section I.2. In some embodiments, the CD16 expressed on the surface of effector cells for engager recognition is a hnCD16 based chimeric Fc receptor (CFcR). In some embodiments, the hnCD16 based CFcR comprises a transmembrane domain of NKG2D, a stimulatory domain of 2B4, and a signaling domain of CD3ζ; wherein the extracellular domain of the hnCD16 is derived from a full length or partial sequence of the extracellular domain of CD64 or CD16; and wherein the extracellular domain of CD16 comprises F176V and optionally S197P. The exemplary tumor cell surface molecules for bi- or multi-specific engager recognition include, but are not limited to, B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, ROR1. In one embodiment, the bispecific antibody is CD3-CD19. In another embodiment, the bispecific antibody is CD16-CD30 or CD64-CD30. In another embodiment, the bispecific antibody is CD16-BCMA or CD64-BCMA. In still another embodiment, the bispecific antibody is CD3-CD33. In yet another embodiment, the bispecific antibody further comprises a linker between the effector cell and tumor cell antigen binding domains, for example, a modified IL15 as a linker for effector NK cells to facilitate effector cell expansion (called TriKE, or Trispecific Killer Engager, in some publications). In one embodiment, the TriKE is CD16-IL15-EPCAM or CD64-IL15-EPCAM. In another embodiment, the TriKE is CD16-IL15-CD33 or CD64-IL15-CD33. In yet another embodiment, the TriKE is NKG2C-IL15-CD33.

In some embodiments, the surface triggering receptor for bi- or multi-specific engager could be endogenous to the effector cells, sometimes depending on the cell types. In some other embodiments, one or more exogenous surface triggering receptors could be introduced to the effector cells using the methods and compositions provided herein, i.e., through additional engineering of an iPSC comprising a genotype listed in Table 1, then directing the differentiation of the iPSC to T, NK or any other effector cells comprising the same genotype and the surface triggering receptor as the source iPSC.

8. Antibodies for Immunotherapy

In some embodiments, in addition to the genomically engineered effector cells as provided herein, additional therapeutic agent comprising an antibody, or an antibody fragment that targets an antigen associated with a condition, a disease, or an indication may be used with these effector cells in a combinational therapy. In some embodiments, the antibody is a monoclonal antibody. In some embodiments, the antibody is a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the administered iPSC derived effector cells to enhance their killing ability. In some embodiments, the antibodies suitable for combinational treatment as an additional therapeutic agent to the administered iPSC derived effector cells include, but are not limited to, anti-CD20 (rituximab, veltuzumab, ofatumumab, ublituximab, ocaratuzumab, obinutuzumab), anti-HER2 (trastuzumab, pertuzumab), anti-CD52 (alemtuzumab), anti-EGFR (certuximab), anti-GD2 (dinutuximab), anti-PDL1 (avelumab), anti-CD38 (daratumumab, isatuximab, MOR202), anti-CD123 (7G3, CSL362), anti-SLAMF7 (elotuzumab), and their humanized or Fc modified variants or fragments or their functional equivalents and biosimilars. In some embodiments, the iPSC derived effector cells comprise hematopoietic lineage cells comprising a genotype listed in Table 1. In some embodiments, the iPSC derived effector cells comprise NK cells comprising a genotype listed in Table 1. In some embodiments, the iPSC derived effector cells comprise T cells comprising a genotype listed in Table 1. In some embodiments of a combination useful for treating liquid or solid tumors, the combination comprises iPSC derived NK or T cells comprising at least CD38 null, and an anti-CD38 antibody. In one embodiment, the combination comprises iPSC derived NK cells comprising CD38 null and hnCD16; and one of the anti-CD38 antibodies, daratumumab, isatuximab, and MOR202. In one embodiment, the combination comprises iPSC derived NK cells comprising CD38 null and hnCD16, and daratumumab. In some further embodiments, the iPSC derived NK cells comprised in the combination with daratumumab comprise CD38 null, hnCD16, IL15, and a CAR targeting CD38 or one of CD19, BCMA, CD20, CD22, CD123, HER2, CD52, EGFR, GD2, and PDL1; wherein the IL15 is co- or separately expressed with the CAR; and IL15 is in any one of the forms presented in constructs 1 to 7 of FIG. 1. In some particular embodiments, IL15 is in a form of construct 3, 4, or 7 when it is co- or separately expressed with the CAR.

9. Checkpoint Inhibitors

Checkpoints are cell molecules, often cell surface molecules, capable of suppressing or downregulating immune responses when not inhibited. It is now clear that tumors co-opt certain immune-checkpoint pathways as a major mechanism of immune resistance, particularly against T cells that are specific for tumor antigens. Checkpoint inhibitors (CI) are antagonists capable of reducing checkpoint gene expression or gene products, or decreasing activity of checkpoint molecules, thereby block inhibitory checkpoints, restoring immune system function. The development of checkpoint inhibitors targeting PD1/PDL1 or CTLA4 has transformed the oncology landscape, with these agents providing long term remissions in multiple indications. However, many tumor subtypes are resistant to checkpoint blockade therapy, and relapse remains a significant concern. One aspect of the present application provides a therapeutic approach to overcome CI resistance by including genomically-engineered functional derivative cells as provided in a combination therapy with CI. In one embodiment of the combination therapy, the derivative cells are NK cells. In another embodiment of the combination therapy, the derivative cells are T cells. In addition to exhibiting direct antitumor capacity, the derivative NK cells provided herein have been shown to resist PDL1-PD1 mediated inhibition, and to have the ability to enhance T cell migration, to recruit T cells to the tumor microenvironment, and to augment T cell activation at the tumor site. Therefore, the tumor infiltration of T cell facilitated by the functionally potent genomically-engineered derivative NK cells indicate that said NK cells are capable of synergizing with T cell targeted immunotherapies, including the checkpoint inhibitors, to relieve local immunosuppression and to reduce tumor burden.

In one embodiment, the derived NK cell for checkpoint inhibitor combination therapy comprises a CD38 knockout, and optionally one, two, three or all four of: hnCD16 expression, B2M/CIITA knockout, CAR expression, and an exogenous cell surface cytokine and/or receptor expression; wherein when B2M is knocked out, a polynucleotide encoding HLA-G is optionally included. In some embodiments, the derivative NK cell comprises any one of the genotypes listed in Table 1. In some embodiments, the above derivative NK cell additionally comprises deletion or reduced expression in at least one of TAP1, TAP2, Tapasin, NLRC5, PD1, LAG3, TIM3, RFXANK, RFX5, RFXAP, and any gene in the chromosome 6p21 region; or introduced or increased expression in at least one of HLA-E, 41BBL, CD3ζ, CD4, CD8, CD47, CD113, CD131, CD137, CD80, PDL1, $A_{2A}R$, CAR, TCR, Fc receptor, an engager, and surface triggering receptor for coupling with bi-, multi-specific or universal engagers.

In another embodiment, the derived T cell for checkpoint inhibitor combination therapy comprises a CD38 knockout, and optionally one, two, three or all four of: hnCD16 expression, B2M/CIITA knockout, CAR expression, and an exogenous cell surface cytokine and/or receptor expression; wherein when B2M is knocked out, a polynucleotide encoding HLA-G is optionally included. In some embodiments, the derivative T cell comprises any one of the genotypes listed in Table 1. In some embodiments, the above derivative T cell additionally comprises deletion or reduced expression in at least one of TAP1, TAP2, Tapasin, NLRC5, PD1, LAG3, TIM3, RFXANK, RFX5, RFXAP, and any gene in the chromosome 6p21 region; or introduced or increased expression in at least one of HLA-E, 41BBL, CD3ζ, CD4, CD8, CD47, CD113, CD131, CD137, CD80, PDL1, $A_{2A}R$, CAR, TCR, Fc receptor, an engager, and surface triggering receptor for coupling with bi-, multi-specific or universal engagers.

Above said derivative NK or T cell is obtained from differentiating an iPSC clonal line comprising a CD38 knockout, and optionally one, two, three or all four of: hnCD16 expression, B2M/CIITA knockout, CAR expression, and an exogenous cell surface cytokine expression; wherein when B2M is knocked out, a polynucleotide encoding HLA-G is optionally introduced. In some embodiments, above said iPSC clonal line further comprises deletion or reduced expression in at least one of TAP1, TAP2, Tapasin, NLRC5, PD1, LAG3, TIM3, RFXANK, RFX5, RFXAP, and any gene in the chromosome 6p21 region; or introduced or increased expression in at least one of HLA-E, 41BBL, CD3ζ, CD4, CD8, CD47, CD113, CD131, CD137, CD80, PDL1, $A_{2A}R$, CAR, TCR, Fc receptor, an engager, and surface triggering receptor for coupling with bi-, multi-specific or universal engagers.

Suitable checkpoint inhibitors for combination therapy with the derivative NK or T cells as provided herein include, but are not limited to, antagonists of PD-1 (Pdcdl, CD279), PDL-1 (CD274), TIM-3 (Havcr2), TIGIT (WUCAM and Vstm3), LAG-3 (Lag3, CD223), CTLA-4 (Ctla4, CD152), 2B4 (CD244), 4-1BB (CD137), 4-1BBL (CD137L), A2aR, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR (for example, 2DL1, 2DL2, 2DL3, 3DL1, and 3DL2).

In some embodiments, the antagonist inhibiting any of the above checkpoint molecules is an antibody. In some embodiments, the checkpoint inhibitory antibodies may be murine antibodies, human antibodies, humanized antibodies, a camel Ig, a shark heavy-chain-only antibody (VNAR), Ig NAR, chimeric antibodies, recombinant antibodies, or antibody fragments thereof. Non-limiting examples of antibody fragments include Fab, Fab', F(ab)'2, F(ab)'3, Fv, single chain antigen binding fragments (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody, which may be more cost-effective to produce, more easily used, or more sensitive than the whole antibody. In some embodiments, the one, or two, or three, or more checkpoint inhibitors comprise at least one of atezolizumab (anti-PDL1 mAb), avelumab (anti-PDL1 mAb), durvalumab (anti-PDL1 mAb), tremelimumab (anti-CTLA4 mAb), ipilimumab (anti-CTLA4 mAb), IPH4102 (anti-KIR), IPH43 (anti-MICA), IPH33 (anti-TLR3), lirimumab (anti-KIR), monalizumab (anti-NKG2A), nivolumab (anti-PD1 mAb), pembrolizumab (anti-PD1 mAb), and any derivatives, functional equivalents, or biosimilars thereof.

In some embodiments, the antagonist inhibiting any of the above checkpoint molecules is microRNA-based, as many miRNAs are found as regulators that control the expression of immune checkpoints (Dragomir et al., Cancer Biol Med. 2018, 15(2):103-115). In some embodiments, the checkpoint antagonistic miRNAs include, but are not limited to, miR-28, miR-15/16, miR-138, miR-342, miR-20b, miR-21, miR-130b, miR-34a, miR-197, miR-200c, miR-200, miR-17-5p, miR-570, miR-424, miR-155, miR-574-3p, miR-513, and miR-29c.

Some embodiments of the combination therapy with the provided derivative NK or T cells comprise at least one checkpoint inhibitor to target at least one checkpoint molecule; wherein the derivative cells have a genotype listed in Table 1. Some other embodiments of the combination therapy with the provided derivative NK or T cells comprise two, three or more checkpoint inhibitors such that two, three, or more checkpoint molecules are targeted. In some embodiments of the combination therapy comprising at least one checkpoint inhibitor and the derivative cells having a genotype listed in Table 1, said checkpoint inhibitor is an antibody, or a humanized or Fc modified variant or fragment, or a functional equivalent or biosimilar thereof, and said checkpoint inhibitor is produced by the derivative cells by expressing an exogenous polynucleotide sequence encoding said antibody, or a fragment or variant thereof. In some embodiments, the exogenous polynucleotide sequence encoding the antibody, or a fragment or a variant thereof that inhibits a checkpoint is co-expressed with a CAR, either in separate constructs or in a bi-cistronic construct comprising both CAR and the sequence encoding the antibody, or the fragment thereof. In some further embodiments, the sequence encoding the antibody or the fragment thereof can be linked to either the 5' or the 3' end of a CAR expression construct through a self-cleaving 2A coding sequence, illustrated as, for example, CAR-2A-CI or CI-2A-CAR. As such, the coding sequences of the checkpoint inhibitor and the CAR are in a single open reading frame (ORF). When the checkpoint inhibitor is delivered, expressed and secreted as a payload by the derivative effector cells capable of infiltrating the tumor microenvironment (TME), it counteracts the inhibitory checkpoint molecule upon engaging the TME, allowing activation of the effector cells by activating modalities such as CAR or activating receptors. In some embodiments, the checkpoint inhibitor co-expressed with CAR inhibits at least one of the checkpoint molecules: PD-1, PDL-1, TIM-3, TIGIT, LAG-3, CTLA-4, 2B4, 4-1BB, 4-1BBL, A2aR, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR. In some embodiments, the checkpoint inhibitor co-expressed with CAR in a derivative cell having a genotype listed in Table 1 is selected from a group comprising atezolizumab, avelumab, durvalumab, tremelimumab, ipilimumab, IPH4102, IPH43, IPH33, lirimumab, monalizumab, nivolumab, pembrolizumab, and their humanized, or Fc modified variants, fragments and their functional equivalents or biosimilars. In some embodiments, the checkpoint inhibitor co-expressed with CAR is atezolizumab, or its humanized, or Fc modified variants, fragments or their functional equivalents or biosimilars. In some other embodiments, the checkpoint inhibitor co-expressed with CAR is nivolumab, or its humanized, or Fc modified variants, fragments or their functional equivalents or biosimilars. In some other embodiments, the checkpoint inhibitor co-expressed with CAR is pembrolizumab, or its humanized, or Fc modified variants, fragments or their functional equivalents or biosimilars.

In some other embodiments of the combination therapy comprising the derivative cells provided herein and at least one antibody inhibiting a checkpoint molecule, said antibody is not produced by, or in, the derivative cells and is additionally administered before, with, or after the administering of the derivative cells having a genotype listed in Table 1. In some embodiments, the administering of one, two, three or more checkpoint inhibitors in a combination therapy with the provided derivative NK or T cells are simultaneous or sequential. In one embodiment of the combination treatment comprising derived NK cells or T cells having a genotype listed in Table 1, the checkpoint inhibitor included in the treatment is one or more of atezolizumab, avelumab, durvalumab, tremelimumab, ipilimumab, IPH4102, IPH43, IPH33, lirimumab, monalizumab, nivolumab, pembrolizumab, and their humanized or Fc modified variants, fragments and their functional equivalents or biosimilars. In some embodiments of the combination treatment comprising derived NK cells or T cells having a genotype listed in Table 1, the checkpoint inhibitor included in the treatment is atezolizumab, or its humanized or Fc modified variant, fragment and its functional equivalent or biosimilar. In some embodiments of the combination treatment comprising derived NK cells or T cells having a genotype listed in Table 1, the checkpoint inhibitor included in the treatment is nivolumab, or its humanized or Fc modified variant, fragment or its functional equivalent or biosimilar. In some embodiments of the combination treatment comprising derived NK cells or T cells having a genotype listed in Table 1, the checkpoint inhibitor included in the treatment is pembrolizumab, or its humanized or Fc modified variant, fragment or its functional equivalent or biosimilar.

II. Methods for Targeted Genome Editing at Selected Locus in iPSCs

Genome editing, or genomic editing, or genetic editing, as used interchangeably herein, is a type of genetic engineering in which DNA is inserted, deleted, and/or replaced in the genome of a targeted cell. Targeted genome editing (interchangeable with "targeted genomic editing" or "targeted genetic editing") enables insertion, deletion, and/or substitution at pre-selected sites in the genome. When an endogenous sequence is deleted at the insertion site during targeted editing, an endogenous gene comprising the affected sequence may be knocked-out or knocked-down due to the sequence deletion. Therefore, targeted editing may also be used to disrupt endogenous gene expression with precision. Similarly used herein is the term "targeted integration," referring to a process involving insertion of one or more exogenous sequences, with or without deletion of an endogenous sequence at the insertion site. In comparison, randomly integrated genes are subject to position effects and silencing, making their expression unreliable and unpredictable. For example, centromeres and sub-telomeric regions are particularly prone to transgene silencing. Reciprocally, newly integrated genes may affect the surrounding endogenous genes and chromatin, potentially altering cell behavior or favoring cellular transformation. Therefore, inserting exogenous DNA in a pre-selected locus such as a safe harbor locus, or genomic safe harbor (GSH) is important for safety, efficiency, copy number control, and for reliable gene response control.

Targeted editing can be achieved either through a nuclease-independent approach, or through a nuclease-dependent approach. In the nuclease-independent targeted editing approach, homologous recombination is guided by homologous sequences flanking an exogenous polynucleotide to be inserted, through the enzymatic machinery of the host cell.

Alternatively, targeted editing could be achieved with higher frequency through specific introduction of double strand breaks (DSBs) by specific rare-cutting endonucleases. Such nuclease-dependent targeted editing utilizes DNA repair mechanisms including non-homologous end joining (NHEJ), which occurs in response to DSBs. Without a donor vector containing exogenous genetic material, the NHEJ often leads to random insertions or deletions (in/dels) of a small number of endogenous nucleotides. In comparison, when a donor vector containing exogenous genetic material flanked by a pair of homology arms is present, the exogenous genetic material can be introduced into the genome during homology directed repair (HDR) by homologous recombination, resulting in a "targeted integration."

Available endonucleases capable of introducing specific and targeted DSBs include, but not limited to, zinc-finger nucleases (ZFN), transcription activator-like effector nucleases (TALEN), RNA-guided CRISPR (Clustered Regular Interspaced Short Palindromic Repeats) systems. Additionally, DICE (dual integrase cassette exchange) system utilizing phiC31 and Bxb1 integrases is also a promising tool for targeted integration.

ZFNs are targeted nucleases comprising a nuclease fused to a zinc finger DNA binding domain. By a "zinc finger DNA binding domain" or "ZFBD" it is meant a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, $C_2H_2$ zinc fingers, $C_3H$ zinc fingers, and $C_4$ zinc fingers. A "designed" zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A "selected" zinc finger domain is a domain not found in nature whose production results primarily from an empirical process such as phage display, interaction trap or hybrid selection. ZFNs are described in greater detail in U.S. Pat. Nos. 7,888,121 and 7,972,854, the complete disclosures of which are incorporated herein by reference. The most recognized example of a ZFN in the art is a fusion of the FokI nuclease with a zinc finger DNA binding domain.

A TALEN is a targeted nuclease comprising a nuclease fused to a TAL effector DNA binding domain. By "transcription activator-like effector DNA binding domain", "TAL effector DNA binding domain", or "TALE DNA binding domain" it is meant the polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940, which is herein incorporated by reference. The most recognized example of a TALEN in the art is a fusion polypeptide of the FokI nuclease to a TAL effector DNA binding domain.

Another example of a targeted nuclease that finds use in the subject methods is a targeted Spo11 nuclease, a polypeptide comprising a Spo11 polypeptide having nuclease activity fused to a DNA binding domain, e.g. a zinc finger DNA binding domain, a TAL effector DNA binding domain, etc. that has specificity for a DNA sequence of interest. See, for example, U.S. Application No. 61/555,857, the disclosure of which is incorporated herein by reference.

Additional examples of targeted nucleases suitable for the present invention include, but not limited to Bxb1, phiC31, R4, PhiBT1, and Wβ/SPBc/TP901-1, whether used individually or in combination.

Other non-limiting examples of targeted nucleases include naturally occurring and recombinant nucleases; CRISPR related nucleases from families including cas, cpf, cse, csy, csn, csd, cst, csh, csa, csm, and cmr; restriction endonucleases; meganucleases; homing endonucleases, and the like.

As an exemplary example, CRISPR/Cas9 requires two major components: (1) a Cas9 endonuclease and (2) the crRNA-tracrRNA complex. When co-expressed, the two components form a complex that is recruited to a target DNA sequence comprising PAM and a seeding region near PAM. The crRNA and tracrRNA can be combined to form a chimeric guide RNA (gRNA) to guide Cas9 to target selected sequences. These two components can then be delivered to mammalian cells via transfection or transduction.

DICE mediated insertion uses a pair of recombinases, for example, phiC31 and Bxb 1, to provide unidirectional integration of an exogenous DNA that is tightly restricted to each enzymes' own small attB and attP recognition sites. Because these target att sites are not naturally present in mammalian genomes, they must be first introduced into the genome, at the desired integration site. See, for example, U.S. Application Publication No. 2015/0140665, the disclosure of which is incorporated herein by reference.

One aspect of the present invention provides a construct comprising one or more exogenous polynucleotides for targeted genome integration. In one embodiment, the construct further comprises a pair of homologous arm specific to a desired integration site, and the method of targeted integration comprises introducing the construct to cells to enable site specific homologous recombination by the cell host enzymatic machinery. In another embodiment, the method of targeted integration in a cell comprises introducing a construct comprising one or more exogenous polynucleotides to the cell and introducing a ZFN expression cassette comprising a DNA-binding domain specific to a desired integration site to the cell to enable a ZFN-mediated insertion. In yet another embodiment, the method of targeted integration in a cell comprises introducing a construct comprising one or more exogenous polynucleotides to the cell and introducing a TALEN expression cassette comprising a DNA-binding domain specific to a desired integration site to the cell to enable a TALEN-mediated insertion. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration.

Promising sites for targeted integration include, but are not limited to, safe harbor loci, or genomic safe harbor (GSH), which are intragenic or extragenic regions of the human genome that, theoretically, are able to accommodate predictable expression of newly integrated DNA without adverse effects on the host cell or organism. A useful safe harbor must permit sufficient transgene expression to yield desired levels of the vector-encoded protein or non-coding RNA. A safe harbor also must not predispose cells to malignant transformation nor alter cellular functions. For an integration site to be a potential safe harbor locus, it ideally needs to meet criteria including, but not limited to: absence of disruption of regulatory elements or genes, as judged by sequence annotation; is an intergenic region in a gene dense area, or a location at the convergence between two genes transcribed in opposite directions; keep distance to minimize the possibility of long-range interactions between vector-encoded transcriptional activators and the promoters of adjacent genes, particularly cancer-related and microRNA genes; and has apparently ubiquitous transcriptional activity, as reflected by broad spatial and temporal expressed sequence tag (EST) expression patterns, indicating ubiquitous transcriptional activity. This latter feature is especially important in stem cells, where during differentiation, chromatin remodeling typically leads to silencing of some loci and potential activation of others. Within the region suitable for exogenous insertion, a precise locus chosen for insertion should be devoid of repetitive elements and conserved sequences and to which primers for amplification of homology arms could easily be designed.

Suitable sites for human genome editing, or specifically, targeted integration, include, but are not limited to the adeno-associated virus site 1 (AAVS1), the chemokine (CC motif) receptor 5 (CCR5) gene locus and the human orthologue of the mouse ROSA26 locus. Additionally, the human orthologue of the mouse H11 locus may also be a suitable site for insertion using the composition and method of targeted integration disclosed herein. Further, collagen and HTRP gene loci may also be used as safe harbor for targeted integration. However, validation of each selected site has been shown to be necessary especially in stem cells for specific integration events, and optimization of insertion strategy including promoter election, exogenous gene sequence and arrangement, and construct design is often needed.

For targeted in/dels, the editing site is often comprised in an endogenous gene whose expression and/or function is intended to be disrupted. In one embodiments, the endogenous gene comprising a targeted in/del is associated with immune response regulation and modulation. In some other embodiments, the endogenous gene comprising a targeted in/del is associated with targeting modality, receptors, signaling molecules, transcription factors, drug target candidates, immune response regulation and modulation, or proteins suppressing engraftment, trafficking, homing, viability, self-renewal, persistence, and/or survival of stem cells and/or progenitor cells, and the derived cells therefrom.

As such, one aspect of the present invention provides a method of targeted integration in a selected locus including genome safe harbor or a preselected locus known or proven to be safe and well-regulated for continuous or temporal gene expression such as the B2M, TAP1, TAP2 or tapasin locus as provided herein. In one embodiment, the genome safe harbor for the method of targeted integration comprises one or more desired integration site comprising AAVS1, CCR5, ROSA26, collagen, HTRP, H11, beta-2 microglobulin, GAPDH, TCR or RUNX1, or other loci meeting the criteria of a genome safe harbor. In one embodiment, the method of targeted integration in a cell comprising introducing a construct comprising one or more exogenous polynucleotides to the cell, and introducing a construct comprising a pair of homologous arm specific to a desired integration site and one or more exogenous sequence, to enable site specific homologous recombination by the cell host enzymatic machinery, wherein the desired integration site comprises AAVS1, CCR5, ROSA26, collagen, HTRP, H11, beta-2 microglobulin, GAPDH, TCR or RUNX1, or other loci meeting the criteria of a genome safe harbor.

In another embodiment, the method of targeted integration in a cell comprises introducing a construct comprising one or more exogenous polynucleotides to the cell, and introducing a ZFN expression cassette comprising a DNA-binding domain specific to a desired integration site to the cell to enable a ZFN-mediated insertion, wherein the desired integration site comprises AAVS1, CCR5, ROSA26, collagen, HTRP, H11, beta-2 microglobulin, GAPDH, TCR or RUNX1, or other loci meeting the criteria of a genome safe harbor. In yet another embodiment, the method of targeted integration in a cell comprises introducing a construct comprising one or more exogenous polynucleotides to the cell, and introducing a TALEN expression cassette comprising a DNA-binding domain specific to a desired integration site to the cell to enable a TALEN-mediated insertion, wherein the desired integration site comprises AAVS1, CCR5, ROSA26, collagen, HTRP, H11, beta-2 microglobulin, GAPDH, TCR or RUNX1, or other loci meeting the criteria of a genome safe harbor. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion, wherein the desired integration site comprises AAVS1, CCR5, ROSA26, collagen, HTRP, H11, beta-2 microglobulin, GAPDH, TCR or RUNX1, or other loci meeting the criteria of a genome safe harbor. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration, wherein the desired integration site comprises AAVS1, CCR5, ROSA26, collagen, HTRP, H11, beta-2 microglobulin, GAPDH, TCR or RUNX1, or other loci meeting the criteria of a genome safe harbor.

Further, as provided herein, the above method for targeted integration in a safe harbor is used to insert any polynucleotide of interest, for example, polynucleotides encoding safety switch proteins, targeting modality, receptors, signaling molecules, transcription factors, pharmaceutically active proteins and peptides, drug target candidates, and proteins promoting engraftment, trafficking, homing, viability, self-renewal, persistence, and/or survival of stem cells and/or progenitor cells. In some other embodiments, the construct comprising one or more exogenous polynucleotides further comprises one or more marker genes. In one embodiment, the exogenous polynucleotide in a construct of the invention is a suicide gene encoding safety switch protein. Suitable suicide gene systems for induced cell death include, but not limited to Caspase 9 (or caspase 3 or 7) and AP1903; thymidine kinase (TK) and ganciclovir (GCV); cytosine deaminase (CD) and 5-fluorocytosine (5-FC). Additionally, some suicide gene systems are cell type specific, for example, the genetic modification of T lymphocytes with the B-cell molecule CD20 allows their elimination upon administration of mAb Rituximab. Further, modified EGFR containing epitope recognized by cetuximab can be used to deplete genetically engineered cells when the cells are exposed to cetuximab. As such, one aspect of the invention provides a method of targeted integration of one or more suicide genes encoding safety switch proteins selected from caspase 9 (caspase 3 or 7), thymidine kinase, cytosine deaminase, modified EGFR, and B-cell CD20.

In some embodiments, one or more exogenous polynucleotides integrated by the method herein are driven by operatively linked exogenous promoters comprised in the construct for targeted integration. The promoters may be inducible, or constructive, and may be temporal-, tissue- or cell type-specific. Suitable constructive promoters for methods of the invention include, but not limited to, cytomegalovirus (CMV), elongation factor 1α (EF1α), phosphoglycerate kinase (PGK), hybrid CMV enhancer/chicken β-actin (CAG) and ubiquitin C (UBC) promoters. In one embodiment, the exogenous promoter is CAG.

The exogenous polynucleotides integrated by the method herein may be driven by endogenous promoters in the host genome, at the integration site. In one embodiment, the method of the invention is used for targeted integration of one or more exogenous polynucleotides at AAVS1 locus in the genome of a cell. In one embodiment, at least one integrated polynucleotide is driven by the endogenous AAVS1 promoter. In another embodiment, the method of the invention is used for targeted integration at ROSA26 locus in the genome of a cell. In one embodiment, at least one integrated polynucleotide is driven by the endogenous ROSA26 promoter. In still another embodiment, the method of the invention is used for targeted integration at H11 locus in the genome of a cell. In one embodiment, at least one integrated polynucleotide is driven by the endogenous H11 promoter. In another embodiment, the method of the invention is used for targeted integration at collagen locus in the genome of a cell. In one embodiment, at least one integrated polynucleotide is driven by the endogenous collagen promoter. In still another embodiment, the method of the invention is used for targeted integration at HTRP locus in the genome of a cell. In one embodiment, at least one integrated polynucleotide is driven by the endogenous HTRP promoter. Theoretically, only correct insertions at the desired location would enable gene expression of an exogenous gene driven by an endogenous promoter.

In some embodiments, the one or more exogenous polynucleotides comprised in the construct for the methods of targeted integration are driven by one promoter. In some embodiments, the construct comprises one or more linker sequences between two adjacent polynucleotides driven by the same promoter to provide greater physical separation between the moieties and maximize the accessibility to enzymatic machinery. The linker peptide of the linker sequences may consist of amino acids selected to make the physical separation between the moieties (exogenous polynucleotides, and/or the protein or peptide encoded therefrom) more flexible or more rigid depending on the relevant function. The linker sequence may be cleavable by a protease or cleavable chemically to yield separate moieties. Examples of enzymatic cleavage sites in the linker include sites for cleavage by a proteolytic enzyme, such as enterokinase, Factor Xa, trypsin, collagenase, and thrombin. In some embodiments, the protease is one which is produced naturally by the host or it is exogenously introduced. Alternatively, the cleavage site in the linker may be a site capable of being cleaved upon exposure to a selected chemical, e.g., cyanogen bromide, hydroxylamine, or low pH. The optional linker sequence may serve a purpose other than the provision of a cleavage site. The linker sequence should allow effective positioning of the moiety with respect to another adjacent moiety for the moieties to function properly. The linker may also be a simple amino acid sequence of a sufficient length to prevent any steric hindrance between the moieties. In addition, the linker sequence may provide for post-translational modification including, but not limited to, e.g., phosphorylation sites, biotinylation sites, sulfation sites, γ-carboxylation sites, and the like. In some embodiments, the linker sequence is flexible so as not hold the biologically active peptide in a single undesired conformation. The linker may be predominantly comprised of amino acids with small side chains, such as glycine, alanine, and serine, to provide for flexibility. In some embodiments about 80 or 90 percent or greater of the linker sequence comprises glycine, alanine, or serine residues, particularly glycine and serine residues. In several embodiments, a G4S linker peptide separates the end-processing and endonuclease domains of the fusion protein. In other embodiments, a 2A linker sequence allows for two separate proteins to be produced from a single translation. Suitable linker sequences can be readily identified empirically. Additionally, suitable size and sequences of linker sequences also can be determined by conventional computer modeling techniques. In one embodiment, the linker sequence encodes a self-cleaving peptide. In one embodiment, the self-cleaving peptide is 2A. In some other embodiments, the linker sequence provides an Internal Ribosome Entry Sequence (IRES). In some embodiments, any two consecutive linker sequences are different.

The method of introducing into cells a construct comprising exogenous polynucleotides for targeted integration can be achieved using a method of gene transfer to cells known per se. In one embodiment, the construct comprises backbones of viral vectors such as adenovirus vector, adeno-associated virus vector, retrovirus vector, lentivirus vector, Sendai virus vector. In some embodiments, the plasmid vectors are used for delivering and/or expressing the exogenous polynucleotides to target cells (e.g., pA1-11, pXT1, pRc/CMV, pRc/RSV, pcDNAI/Neo) and the like. In some other embodiments, the episomal vector is used to deliver the exogenous polynucleotide to target cells. In some embodiments, recombinant adeno-associated viruses (rAAV) can be used for genetic engineering to introduce insertions, deletions or substitutions through homologous recombinations. Unlike lentiviruses, rAAVs do not integrate into the host genome. In addition, episomal rAAV vectors mediate homology-directed gene targeting at much higher rates compared to transfection of conventional targeting plasmids. In some embodiments, an AAV6 or AAV2 vector is used to introduce insertions, deletions or substitutions in a target site in the genome of iPSCs. In some embodiments, the genomically modified iPSCs and its derivative cells obtained using the methods and composition herein comprise at least one genotype listed in Table 1.

III. Method of Obtaining and Maintaining Genome-Engineered iPSCs

The present invention provides a method of obtaining and maintaining genome-engineered iPSCs comprising one or more targeted editing at one or more desired sites, wherein the targeted editing remains intact and functional in expanded genome-engineered iPSCs or the iPSCs derived non-pluripotent cells at the respective selected editing site. The targeted editing introduces into the genome iPSC, and derivative cells therefrom, insertions, deletions, and/or substitutions, i.e., targeted integration and/or in/dels at selected sites. In comparison to direct engineering patient-sourced, peripheral blood originated primary effector cells, the many benefits of obtaining genomically engineered derivative cells through editing and differentiating iPSC as provided herein include, but are not limited to: unlimited source for engineered effector cells; no need for repeated manipulation of the effector cells especially when multiple engineered modalities are involved; the obtained effector cells are rejuvenated for having elongated telomere and experiencing less exhaustion; the effector cell population is homogeneous in terms of editing site, copy number, and void of allelic variation, random mutations and expression variegation, largely due to the enabled clonal selection in engineered iPSCs as provided herein.

In particular embodiments, the genome-engineered iPSCs comprising one or more targeted editing at one or more selected sites are maintained, passaged and expanded as single cells for an extended period in the cell culture medium shown in Table 2 as Fate Maintenance Medium (FMM), wherein the iPSCs retain the targeted editing and functional modification at the selected site(s). The components of the medium may be present in the medium in amounts within an optimal range shown in Table 2. The iPSCs cultured in FMM have been shown to continue to maintain their undifferentiated, and ground or naïve, profile; genomic stability without the need for culture cleaning or selection; and are readily to give rise to all three somatic lineages, in vitro differentiation via embryoid bodies or monolayer (without formation of embryoid bodies); and in vivo differentiation by teratoma formation. See, for example, U.S. Application No. 61/947,979, the disclosure of which is incorporated herein by reference.

TABLE 2

Exemplary media for iPSC reprogramming and maintenance

| Conventional hESC Medium (Conv.) | Fate Reprogramming Medium (FRM) | Fate Maintenance Medium (FMM) |
|---|---|---|
| DMEM/F12 | DMEM/F12 | DMEM/F12 |
| Knockout Serum Replacement (20%) | Knockout Serum Replacement (20%) | Knockout Serum Replacement (20%) |
| | N2 | |
| | B27 | |
| Glutamine | Glutamine | Glutamine (1×) |
| Non-Essential Amino Acids (1×) | Non-Essential Amino Acids (1×) | Non-Essential Amino Acids (1×) |
| β-mercaptoethanol (100 μM) | β-mercaptoethanol (100 μM) | β-mercaptoethanol (100 μM) |
| bFGF (0.2-50 ng/mL) | bFGF (2-500 ng/mL) | bFGF (2-500 ng/mL) |
| | LIF (0.2-50 ng/mL) | LIF (0.2-50 ng/mL) |
| | Thiazovivin (0.1-25 μM) | Thiazovivin (0.1-25 μM) |
| | PD0325901 (0.005-2 μM) | PD0325901 (0.005-2 μM) |
| | CHIR99021 (0.02-5 μM) | CHIR99021 (0.02-5 μM) |
| | SB431542 (0.04-10 μM) | |
| In combination with MEF feeder cells | Feeder-free, in combination with Matrigel™ or Vitronectin | |

In some embodiments, the genome-engineered iPSCs comprising one or more targeted integration and/or in/dels are maintained, passaged and expanded in a medium comprising a MEK inhibitor, a GSK3 inhibitor, and a ROCK inhibitor, and free of, or essentially free of, TGFβ receptor/ALK5 inhibitors, wherein the iPSCs retain the intact and functional targeted editing at the selected sites.

Another aspect of the invention provides a method of generating genome-engineered iPSCs through targeted editing of iPSCs; or through first generating genome-engineered non-pluripotent cells by targeted editing, and then reprogramming the selected/isolated genome-engineered non-pluripotent cells to obtain iPSCs comprising the same targeted editing as the non-pluripotent cells. A further aspect of the invention provides genome-engineering non-pluripotent cells which are concurrently undergoing reprogramming by introducing targeted integration and/or targeted in/dels to the cells, wherein the contacted non-pluripotent cells are under sufficient conditions for reprogramming, and wherein the conditions for reprogramming comprise contacting non-pluripotent cells with one or more reprogramming factors and small molecules. In various embodiments of the method for concurrent genome-engineering and reprogramming, the targeted integration and/or targeted in/dels may be introduced to the non-pluripotent cells prior to, or essentially concomitantly with, initiating reprogramming by contacting the non-pluripotent cells with one or more reprogramming factors and optionally small molecules.

In some embodiments, to concurrently genome-engineer and reprogram non-pluripotent cells, the targeted integration and/or in/dels may also be introduced to the non-pluripotent cells after the multi-day process of reprogramming is initiated by contacting the non-pluripotent cells with one or more reprogramming factors and small molecules, and wherein the vectors carrying the constructs are introduced before the reprogramming cells present stable expression of one or more endogenous pluripotent genes including but not limited to SSEA4, Tra181 and CD30.

In some embodiments, the reprogramming is initiated by contacting the non-pluripotent cells with at least one reprogramming factor, and optionally a combination of a TGFβ receptor/ALK inhibitor, a MEK inhibitor, a GSK3 inhibitor and a ROCK inhibitor (FRM; Table 2). In some embodiments, the genome-engineered iPSCs through any methods above are further maintained and expanded using a mixture of comprising a combination of a MEK inhibitor, a GSK3 inhibitor and a ROCK inhibitor (FMM; Table 2).

In some embodiments of the method of generating genome-engineered iPSCs, the method comprises: genomic engineering an iPSC by introducing one or more targeted integration and/or in/dels into iPSCs to obtain genome-engineered iPSCs having at least one genotype listed in Table 1. Alternatively, the method of generating genome-engineered iPSCs comprises: (a) introducing one or more targeted editing into non-pluripotent cells to obtain genome-engineered non-pluripotent cells comprising targeted integration and/or in/dels at selected sites, and (b) contacting the genome-engineered non-pluripotent cells with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted integration and/or in/dels at selected sites. Alternatively, the method of generating genome-engineered iPSCs comprises: (a) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate the reprogramming of the non-pluripotent cells; (b) introducing one or more targeted integration and/or in/dels into the reprogramming non-pluripotent cells for genome-engineering; and (c) obtaining clonal genome-engineered iPSCs comprising targeted integration and/or in/dels at selected sites.

The reprogramming factors are selected from the group consisting of OCT4, SOX2, NANOG, KLF4, LIN28, C-MYC, ECAT1, UTF1, ESRRB, SV4OLT, HESRG, CDH1, TDGF1, DPPA4, DNMT3B, ZIC3, L1TD1, and any combinations thereof as disclosed in PCT/US2015/018801 and PCT/US16/57136, the disclosure of which are incorporated herein by reference. The one or more reprogramming factors may be in a form of polypeptide. The reprogramming factors may also be in a form of polynucleotides, and thus are introduced to the non-pluripotent cells by vectors such as, a retrovirus, a Sendai virus, an adenovirus, an episome, a plasmid, and a mini-circle. In particular embodiments, the one or more polynucleotides encoding at least one reprogramming factor are introduced by a lentiviral vector. In some embodiments, the one or more polynucleotides introduced by an episomal vector. In various other embodiments, the one or more polynucleotides are introduced by a Sendai viral vector. In some embodiments, the one or more polynucleotides introduced by a combination of plasmids. See, for example, U.S. Application No. 62/571,105, the disclosure of which is incorporated herein by reference.

In some embodiments, the non-pluripotent cells are transferred with multiple constructs comprising different exogenous polynucleotides and/or different promoters by multiple vectors for targeted integration at the same or different selected sites. These exogenous polynucleotides may comprise a suicide gene, or a gene encoding targeting modality, receptors, signaling molecules, transcription factors, pharmaceutically active proteins and peptides, drug target candidates, or a gene encoding a protein promoting engraftment, trafficking, homing, viability, self-renewal, persistence, and/or survival of the iPSCs or derivative cells thereof. In some embodiments, the exogenous polynucleotides encode RNA, including but not limited to siRNA, shRNA, miRNA and antisense nucleic acids. These exogenous polynucleotides may be driven by one or more promoters selected form the group consisting of constitutive promoters, inducible promoters, temporal-specific promoters, and tissue or cell type specific promoters. Accordingly, the polynucleotides are expressible when under conditions that activate the promoter, for example, in the presence of an inducing agent or in a particular differentiated cell type. In some embodiments, the polynucleotides are expressed in iPSCs and/or in cells differentiated from the iPSCs. In one embodiment, one or more suicide gene is driven by a constitutive promoter, for example Capase-9 driven by CAG. These constructs comprising different exogenous polynucleotides and/or different promoters can be transferred to non-pluripotent cells either simultaneously or consecutively. The non-pluripotent cells subjecting to targeted integration of multiple constructs can simultaneously contact the one or more reprogramming factors to initiate the reprogramming concurrently with the genomic engineering, thereby obtaining genome-engineered iPSCs comprising multiple targeted integration in the same pool of cells. As such, this robust method enables a concurrent reprogramming and engineering strategy to derive a clonal genomically engineered hiPSC with multiple modalities integrated to one or more selected target sites. In some embodiments, the genomically modified iPSCs and its derivative cells obtained using the methods and composition herein comprise at least one genotype listed in Table 1.

IV. A method of Obtaining Genetically-Engineered Effector Cells by Differentiating Genome-Engineered iPSC A further aspect of the present invention provides a method of in vivo differentiation of genome-engineered iPSC by teratoma formation, wherein the differentiated cells derived in vivo from the genome-engineered iPSCs retain the intact and functional targeted editing including targeted integration and/or in/dels at the desired site(s). In some embodiments, the differentiated cells derived in vivo from the genome-engineered iPSCs via teratoma comprise one or more inducible suicide genes integrated at one or more desired site comprising AAVS1, CCR5, ROSA26, collagen, HTRP H11, beta-2 microglobulin, GAPDH, TCR or RUNX1, or other loci meeting the criteria of a genome safe harbor. In some other embodiments, the differentiated cells derived in vivo from the genome-engineered iPSCs via teratoma comprise polynucleotides encoding targeting modality, or encoding proteins promoting trafficking, homing, viability, self-renewal, persistence, and/or survival of stem cells and/or progenitor cells. In some embodiments, the differentiated cells derived in vivo from the genome-engineered iPSCs via teratoma comprising one or more inducible suicide genes further comprises one or more in/dels in endogenous genes associated with immune response regulation and mediation. In some embodiments, the in/del is comprised in one or more endogenous check point genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In some embodiments, the in/del is comprised in one or more endogenous genes including, but not limited to, B2M, PD1, TAP1, TAP2, Tapasin, TCR genes. In one embodiment, the genome-engineered iPSC comprising one or more exogenous polynucleotides at selected site(s) further comprises a targeted editing in B2M (beta-2-microglobulin) encoding gene.

In particular embodiments, the genome-engineered iPSCs comprising one or more genetic modifications as provided herein are used to derive hematopoietic cell lineages or any other specific cell types in vitro, wherein the derived non-pluripotent cells retain the functional genetic modifications including targeted editing at the selected site(s). In one embodiment, the genome-engineered iPSC-derived cells include, but are not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages, wherein these cells derived from the genome-engineered iPSCs retain the functional genetic modifications including targeted editing at the desired site(s).

Applicable differentiation methods and compositions for obtaining iPSC-derived hematopoietic cell lineages include those depicted in, for example, International Application No. PCT/US2016/044122, the disclosure of which is incorporated herein by reference. As provided, the methods and compositions for generating hematopoietic cell lineages are through definitive hemogenic endothelium (HE) derived from pluripotent stem cells, including hiPSCs, under serum-free, feeder-free, and/or stromal-free conditions and in a scalable and monolayer culturing platform without the need of EB formation. Cells that may be differentiated according to the provided methods range from pluripotent stem cells, to progenitor cells that are committed to particular terminally differentiated cells and transdifferentiated cells, and to cells of various lineages directly transitioned to hematopoietic fate without going through a pluripotent intermediate. Similarly, the cells that are produced by differentiating stem cells range from multipotent stem or progenitor cells, to terminally differentiated cells, and to all intervening hematopoietic cell lineages.

The methods for differentiating and expanding cells of the hematopoietic lineage from pluripotent stem cells in monolayer culturing comprise contacting the pluripotent stem cells with a BMP pathway activator, and optionally, bFGF. As provided, the pluripotent stem cell-derived mesodermal cells are obtained and expanded without forming embryoid bodies from pluripotent stem cells. The mesodermal cells are then subjected to contact with a BMP pathway activator, bFGF, and a WNT pathway activator to obtain expanded mesodermal cells having definitive hemogenic endothelium (HE) potential without forming embryoid bodies from the pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The methods provided herein for obtaining cells of the hematopoietic lineage are superior to EB-mediated pluripotent stem cell differentiation, because EB formation leads to modest to minimal cell expansion, does not allow monolayer culturing which is important for many applications requiring homogeneous expansion, and homogeneous differentiation of the cells in a population, and is laborious and low efficiency.

The provided monolayer differentiation platform facilitates differentiation towards definitive hemogenic endothelium resulting in the derivation of hematopoietic stem cells and differentiated progeny such as T, B, NKT and NK cells. The monolayer differentiation strategy combines enhanced differentiation efficiency with large-scale expansion enables the delivery of therapeutically relevant number of pluripotent stem cell-derived hematopoietic cells for various therapeutic applications. Further, the monolayer culturing using the methods provided herein leads to functional hematopoietic lineage cells that enable full range of in vitro differentiation, ex vivo modulation, and in vivo long term hematopoietic self-renewal, reconstitution and engraftment. As provided, the iPSC derived hematopoietic lineage cells include, but not limited to, definitive hemogenic endothelium, hematopoietic multipotent progenitor cells, hematopoietic stem and progenitor cells, T cell progenitors, NK cell progenitors, T cells, NK cells, NKT cells, B cells, macrophages, and neutrophils.

The method for directing differentiation of pluripotent stem cells into cells of a definitive hematopoietic lineage, wherein the method comprises: (i) contacting pluripotent stem cells with a composition comprising a BMP activator, and optionally bFGF, to initiate differentiation and expansion of mesodermal cells from the pluripotent stem cells; (ii) contacting the mesodermal cells with a composition comprising a BMP activator, bFGF, and a GSK3 inhibitor, wherein the composition is optionally free of TGFβ receptor/ALK inhibitor, to initiate differentiation and expansion of mesodermal cells having definitive HE potential from the mesodermal cells; (iii) contacting the mesodermal cells having definitive HE potential with a composition comprising a ROCK inhibitor; one or more growth factors and cytokines selected from the group consisting of bFGF, VEGF, SCF, IGF, EPO, IL6, and IL11; and optionally, a Wnt pathway activator, wherein the composition is optionally free of TGFβ receptor/ALK inhibitor, to initiate differentiation and expansion of definitive hemogenic endothelium from pluripotent stem cell-derived mesodermal cells having definitive hemogenic endothelium potential.

In some embodiments, the method further comprises contacting pluripotent stem cells with a composition comprising a MEK inhibitor, a GSK3 inhibitor, and a ROCK inhibitor, wherein the composition is free of TGFβ receptor/ALK inhibitors, to seed and expand the pluripotent stem cells. In some embodiments, the pluripotent stem cells are iPSCs, or naïve iPSCs, or iPSCs comprising one or more genetic imprints; and the one or more genetic imprints comprised in the iPSC are retained in the hematopoietic cells differentiated therefrom. In some embodiments of the method for directing differentiation of pluripotent stem cells into cells of a hematopoietic lineage, the differentiation of the pluripotent stem cells into cells of hematopoietic lineage is void of generation of embryoid bodies and is in a monolayer culturing form.

In some embodiments of the above method, the obtained pluripotent stem cell-derived definitive hemogenic endothelium cells are CD34+. In some embodiments, the obtained definitive hemogenic endothelium cells are CD34+CD43−. In some embodiments, the definitive hemogenic endothelium cells are CD34+CD43−CXCR4−CD73−. In some embodiments, the definitive hemogenic endothelium cells are CD34+ CXCR4−CD73−. In some embodiments, the definitive hemogenic endothelium cells are CD34+CD43−CD93−. In some embodiments, the definitive hemogenic endothelium cells are CD34+ CD93−.

In some embodiments of the above method, the method further comprises (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, and IL7; and optionally a BM' activator; to initiate the differentiation of the definitive hemogenic endothelium to pre-T cell progenitors; and optionally, (ii) contacting the pre-T cell progenitors with a composition comprising one or more growth factors and cytokines selected from the group consisting of SCF, Flt3L, and IL7, but free of one or more of VEGF, bFGF, TPO, BMP activators and ROCK inhibitors, to initiate the differentiation of the pre-T cell progenitors to T cell progenitors or T cells. In some embodiments of the method, the pluripotent stem cell-derived T cell progenitors are CD34+CD45+CD7+. In some embodiments of the method, the pluripotent stem cell-derived T cell progenitors are CD45+CD7+.

In yet some embodiments of the above method for directing differentiation of pluripotent stem cells into cells of a hematopoietic lineage, the method further comprises: (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, IL3, IL7, and IL15; and optionally, a BMP activator, to initiate differentiation of the definitive hemogenic endothelium to pre-NK cell progenitor; and optionally, (ii) contacting pluripotent stem cells-derived pre-NK cell progenitors with a composition comprising one or more growth factors and cytokines selected from the group consisting of SCF, Flt3L, IL3, IL7, and IL15, wherein the medium is free of one or more of VEGF, bFGF, TPO, BMP activators and ROCK inhibitors, to initiate differentiation of the pre-NK cell progenitors to NK cell progenitors or NK cells. In some embodiments, the pluripotent stem cell-derived NK progenitors are CD3-CD45+CD56+CD7+. In some embodiments, the pluripotent stem cell-derived NK cells are CD3-CD45+CD56+, and optionally further defined by NKp46+, CD57+ and CD16+.

Therefore, using the above differentiation methods, one may obtain one or more population of iPSC derived hematopoietic cells (i) CD34+ HE cells (iCD34), using one or more culture medium selected from iMPP-A, iTC-A2, iTC-B2, iNK-A2, and iNK-B2; (ii) definitive hemogenic endothelium (iHE), using one or more culture medium selected from iMPP-A, iTC-A2, iTC-B2, iNK-A2, and iNK-B2; (iii) definitive HSCs, using one or more culture medium selected from iMPP-A, iTC-A2, iTC-B2, iNK-A2, and iNK-B2; (iv) multipotent progenitor cells (iMPP), using iMPP-A; (v) T cell progenitors (ipro-T), using one or more culture medium selected from iTC-A2, and iTC-B2; (vi) T cells (iTC), using iTC-B2; (vii) NK cell progenitors (ipro-NK), using one or more culture medium selected from iNK-A2, and iNK-B2; and/or (viii) NK cells (iNK), and iNK-B2. In some embodiments, the medium:

a. iCD34-C comprises a ROCK inhibitor, one or more growth factors and cytokines selected from the group consisting of bFGF, VEGF, SCF, IL6, IL11, IGF, and EPO, and optionally, a Wnt pathway activator; and is free of TGFβ receptor/ALK inhibitor;
b. iMPP-A comprises a BMP activator, a ROCK inhibitor, and one or more growth factors and cytokines selected from the group consisting of TPO, IL3, GMCSF, EPO, bFGF, VEGF, SCF, IL6, Flt3L and IL11;
c. iTC-A2 comprises a ROCK inhibitor; one or more growth factors and cytokines selected from the group consisting of SCF, Flt3L, TPO, and IL7; and optionally, a BMP activator;
d. iTC-B2 comprises one or more growth factors and cytokines selected from the group consisting of SCF, Flt3L, and IL7;
e. iNK-A2 comprises a ROCK inhibitor, and one or more growth factors and cytokines selected from the group consisting of SCF, Flt3L, TPO, IL3, IL7, and IL15; and optionally, a BMP activator, and
f. iNK-B2 comprises one or more growth factors and cytokines selected from the group consisting of SCF, Flt3L, IL7 and IL15.

In some embodiments, the genome-engineered iPSC-derived cells obtained from the above methods comprise one or more inducible suicide gene integrated at one or more desired integration sites comprising AAVS1, CCR5, ROSA26, collagen, HTRP, H11, beta-2 microglobulin, GAPDH, TCR or RUNX1, or other loci meeting the criteria of a genome safe harbor. In some other embodiments, the genome-engineered iPSC-derived cells comprise polynucleotides encoding safety switch proteins, targeting modality, receptors, signaling molecules, transcription factors, pharmaceutically active proteins and peptides, drug target candidates, or proteins promoting trafficking, homing, viability, self-renewal, persistence, and/or survival of stem cells and/or progenitor cells. In some embodiments, the genome-engineered iPSC-derived cells comprising one or more suicide genes further comprise one or more in/del comprised in one or more endogenous genes associated with immune response regulation and mediation, including, but not limited to, check point genes, endogenous T cell receptor genes, and MHC class I suppressor genes. In one embodiment, the genome-engineered iPSC-derived cells comprising one or more suicide genes further comprise an in/del in B2M gene, wherein the B2M is knocked out.

Additionally, applicable dedifferentiation methods and compositions for obtaining genomic-engineered hematopoietic cells of a first fate to genomic-engineered hematopoietic cells of a second fate include those depicted in, for example, International Publication No. WO2011/159726, the disclosure of which is incorporated herein by reference. The method and composition provided therein allows partially reprogramming a starting non-pluripotent cell to a non-pluripotent intermediate cell by limiting the expression of endogenous Nanog gene during reprogramming; and subjecting the non-pluripotent intermediate cell to conditions for differentiating the intermediate cell into a desired cell type. In some embodiments, the genomically modified iPSCs and its derivative cells obtained using the methods and composition herein comprise at least one genotype listed in Table 1.

V. Therapeutic Use of Derivative Immune Cells with Functional Modalities Differentiated from Genetically Engineered iPSCs The present invention provides, in some embodiments, a composition comprising an isolated population or subpopulation functionally enhanced derivative immune cells that have been differentiated from genomically engineered iPSCs using the methods and compositions as disclosed. In some embodiments, the iPSCs comprise one or more targeted genetic editing which are retainable in the iPSC-derived immune cells, wherein the genetically engineered iPSCs and derivative cells thereof are suitable for cell based adoptive therapies. In one embodiment, the isolated population or subpopulation of genetically engineered immune cell comprises iPSC derived CD34 cells. In one embodiment, the isolated population or subpopulation of genetically engineered immune cell comprises iPSC derived HSC cells. In one embodiment, the isolated population or subpopulation of genetically engineered immune cell comprises iPSC derived proT or T cells. In one embodiment, the isolated population or subpopulation of genetically engineered immune cell comprises iPSC derived proNK or NK cells. In one embodiment, the isolated population or subpopulation of genetically engineered immune cell comprises iPSC derived immune regulatory cells or myeloid derived suppressor cells (MDSCs). In some embodiments, the iPSC derived genetically engineered immune cells are further modulated ex vivo for improved therapeutic potential. In one embodiment, an isolated population or subpopulation of genetically engineered immune cells that have been derived from iPSC comprises an increased number or ratio of naïve T cells, stem cell memory T cells, and/or central memory T cells. In one embodiment, the isolated population or subpopulation of genetically engineered immune cell that have been derived from iPSC comprises an increased number or ratio of type I NKT cells. In another embodiment, the isolated population or subpopulation of genetically engineered immune cell that have been derived from iPSC comprises an increased number or ratio of adaptive NK cells. In some embodiments, the isolated population or subpopulation of genetically engineered CD34 cells, HSC cells, T cells, NK cells, or myeloid derived suppressor cells derived from iPSC are allogeneic. In some other embodiments, the isolated population or subpopulation of genetically engineered CD34 cells, HSC cells, T cells, NK cells, or MDSC derived from iPSC are autogenic.

In some embodiments, the iPSC for differentiation comprises genetic imprints selected to convey desirable therapeutic attributes in effector cells, provided that cell development biology during differentiation is not disrupted, and provided that the genetic imprints are retained and functional in the differentiated hematopoietic cells derived from said iPSC.

In some embodiments, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell, wherein the iPSC retain the source therapeutic attributes, which are also comprised in the iPSC derived hematopoietic lineage cells.

In some embodiments, the genetically modified modalities comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In some embodiments, the genetically modified iPSC and the derivative cells thereof comprise a genotype listed in Table 1. In some other embodiments, the genetically modified iPSC and the derivative cells thereof comprising a genotype listed in Table 1 further comprise additional genetically modified modalities comprising (1) one or more of deletion or reduced expression of TAP1, TAP2, Tapasin, NLRC5, PD1, LAG3, TIM3, RFXANK, CIITA, RFX5, or RFXAP, and any gene in the chromosome 6p21 region; and (2) introduced or increased expression of HLA-E, 41BBL, CD3, CD4, CD8, CD47, CD113, CD131, CD137, CD80, PDL1, A2AR, CAR, TCR, Fc receptor, or surface triggering receptors for coupling with bi- or multi-specific or universal engagers.

In still some other embodiments, the hematopoietic lineage cells comprise the therapeutic attributes of the source specific immune cell relating to a combination of at least two of the followings: (i) one or more antigen targeting receptor expression; (ii) modified HLA; (iii) resistance to tumor microenvironment; (iv) recruitment of bystander immune cells and immune modulations; (iv) improved on-target specificity with reduced off-tumor effect; and (v) improved homing, persistence, cytotoxicity, or antigen escape rescue.

In some embodiments, the iPSC derivative hematopoietic cells comprising a genotype listed in Table 1, and said cells express at least one cytokine and/or its receptor comprising IL2, IL4, IL6, IL7, IL9, IL10, IL11, IL12, IL15, IL18, or IL21, or any modified protein thereof, and express at least a CAR. In some embodiments, the engineered expression of the cytokine(s) and the CAR(s) is NK cell specific. In some other embodiments, the engineered expression of the cytokine(s) and the CAR(s) is T cell specific. In one embodiment, the CAR comprises a CD38 binding domain. In some embodiments, the iPSC derivative hematopoietic effector cells are antigen specific. In some embodiments, the antigen specific derivative effector cells target a liquid tumor. In some embodiments, the antigen specific derivative effector cells target a solid tumor. In some embodiments, the antigen specific iPSC derivative hematopoietic effector cells are capable of rescuing tumor antigen escape.

A variety of diseases may be ameliorated by introducing the immune cells of the invention to a subject suitable for adoptive cell therapy. In some embodiments, the iPSC derivative hematopoietic cells as provided is for allogeneic adoptive cell therapies. Additionally, the present invention provides, in some embodiments, therapeutic use of the above therapeutic compositions by introducing the composition to a subject suitable for adoptive cell therapy, wherein the subject has an autoimmune disorder; a hematological malignancy; a solid tumor; or an infection associated with HIV, RSV, EBV, CMV, adenovirus, or BK polyomavirus. Examples of hematological malignancies include, but are not limited to, acute and chronic leukemias (acute myelogenous leukemia (AML), acute lymphoblastic leukemia (ALL), chronic myelogenous leukemia (CML), lymphomas, non-Hodgkin lymphoma (NHL), Hodgkin's disease, multiple myeloma, and myelodysplastic syndromes. Examples of solid cancers include, but are not limited to, cancer of the brain, prostate, breast, lung, colon, uterus, skin, liver, bone, pancreas, ovary, testes, bladder, kidney, head, neck, stomach, cervix, rectum, larynx, and esophagus. Examples of various autoimmune disorders include, but are not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's). Examples of viral infections include, but are not limited to, HIV—(human immunodeficiency virus), HSV—(herpes simplex virus), KSHV—(Kaposi's sarcoma-associated herpesvirus), RSV—(Respiratory Syncytial Virus), EBV—(Epstein-Barr virus), CMV—(cytomegalovirus), VZV—(Varicella zoster virus), adenovirus-, a lentivirus-, a BK polyomavirus-associated disorders.

The treatment using the derived hematopoietic lineage cells of embodiments disclosed herein could be carried out upon symptom, or for relapse prevention. The terms "treating," "treatment," and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any intervention of a disease in a subject and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent or composition may be administered before, during or after the onset of a disease or an injury. The treatment of ongoing disease, where the treatment stabilizes or reduces the undesirable clinical symptoms of the patient, is also of particular interest. In particular embodiments, the subject in need of a treatment has a disease, a condition, and/or an injury that can be contained, ameliorated, and/or improved in at least one associated symptom by a cell therapy. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g. a hyperproliferative disorder or a cancer of hematopoietic system, a subject having or at risk of developing a tumor, e.g., a solid tumor, a subject who has or is at risk of having a viral infection or a disease associated with a viral infection.

When evaluating responsiveness to the treatment comprising the derived hematopoietic lineage cells of embodiments disclosed herein, the response can be measured by criteria comprising at least one of: clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST (Response Evaluation Criteria In Solid Tumors) criteria.

The therapeutic composition comprising derived hematopoietic lineage cells as disclosed can be administered in a subject before, during, and/or after other treatments. As such the method of a combinational therapy can involve the administration or preparation of iPSC derived immune cells before, during, and/or after the use of an additional therapeutic agent. As provided above, the one or more additional therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). The administration of the iPSC derived immune cells can be separated in time from the administration of an additional therapeutic agent by hours, days, or even weeks. Additionally, or alternatively, the administration can be combined with other biologically active agents or modalities such as, but not limited to, an antineoplastic agent, a non-drug therapy, such as, surgery.

In some embodiments of a combinational cell therapy, the therapeutic combination comprises the iPSC derived hematopoietic lineage cells provided herein and an additional therapeutic agent that is an antibody, or an antibody fragment. In some embodiments, the antibody is a monoclonal antibody. In some embodiments, the antibody may be a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the administered iPSC derived hematopoietic lineage cells to enhance their killing ability. In some embodiments, the antibodies suitable for combinational treatment as an additional therapeutic agent to the administered iPSC derived hematopoietic lineage cells include, but are not limited to, anti-CD20 (e.g., rituximab, veltuzumab, ofatumumab, ublituximab, ocaratuzumab, obinutuzumab), anti-HER2 (e.g., trastuzumab, pertuzumab), anti-CD52 (e.g., alemtuzumab), anti-EGFR (e.g., certuximab), anti-GD2 (e.g., dinutuximab), anti-PDL1 (e.g., avelumab), anti-CD38 (e.g., daratumumab, isatuximab, MOR202), anti-CD123 (e.g., 7G3, CSL362), anti-SLAMF7 (elotuzumab), and their humanized or Fc modified variants or fragments or their functional equivalents or biosimilars.

In some embodiments, the additional therapeutic agent comprises one or more checkpoint inhibitors. Checkpoints are referred to cell molecules, often cell surface molecules, capable of suppressing or downregulating immune responses when not inhibited. Checkpoint inhibitors are antagonists capable of reducing checkpoint gene expression or gene products, or deceasing activity of checkpoint molecules. Suitable checkpoint inhibitors for combination therapy with the derivative effector cells, including NK or T cells, as provided herein include, but are not limited to, antagonists of PD-1 (Pdcdl, CD279), PDL-1 (CD274), TIM-3 (Havcr2), TIGIT (WUCAM and Vstm3), LAG-3 (Lag3, CD223), CTLA-4 (Ctla4, CD152), 2B4 (CD244), 4-1BB (CD137), 4-1BBL (CD137L), A2aR, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR (for example, 2DL1, 2DL2, 2DL3, 3DL1, and 3DL2).

Some embodiments of the combination therapy comprising the provided derivative effector cells further comprise at least one inhibitor targeting a checkpoint molecule. Some other embodiments of the combination therapy with the provided derivative effector cells comprise two, three or more inhibitors such that two, three, or more checkpoint molecules are targeted. In some embodiments, the effector cells for combination therapy as described herein are derivative NK cells as provided. In some embodiments, the effector cells for combination therapy as described herein are derivative T cells. In some embodiments, the derivative NK or T cells for combination therapies are functionally enhanced as provided herein. In some embodiments, the two, three or more checkpoint inhibitors may be administered in a combination therapy with, before, or after the administering of the derivative effector cells. In some embodiments, the two or more checkpoint inhibitors are administered at the same time, or one at a time (sequential).

In some embodiments, the antagonist inhibiting any of the above checkpoint molecules is an antibody. In some embodiments, the checkpoint inhibitory antibodies may be murine antibodies, human antibodies, humanized antibodies, a camel Ig, a shark heavy-chain-only antibody (VNAR), Ig NAR, chimeric antibodies, recombinant antibodies, or antibody fragments thereof. Non-limiting examples of antibody fragments include Fab, Fab', F(ab)'2, F(ab)'3, Fv, single chain antigen binding fragments (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody, which may be more cost-effective to produce, more easily used, or more sensitive than the whole antibody. In some embodiments, the one, or two, or three, or more checkpoint inhibitors comprise at least one of atezolizumab, avelumab, durvalumab, ipilimumab, IPH4102, IPH43, IPH33, lirimumab, monalizumab, nivolumab, pembrolizumab, and their derivatives or functional equivalents.

The combination therapies comprising the derivative effector cells and one or more check inhibitors are applicable to treatment of liquid and solid cancers, including but not limited to cutaneous T-cell lymphoma, non-Hodgkin lymphoma (NHL), Mycosis fungoides, Pagetoid reticulosis, Sezary syndrome, Granulomatous slack skin, Lymphomatoid papulosis, Pityriasis lichenoides chronica, Pityriasis lichenoides et varioliformis acuta, CD30+ cutaneous T-cell lymphoma, Secondary cutaneous CD30+ large cell lymphoma, non-mycosis fungoides CD30 cutaneous large T-cell lymphoma, Pleomorphic T-cell lymphoma, Lennert lymphoma, subcutaneous T-cell lymphoma, angiocentric lymphoma, blastic NK-cell lymphoma, B-cell Lymphomas, hodgkins lymphoma (HL), Head and neck tumor; Squamous cell carcinoma, rhabdomyocarcoma, Lewis lung carcinoma (LLC), non-small cell lung cancer, esophageal squamous cell carcinoma, esophageal adenocarcinoma, renal cell carcinoma (RCC), colorectal cancer (CRC), acute myeloid leukemia (AML), breast cancer, gastric cancer, prostatic small cell neuroendocrine carcinoma (SCNC), liver cancer, glioblastoma, liver cancer, oral squamous cell carcinoma, pancreatic cancer, thyroid papillary cancer, intrahepatic cholangiocellular carcinoma, hepatocellular carcinoma, bone cancer, metastasis, and nasopharyngeal carcinoma.

In some embodiments, other than the derivative effector cells as provided herein, a combination for therapeutic use comprises one or more additional therapeutic agents comprising a chemotherapeutic agent or a radioactive moiety. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g. Goodman & Gilman's The Pharmacological Basis of Therapeutics, Ninth Edition, McGraw-Hill, N.Y., 1995) or through the National Cancer Institute website (fda.gov/cder/cancer/druglistfrarne.htm), both as updated from time to time.

Immunomodulatory drugs (IMiDs) such as thalidomide, lenalidomide, and pomalidomide stimulate both NK cells and T cells. As provided herein, IMiDs may be used with the iPSC derived therapeutic immune cells for cancer treatments.

Other than an isolated population of iPSC derived hematopoietic lineage cells included in the therapeutic compositions, the compositions suitable for administration to a patient can further include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, $17^{th}$ ed. 1985, the disclosure of which is hereby incorporated by reference in its entirety).

In one embodiment, the therapeutic composition comprises the pluripotent cell derived T cells made by the methods and composition disclosed herein. In one embodiment, the therapeutic composition comprises the pluripotent cell derived NK cells made by the methods and composition disclosed herein. In one embodiment, the therapeutic composition comprises the pluripotent cell derived CD34+ HE cells made by the methods and composition disclosed herein. In one embodiment, the therapeutic composition comprises the pluripotent cell derived HSCs made by the methods and composition disclosed herein. In one embodiment, the therapeutic composition comprises the pluripotent cell derived MDSC made by the methods and composition disclosed herein. A therapeutic composition comprising a population of iPSC derived hematopoietic lineage cells as disclosed herein can be administered separately by intravenous, intraperitoneal, enteral, or tracheal administration methods or in combination with other suitable compounds to affect the desired treatment goals.

These pharmaceutically acceptable carriers and/or diluents can be present in amounts sufficient to maintain a pH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the pH of the therapeutic composition is in the range from about 4 to about 10. Alternatively, the pH of the therapeutic composition is in the range from about 5 to about 9, from about 6 to about 9, or from about 6.5 to about 8. In another embodiment, the therapeutic composition includes a buffer having a pH in one of said pH ranges. In another embodiment, the therapeutic composition has a pH of about 7. Alternatively, the therapeutic composition has a pH in a range from about 6.8 to about 7.4. In still another embodiment, the therapeutic composition has a pH of about 7.4.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the iPSC derived immune cells in accordance with embodiments of the invention are suitable for use as a pharmaceutical cell culture medium. In particular embodiments, the pharmaceutically acceptable cell culture medium is a serum free, and/or feeder-free medium. In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of media suitable for use in the present invention and that there are many suitable media known and available to those in the art.

The isolated pluripotent stem cell derived hematopoietic lineage cells can have at least 50%, 60%, 70%, 80%, 90%, 95%, 98%, or 99% T cells, NK cells, NKT cells, proT cells, proNK cells, CD34+ HE cells, HSCs, B cells, myeloid-derived suppressor cells (MDSCs), regulatory macrophages, regulatory dendritic cells, or mesenchymal stromal cells. In some embodiments, the isolated pluripotent stem cell derived hematopoietic lineage cells has about 95% to about 100% T cells, NK cells, proT cells, proNK cells, CD34+ HE cells, or myeloid-derived suppressor cells (MDSCs). In some embodiments, the present invention provides therapeutic compositions having purified T cells or NK cells, such as a composition having an isolated population of about 95% T cells, NK cells, proT cells, proNK cells, CD34+ HE cells, or myeloid-derived suppressor cells (MDSCs) to treat a subject in need of the cell therapy.

In one embodiment, the combinational cell therapy comprises an anti-CD38 therapeutic protein or peptide and a population of NK cells derived from genomically engineered iPSCs comprising a genotype listed in Table 1, wherein the derived NK cells comprise CD38 null. In another embodiment, the combinational cell therapy comprises an anti-CD38 therapeutic protein or peptide and a population of T cells derived from genomically engineered iPSCs comprising a genotype listed in Table 1, wherein the derived T cells comprise CD38 null. In some embodiments, the combinational cell therapy comprises daratumumab, isatuximab, or MOR202, and a population of NK or T cells derived from genomically engineered iPSCs comprising a genotype listed in Table 1, wherein the derived NK or T cells comprise CD38 null and hnCD16. In yet some other embodiments, the combinational cell therapy comprises daratumumab, and a population of NK or T cells derived from genomically engineered iPSCs comprising a genotype listed in Table 1, wherein the derived NK or T cells comprise CD38 null, hnCD16, and a CAR targeting CD19, BCMA, CD38, CD20, CD22, or CD123. In still some additional embodiments, the combinational cell therapy comprises daratumumab, isatuximab, or MOR202, and a population of NK or T cells derived from genomically engineered iPSCs comprising a genotype listed in Table 1, wherein the derived NK or T cells comprise CD38 null, hnCD16, a CAR and one or more exogenous cytokine.

As a person of ordinary skill in the art would understand, both autologous and allogeneic hematopoietic lineage cells derived from iPSC based on the methods and composition herein can be used in cell therapies as described above. For autologous transplantation, the isolated population of derived hematopoietic lineage cells are either complete or partial HLA-match with the patient. In another embodiment, the derived hematopoietic lineage cells are not HLA-matched to the subject, wherein the derived hematopoietic lineage cells are NK cells or T cell with HLA I and HLA II null.

In some embodiments, the number of derived hematopoietic lineage cells in the therapeutic composition is at least $0.1\times10^5$ cells, at least $1\times10^5$ cells, at least $5\times10^5$ cells, at least $1\times10^6$ cells, at least $5\times10^6$ cells, at least $1\times10^7$ cells, at least $5\times10^7$ cells, at least $1\times10^8$ cells, at least $5\times10^8$ cells, at least $1\times10^9$ cells, or at least $5\times10^9$ cells, per dose. In some embodiments, the number of derived hematopoietic lineage cells in the therapeutic composition is about $0.1\times10^5$ cells to about $1\times10^6$ cells, per dose; about $0.5\times10^6$ cells to about $1\times10^7$ cells, per dose; about $0.5\times10^7$ cells to about $1\times10^8$ cells, per dose; about $0.5\times10^8$ cells to about $1\times10^9$ cells, per dose; about $1\times10^9$ cells to about $5\times10^9$ cells, per dose; about $0.5\times10^9$ cells to about $8\times10^9$ cells, per dose; about $3\times10^9$ cells to about $3\times10^{10}$ cells, per dose, or any range in-between. Generally, $1\times10^8$ cells/dose translates to $1.67\times10^6$ cells/kg for a 60 kg patient.

In one embodiment, the number of derived hematopoietic lineage cells in the therapeutic composition is the number of immune cells in a partial or single cord of blood, or is at least $0.1\times10^5$ cells/kg of bodyweight, at least $0.5\times10^5$ cells/kg of bodyweight, at least $1\times10^5$ cells/kg of bodyweight, at least $5\times10^5$ cells/kg of bodyweight, at least $10\times10^5$ cells/kg of bodyweight, at least $0.75\times10^6$ cells/kg of bodyweight, at least $1.25\times10^6$ cells/kg of bodyweight, at least $1.5\times10^6$ cells/kg of bodyweight, at least $1.75\times10^6$ cells/kg of bodyweight, at least $2\times10^6$ cells/kg of bodyweight, at least $2.5\times10^6$ cells/kg of bodyweight, at least $3\times10^6$ cells/kg of bodyweight, at least $4\times10^6$ cells/kg of bodyweight, at least $5\times10^6$ cells/kg of bodyweight, at least $10\times10^6$ cells/kg of bodyweight, at least $15\times10^6$ cells/kg of bodyweight, at least $20\times10^6$ cells/kg of bodyweight, at least $25\times10^6$ cells/kg of bodyweight, at least $30\times10^6$ cells/kg of bodyweight, $1\times10^8$ cells/kg of bodyweight, $5\times10^8$ cells/kg of bodyweight, or $1\times10^9$ cells/kg of bodyweight.

In one embodiment, a dose of derived hematopoietic lineage cells is delivered to a subject. In one illustrative embodiment, the effective amount of cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

In some embodiments, the therapeutic use of derived hematopoietic lineage cells is a single-dose treatment. In some embodiments, the therapeutic use of derived hematopoietic lineage cells is a multi-dose treatment. In some embodiments, the multi-dose treatment is one dose every day, every 3 days, every 7 days, every 10 days, every 15 days, every 20 days, every 25 days, every 30 days, every 35 days, every 40 days, every 45 days, or every 50 days, or any number of days in-between.

The compositions comprising a population of derived hematopoietic lineage cells of the invention can be sterile, and can be suitable and ready for administration (i.e., can be administered without any further processing) to human patients. A cell based composition that is ready for administration means that the composition does not require any further processing or manipulation prior to transplant or administration to a subject. In other embodiments, the invention provides an isolated population of derived hematopoietic lineage cells that are expanded and/or modulated prior to administration with one or more agents. For derived hematopoietic lineage cells that genetically engineered to express recombinant TCR or CAR, the cells can be activated and expanded using methods as described, for example, in U.S. Pat. No. 6,352,694.

In certain embodiments, the primary stimulatory signal and the co-stimulatory signal for the derived hematopoietic lineage cells can be provided by different protocols. For example, the agents providing each signal can be in solution or coupled to a surface. When coupled to a surface, the agents can be coupled to the same surface (i.e., in “cis” formation) or to separate surfaces (i.e., in “trans” formation). Alternatively, one agent can be coupled to a surface and the other agent in solution. In one embodiment, the agent providing the co-stimulatory signal can be bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents such as disclosed in U.S. Patent Application Publication Nos. 20040101519 and 20060034810 for artificial antigen presenting cells (aAPCs) that are contemplated for use in activating and expanding T lymphocytes in embodiments of the present invention.

Some variation in dosage, frequency, and protocol will necessarily occur depending on the condition of the subject being treated. The person responsible for administration will, in any event, determine the appropriate dose, frequency and protocol for the individual subject.

EXAMPLES

The following examples are offered by way of illustration and not by way of limitation.

Example 1

Materials and Methods

To effectively select and test suicide systems under the control of various promoters in combination with different safe harbor loci integration strategies, a proprietary hiPSC platform of the applicant was used, which enables single cell passaging and high-throughput, 96-well plate-based flow cytometry sorting, to allow for the derivation of clonal hiPSCs with single or multiple genetic modulations.

hiPSC Maintenance in Small Molecule Culture: hiPSCs were routinely passaged as single cells once confluency of the culture reached 75%-90%. For single-cell dissociation, hiPSCs were washed once with PBS (Mediatech) and treated with Accutase (Millipore) for 3-5 min at 37° C. followed with pipetting to ensure single-cell dissociation. The single-cell suspension was then mixed in equal volume with conventional medium, centrifuged at 225×g for 4 min, resuspended in FMM, and plated on Matrigel-coated surface. Passages were typically 1:6-1:8, transferred tissue culture plates previously coated with Matrigel for 2-4 hr in 37° C. and fed every 2-3 days with FMM. Cell cultures were maintained in a humidified incubator set at 37° C. and 5% CO2.

Human iPSC engineering with ZFN, CRISPR for targeted editing of modalities of interest: Using ROSA26 targeted insertion as an example, for ZFN mediated genome editing, 2 million iPSCs were transfected with mixture of 2.5 ug ZFN-L (FTV893), 2.5 ug ZFN-R (FTV894) and 5 ug donor construct, for AAVS1 targeted insertion. For CRISPR mediated genome editing, 2 million iPSCs were transfected with mixture of 5 ug ROSA26-gRNA/Cas9 (FTV922) and 5 ug donor construct, for ROSA26 targeted insertion. Transfection was done using Neon transfection system (Life Technologies) using parameters 1500V, 10 ms, 3 pulses. On day 2 or 3 after transfection, transfection efficiency was measured using flow cytometry if the plasmids contain artificial promoter-driver GFP and/or RFP expression cassette. On day 4 after transfection, puromycin was added to the medium at concentration of 0.1 ug/ml for the first 7 days and 0.2 ug/ml after 7 days to select the targeted cells. During the puromycin selection, the cells were passaged onto fresh matrigel-coated wells on day 10. On day 16 or later of puromycin selection, the surviving cells were analyzed by flow cytometry for GFP+iPS cell percentage.

Bulk sort and clonal sort of genome-edited iPSCs: iPSCs with genomic targeted editing using ZFN or CRISPR-Cas9 were bulk sorted and clonal sorted of GFP+SSEA4+ TRA181+ iPSCs after 20 days of puromycin selection. Single cell dissociated targeted iPSC pools were resuspended in chilled staining buffer containing Hanks' Balanced Salt Solution (MediaTech), 4% fetal bovine serum (Invitrogen), lx penicillin/streptomycin (Mediatech) and 10 mM Hepes (Mediatech); made fresh for optimal performance. Conjugated primary antibodies, including SSEA4-PE, TRA181-Alexa Fluor-647 (BD Biosciences), were added to the cell solution and incubated on ice for 15 minutes. All antibodies were used at 7 μL in 100 μL staining buffer per million cells. The solution was washed once in staining buffer, spun down at 225 g for 4 minutes and resuspended in staining buffer containing 10 μM Thiazovivn and maintained on ice for flow cytometry sorting. Flow cytometry sorting was performed on FACS Aria II (BD Biosciences). For bulk sort, GFP+SSEA4+TRA181+ cells were gated and sorted into 15 ml canonical tubes filled with 7 ml FMM. For clonal sort, the sorted cells were directly ejected into 96-well plates using the 100 μM nozzle, at concentrations of 3 events per well. Each well was prefilled with 200 μL FMM supplemented with 5 μg/mL fibronectin and 1× penicillin/streptomycin (Mediatech) and previously coated overnight with 5× Matrigel. 5× Matrigel precoating includes adding one aliquot of Matrigel into 5 mL of DMEM/F12, then incubated overnight at 4° C. to allow for proper resuspension and finally added to 96-well plates at 50 μL per well followed by overnight incubation at 37° C. The 5× Matrigel is aspirated immediately before the addition of media to each well. Upon completion of the sort, 96-well plates were centrifuged for 1-2 min at 225 g prior to incubation. The plates were left undisturbed for seven days. On the seventh day, 150 μL of medium was removed from each well and replaced with 100 μL FMM. Wells were refed with an additional 100 μL FMM on day 10 post sort. Colony formation was detected as early as day 2 and most colonies were expanded between days 7-10 post sort. In the first passage, wells were washed with PBS and dissociated with 30 μL Accutase for approximately 10 min at 37° C. The need for extended Accutase treatment reflects the compactness of colonies that have sat idle in culture for prolonged duration. After cells are seen to be dissociating, 200 μL of FMM is added to each well and pipetted several times to break up the colony. The dissociated colony is transferred to another well of a 96-well plate previously coated with 5× Matrigel and then centrifuged for 2 min at 225 g prior to incubation. This 1:1 passage is conducted to spread out the early colony prior to expansion. Subsequent passages were done routinely with Accutase treatment for 3-5 min and expansion of 1:4-1:8 upon 75-90% confluency into larger wells previously coated with 1× Matrigel in FMM. Each clonal cell line was analyzed for GFP fluorescence level and TRA1-81 expression level. Clonal lines with near 100% GFP+ and TRA1-81+ were selected for further PCR screening and analysis. Flow cytometry analysis was performed on Guava EasyCyte 8 HT (Millipore) and analyzed using Flowjo (FlowJo, LLC).

Example 2

CD38 Knockout in iPSC Using CRISPR/Cas9-Mediated Genome Editing

Alt-R® S.p. Cas9 D10A Nickase 3NLS, 100 μg is and Alt-R® CRISPR-Cas9 tracrRNA were purchased at IDT (Coralville, Iowa) and used for iPSC targeted editing. To conduct bi-allelic knockout of CD38 in iPSC using Cas9 nickase, the screened and identified targeting sequence pairs (1A and 1B, 2A and 2B, 3A and 3B) for gNA (i.e., gD/RNA or guiding polynucleotide) design are listed in Table 3:

TABLE 3

Targeting sequence specific to CD38 locus for CRISPR/Cas9 genomic editing:

| | Exon/ Chr# | Targeting Sequence | PAM | Cleavage site | SEQ ID NO: |
|---|---|---|---|---|---|
| CD38-gNA-1A | 1/4 | TTGACGCATCGCGCCAGGA | CGG | 15,778,604 | 1 |

TABLE 3-continued

Targeting sequence specific to CD38 locus for CRISPR/Cas9 genomic editing:

| | Exon/ Chr# | Targeting Sequence | PAM | Cleavage site | SEQ ID NO: |
|---|---|---|---|---|---|
| CD38-gNA-1B | 1/4 | ATTCATCCTGAGATGAGGT | GGG | 15,778,646 | 2 |
| CD38-gNA-2A | 1/4 | ACTGACGCCAAGACAGAGT | TGG | 15,778,485 | 3 |
| CD38-gNA-2B | 1/4 | CTGGTCCTGATCCTCGTCG | TGG | 15,778,520 | 4 |
| CD38-gNA-3A | 1/4 | TCCTAGAGAGCCGGCAGCA | GGG | 15,778,459 | 5 |
| CD38-gNA-3B | 1/4 | GGAGAGCCCAACTCTGTCT | TGG | 15,778,488 | 6 |

The genomically engineered iPSCs were subsequently characterized, and the bi-allelic CD38 knockout was confirmed.

Example 3

Validation of CD38$^{-/-}$ iPSC and Derivative Cells

Figure 2:
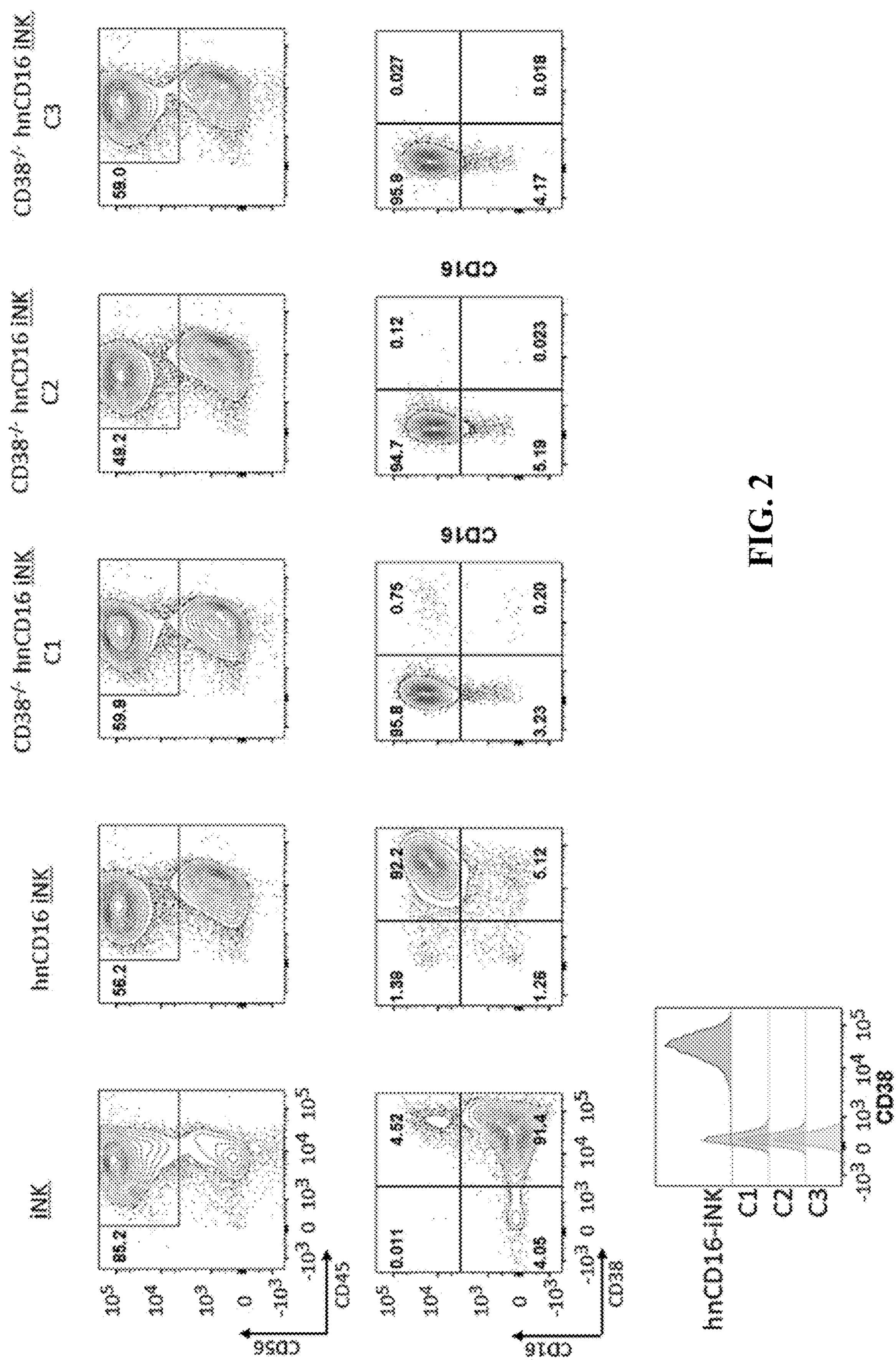
FIG. 2 shows the phenotype profiling using flow cytometry of $CD38^{-/-}$ derivative NK cells obtained from each of the three $CD38^{-/-}$ iPSC clones.

CD38 is known to express at specific cell stages and plays key roles in effector cells. During hematopoiesis, CD38 is expressed on CD34$^{+}$ stem cells and lineage-committed progenitors of lymphoid, erythroid, and myeloid, and also during the final stages of maturation of effector cells such as, T cells and NK cells. Therefore, it was unknown and there was a concern, prior to the present application, whether iPSCs comprising CD38 knockout would develop properly when subjected to directed differentiation conditions and whether the generated effector cells would be functional, considering CD38 expression profile and functionality. The CD38 null iPSC comprising a bi-allelic knockout of CD38 surprisingly maintained its ability to differentiate into derivative cells. In one of the illustrations, three engineered iPSC clones genetically edited to have bi-allelic disruption of the CD38 gene and hnCD16 were differentiated to derivative NK cells and analyzed for their phenotypes. The flow profiles in FIG. 2 shows that each clone is CD56+ while being CD38 negative.

Figure 3:
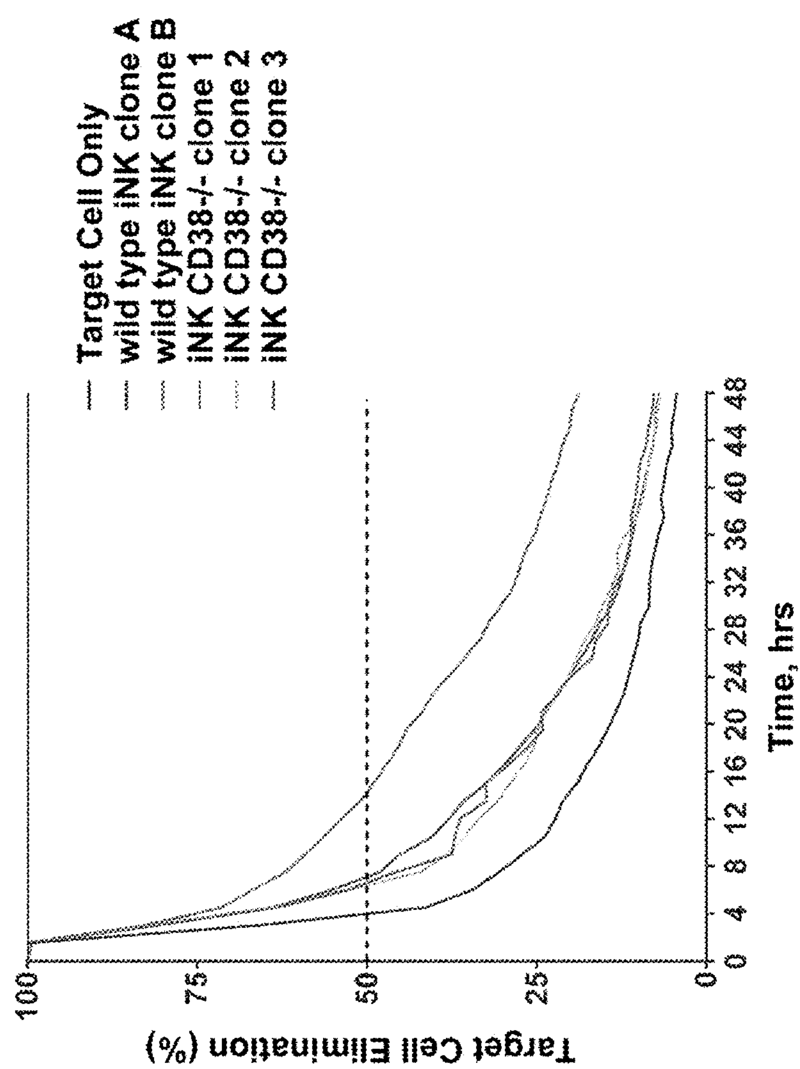
FIG. 3 shows that $CD38^{-/-}$ iPSC-derived NK cells have the same cellular cytotoxicity potential as wild-type iPSC-derived NK cells.

To determine whether cellular cytotoxicity of the iPSC-derived NK cells is retained when CD38 expression has been knocked out, wild-type iPSC clones and three engineered iPSC clones genetically edited to have bi-allelic disruption of the CD38 gene were differentiated to NK cells and compared for their ability to target and kill tumor cell line RPMI-8266. As shown by the long-term killing assay in FIG. 3, over a 48 hr period, the engineered CD38$^{-/-}$ NK cells eliminated the target cell in a similar manner as their wild-type control, demonstrating that CD38 is dispensable during target cell recognition and killing. Therefore, it was shown herein that the complete loss of CD38 in iPSC does not affect hematopoietic cell derivation or cytotoxicity of the derivative effector cells.

Figure 6:
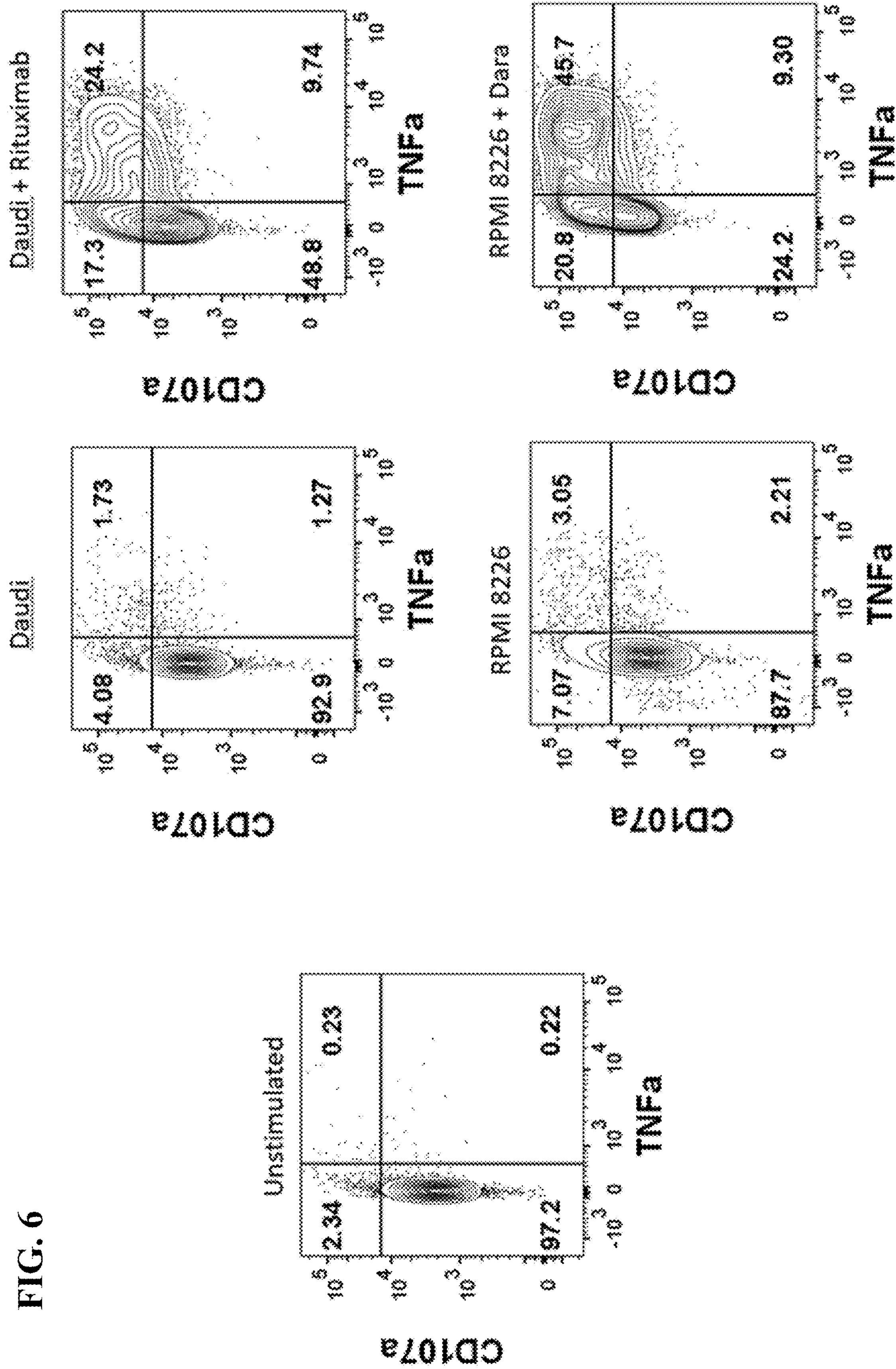
FIG. 6 demonstrates that $CD38^{-/-}$ iPSC derived NK cells have maintained the ADCC (antibody-dependent cell-mediated cytotoxicity) function when stimulated by tumor cell line RPMI-8266 in the presence of a CD38 antibody, daratumumab.
Figure 7:
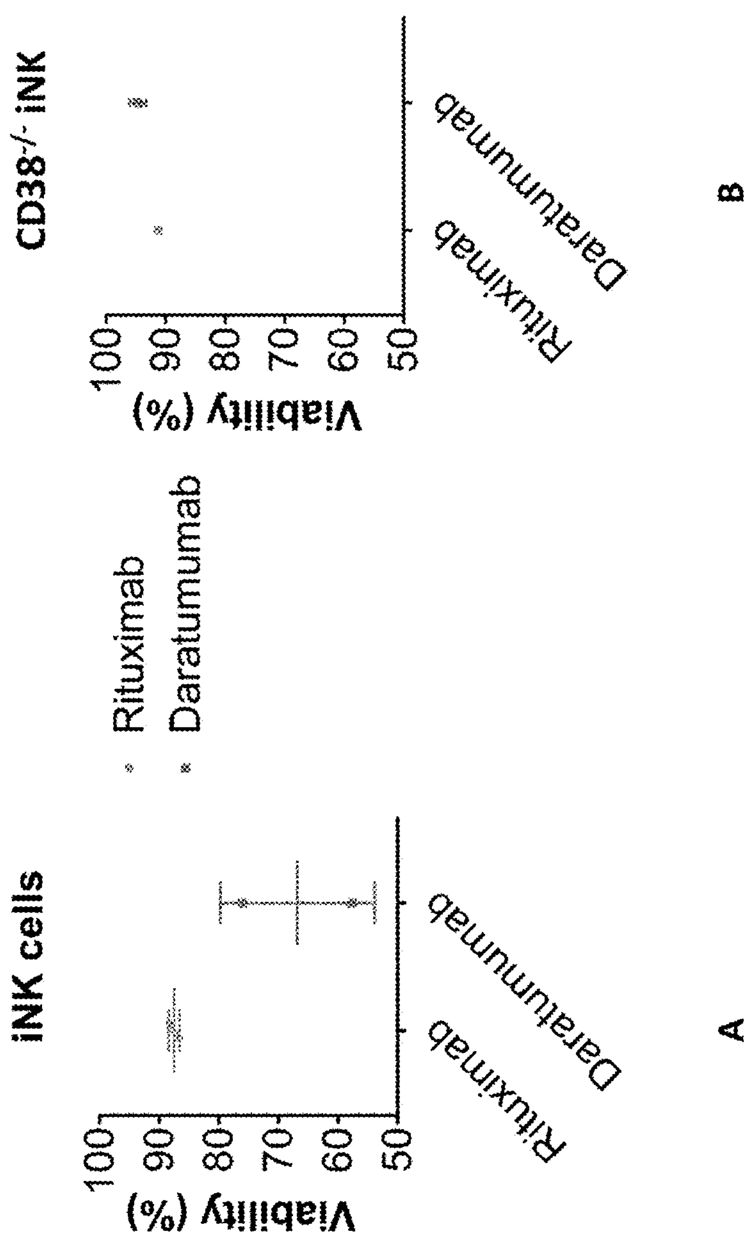
FIG. 7 demonstrates that, compared to iPSC-derived NK cells expressing CD38 (A), the viability of $CD38^{-/-}$ iPSC-derived NK cells (B) is maintained in culture with the presence of a CD38 antibody, daratumumab, for at least about 48 hrs.
Figure 8:
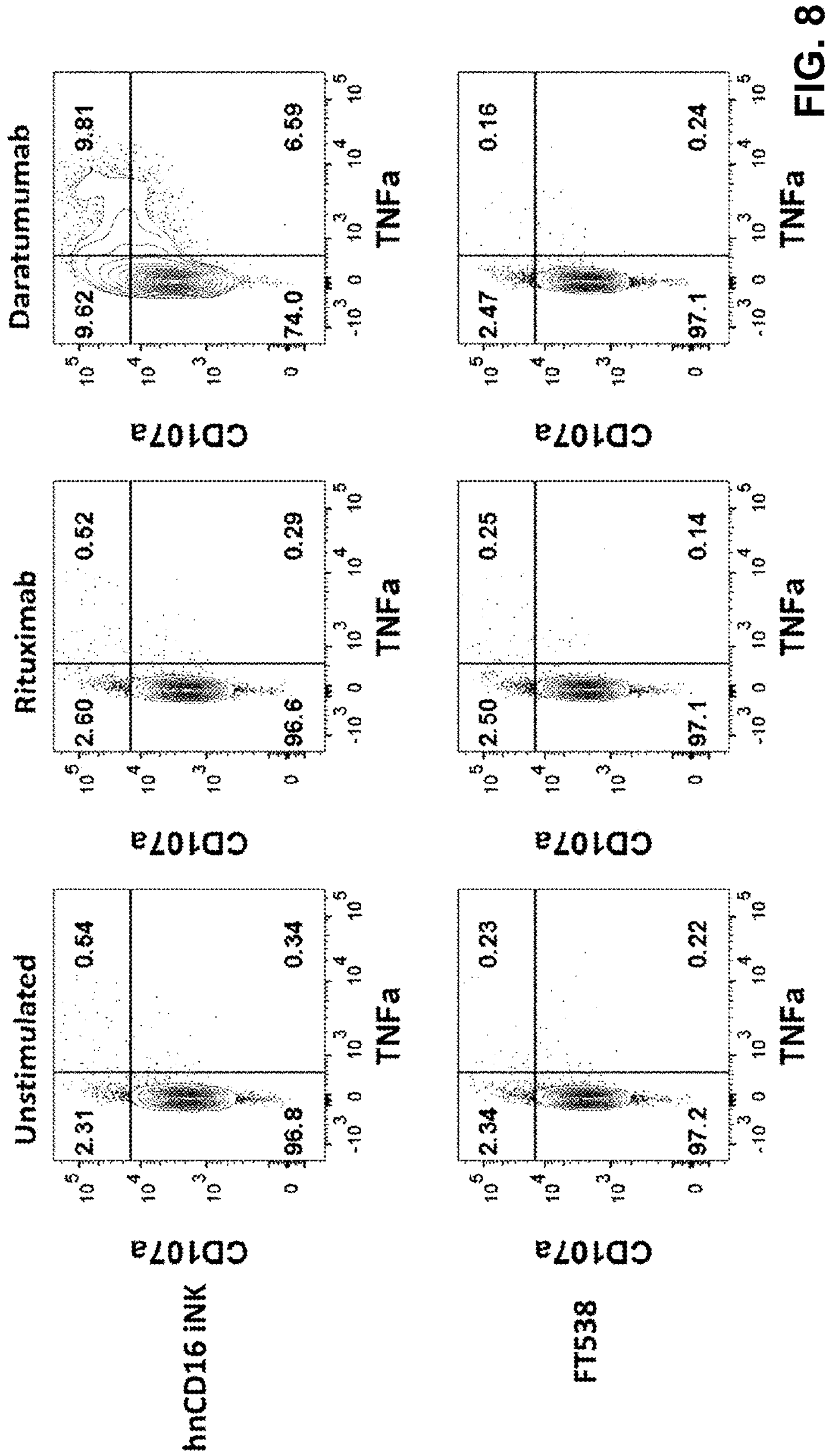
FIG. 8 demonstrates that the $CD38^{-/-}$ iPSC-derived NK cells (bottom panel) do not show degranulation and have less cytokine production than iNK cells expressing CD38 (top panel) when stimulated in the presence of a CD38 antibody, daratumumab.
Figure 9:
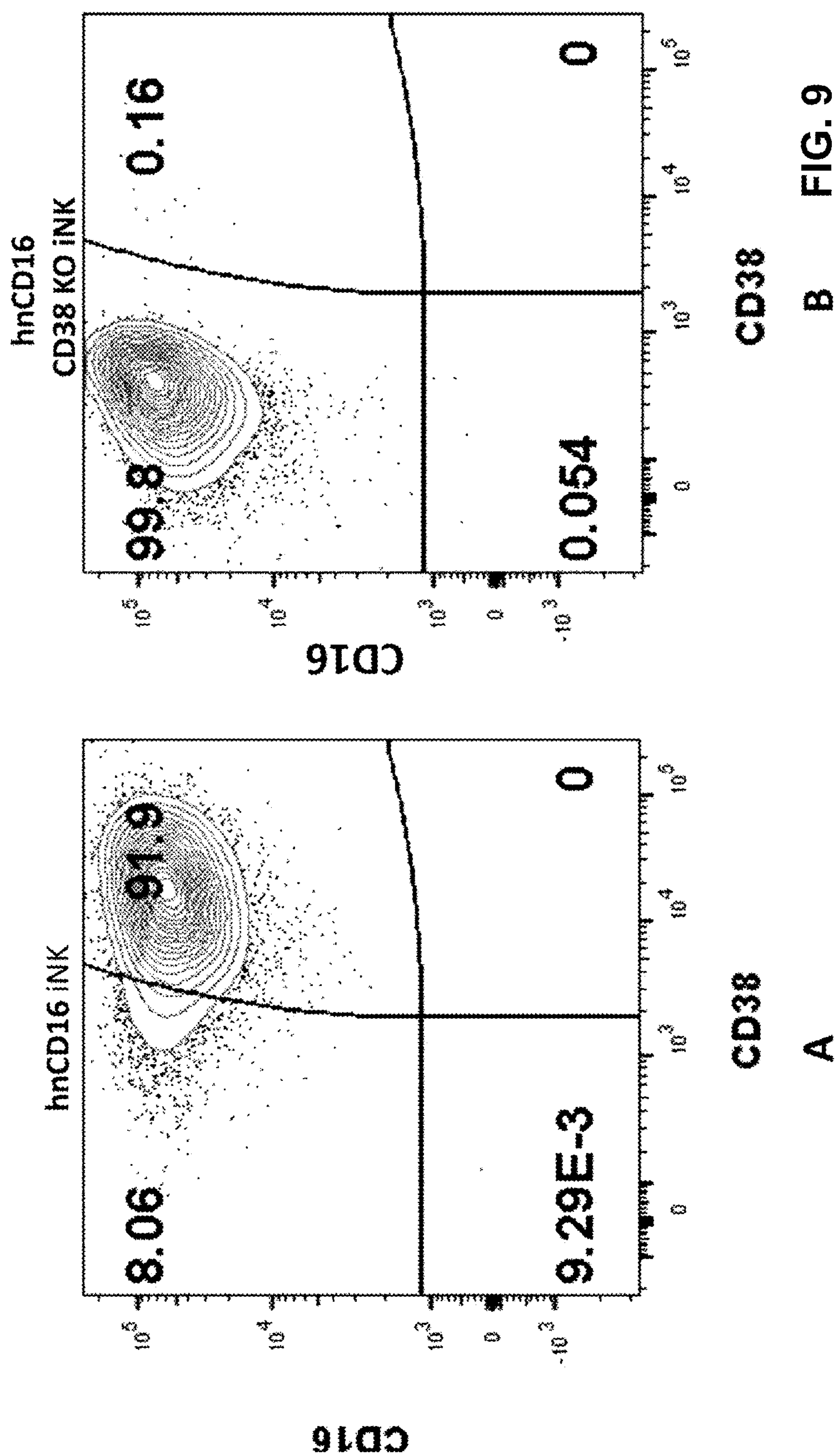
FIG. 9 shows the introduction of hnCD16 to iPSC-derived NK cells (A), and iPSC-derived NK cells having both the exogenous hnCD16 and CD38 knockout (B).

Daratumumab (Darzalex) is an anti-cancer drug. It binds to CD38, which is overexpressed in multiple myeloma cells. The daratumumab-mediated multiple myeloma cell killing is in part ADCC dependent and heavily reliant on NK effector cells. However, CD38 is also expressed in NK cells, resulting in daratumumab induced ADCC (fratricide)

towards NK cells, potentially significantly reducing the efficacy of daratumumab. Here, in FIG. 6, $CD38^{-/-}$ iPSC derived NK cells are shown to have maintained ADCC function when stimulated by tumor cell line RPMI-8266 in the presence of daratumumab. It is further shown in FIG. 7 that the viability of $CD38^{-/-}$ iPSC derived NK cells (FIG. 7B) is maintained in culture with the presence of daratumumab for at least about 48 hrs in comparison to iPSC derived NK cells expressing CD38 (FIG. 7A). Moreover, $CD38^{-/-}$ iPSC derived NK cells, as shown in FIG. 7, do not show degranulation and have less cytokine production than iNK cells expressing CD38 when stimulated in the presence of daratumumab.

Figure 4:
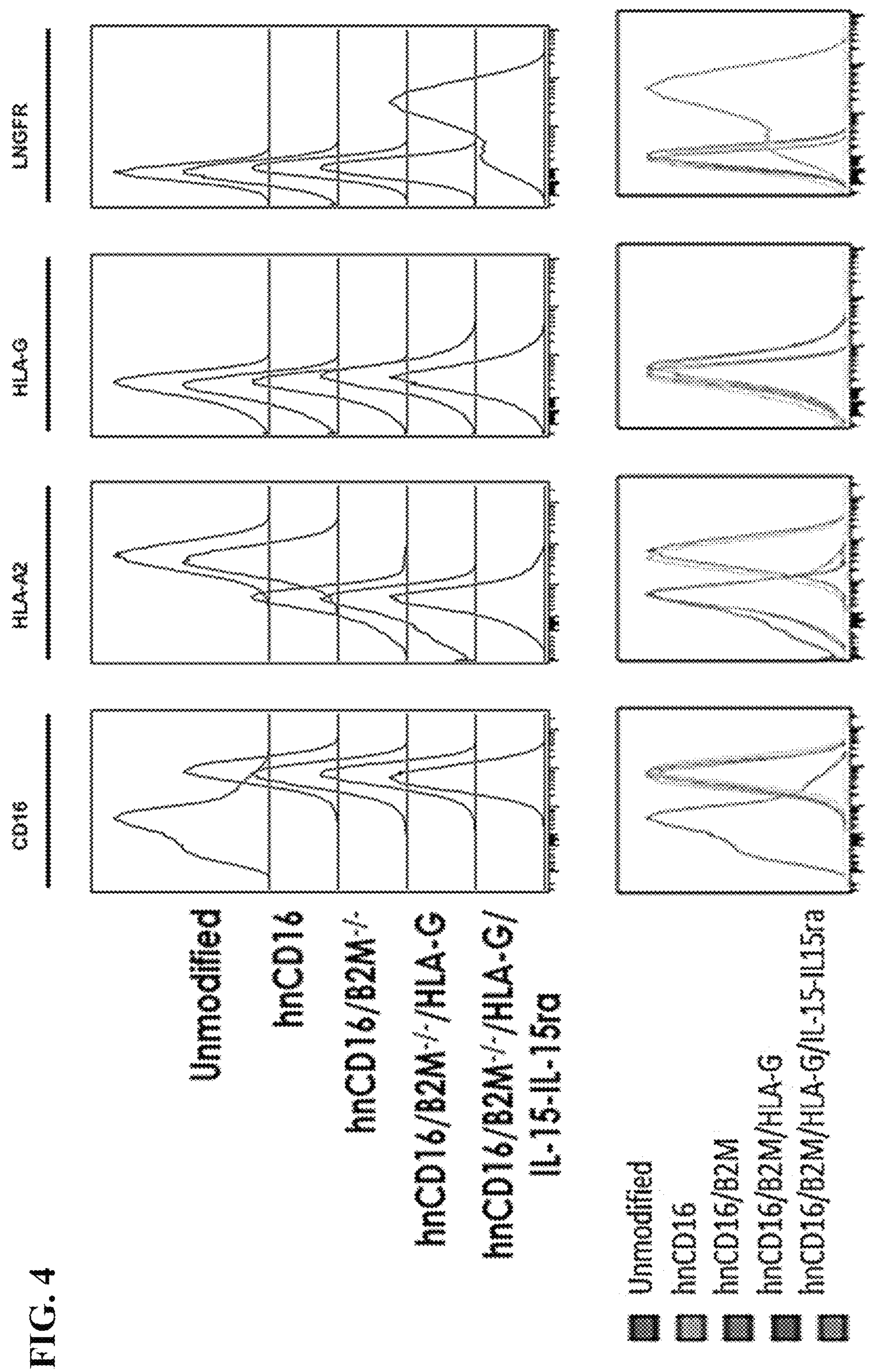
FIG. 4 is a graphic representation of flow cytometry of mature iPSC-derived NK cells that demonstrates stepwise engineering of hnCD16 expression, B2M knockout (loss of HLA-A2 expression), HLA-G expression, and IL-15/IL-15ra (LNGFR) construct expression.

Other than CD38 null, induced pluripotent stem cells were also serially engineered to obtain high affinity non-cleavable CD16 expression, loss of HLA-I by knocking out B2M gene, loss of HLA-II by knocking out CIITA, over-expression of the non-classical HLA molecule HLA-G, and expression of a linked IL15/IL15 receptor alpha construct. After each engineering step, iPSCs were sorted for the desired phenotype prior to the next engineering step. The engineered iPSCs can then be maintained in vitro or for derivative cell generation. FIG. 4 showed the hnCD16 expression, B2M knockout, HLA-G expression and IL15/IL15Rα expression in the iPSC-derived NK cells. FIG. 7 shows the introduction of hnCD16 in combination of CD38 knockout in the iPSC-derived NK cells. These data demonstrate that these genetically engineered modalities are maintained during hematopoietic differentiation without perturbing the in vitro directed development of the cell into a desired cell fate.

Figure 5:
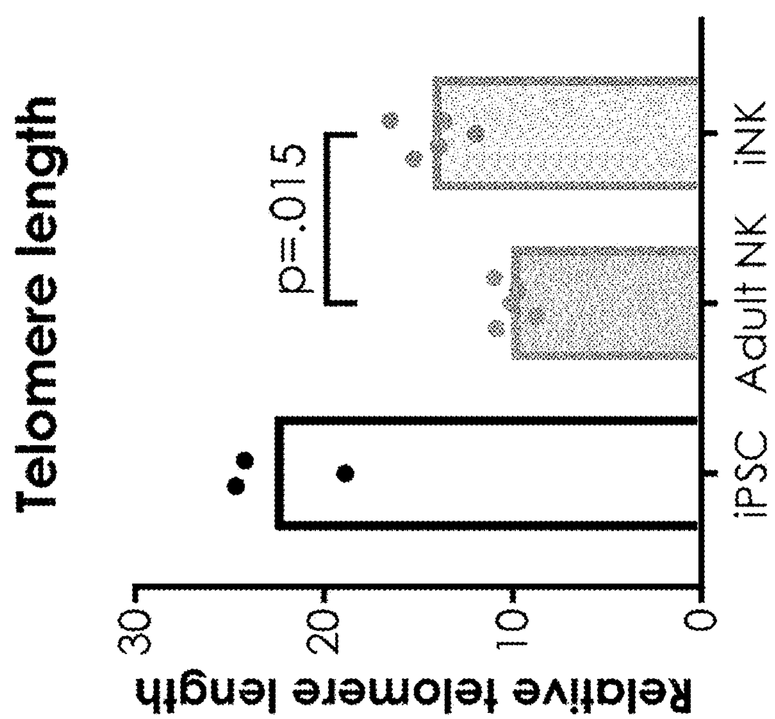
FIG. 5 is a graphic representation of telomere length determined by flow cytometry, and the mature derivative NK cells from iPSC maintain longer telomeres compared to adult peripheral blood NK cells.

Telomere shortening occurs with cellular aging and is associated with stem cell dysfunction and cellular senescence. It is shown here that the mature iNK cells maintain longer telomeres compared to adult peripheral bold NK cells. Telomere length was determined by flow cytometry for iPSC, adult peripheral blood NK cells, and iPSC-derived NK cells using the 1301 T cell leukemia line as a control (100%) with correction for the DNA index of Gori cells. As shown in FIG. 5, iPSC-derived NK cells maintain significantly longer telomere length when compared to adult peripheral blood NK cells (p=.105, ANOVA), representing greater proliferation, survival and persistence potential in the iPSC derived NK cells.

Example 4

Function Profiling of CD38 Null Derivative NK Cells

Figure 10:
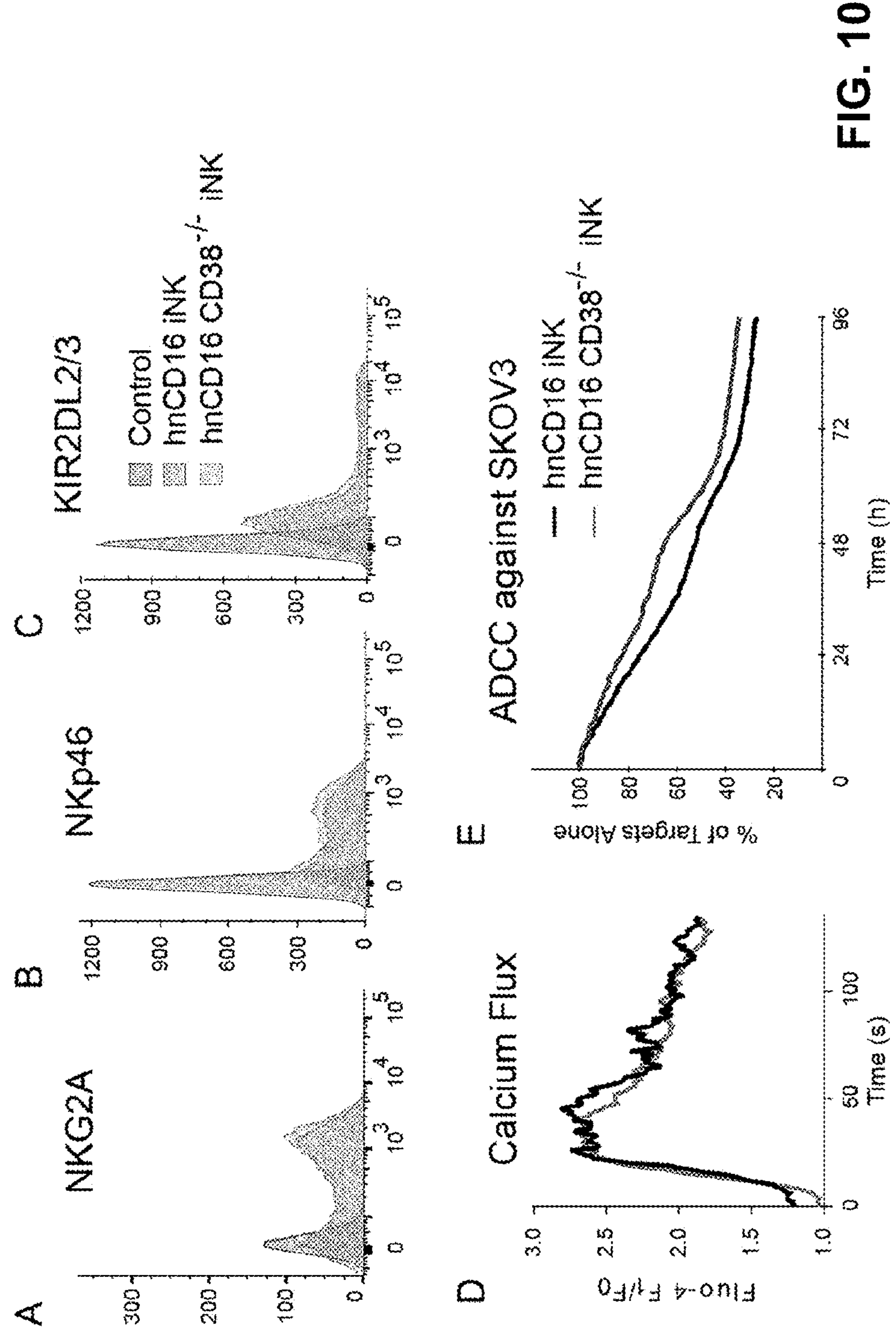
FIG. 10 shows phenotype and function analyses of hnCD16-$CD38^{-/-}$ derivative NK cells in comparison to hnCD16 derivative NK cells: (A) NKG2A expression by flow cytometry; (B) NKp46 expression by flow cytometry; (C) KIR2DL2/3 expression by flow cytometry; (D) calcium flux by flow; (E) ADCC against the HER2-expressing ovarian cell line SKOV3 by Incucyte™ live cell imaging.
Figure 11:
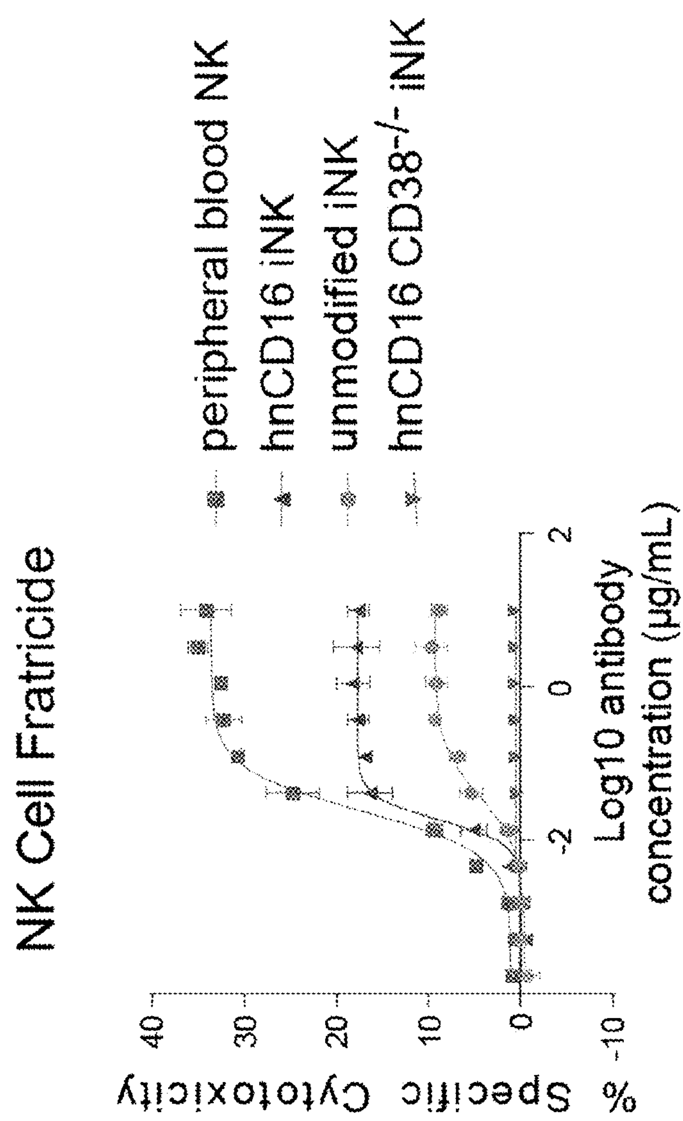
FIG. 11 shows the daratumumab-mediated NK cell fratricide in derivative NK cells with or without CD38 knockout in comparison to peripheral blood NK cells. Specific cytotoxicity of daratumumab against different NK cell populations was measured after a 4 hour incubation of indicated iNK cells in the presence of daratumumab with increasing concentration.

Phenotype of hnCD16 CD38−/− iNK cells, including NKG2A, NKp46 and KIR2DL2/3 expression, and calcium flux, was assessed, and the phenotype of the hnCD16 iNK is maintained following the CD38 knockout (FIG. 10 A-D). The ADCC function of hnCD16 iNK with CD38 knockout was examined against the HER2-expressing ovarian cell line SKOV3 by Incucyte live cell imaging, and CD38 knockout does not impact the ADCC function of hnCD16 iNK (FIG. 10 E). Next, specific cytotoxicity of daratumumab against different NK cell populations including: peripheral blood NK cells (with CD16 shedding), hnCD16 iNK cells (with high affinity and non-cleavable CD16), unmodified iNK cells (with low CD16 expression) and hnCD16 CD38−/− iNK cells, was measured after a 4 hour incubation of respective cell population with daratumumab at different concentrations. As shown in FIG. 11, CD38 deficiency protected hnCD16 CD38−/− iNK cells from fratricide mediated by increasing concentrations of daratumumab as compared to the other cell populations without CD38 knockout. Thus, CD38 loss prevents daratumumab-mediated NK cell fratricide in the presence of CD38 specific antibody.

Figure 12:
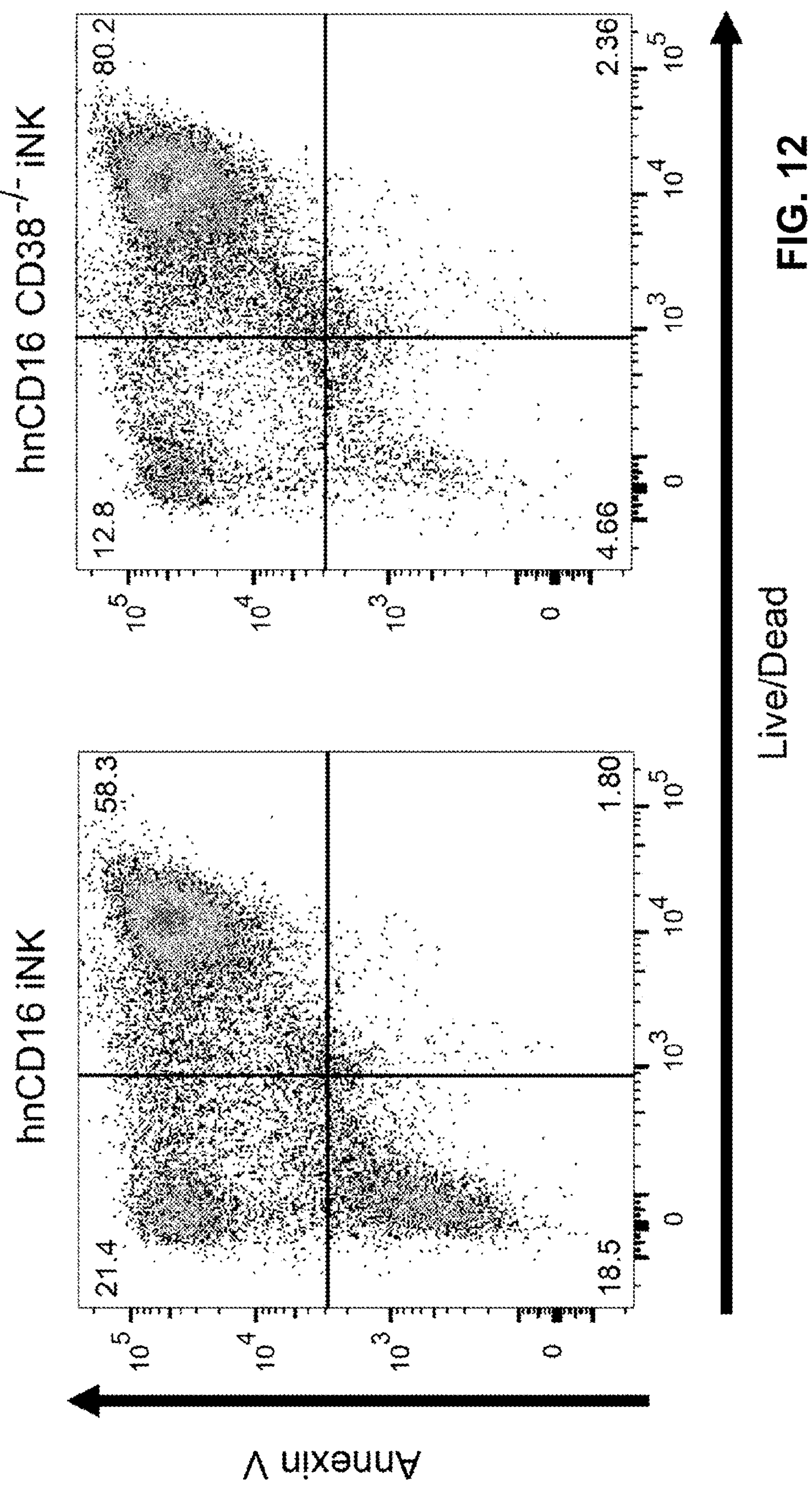
FIG. 12 shows enhanced daratumumab anti-myeloma activity mediated by CD38 null hnCD16 derivative NK cells. Indicated iNK cells were incubated with MM.1S myeloma target cells for 18 hours, after which, tumor cell viability was assessed by annexin V and a live/dead viability marker by flow cytometry.
Figure 13:
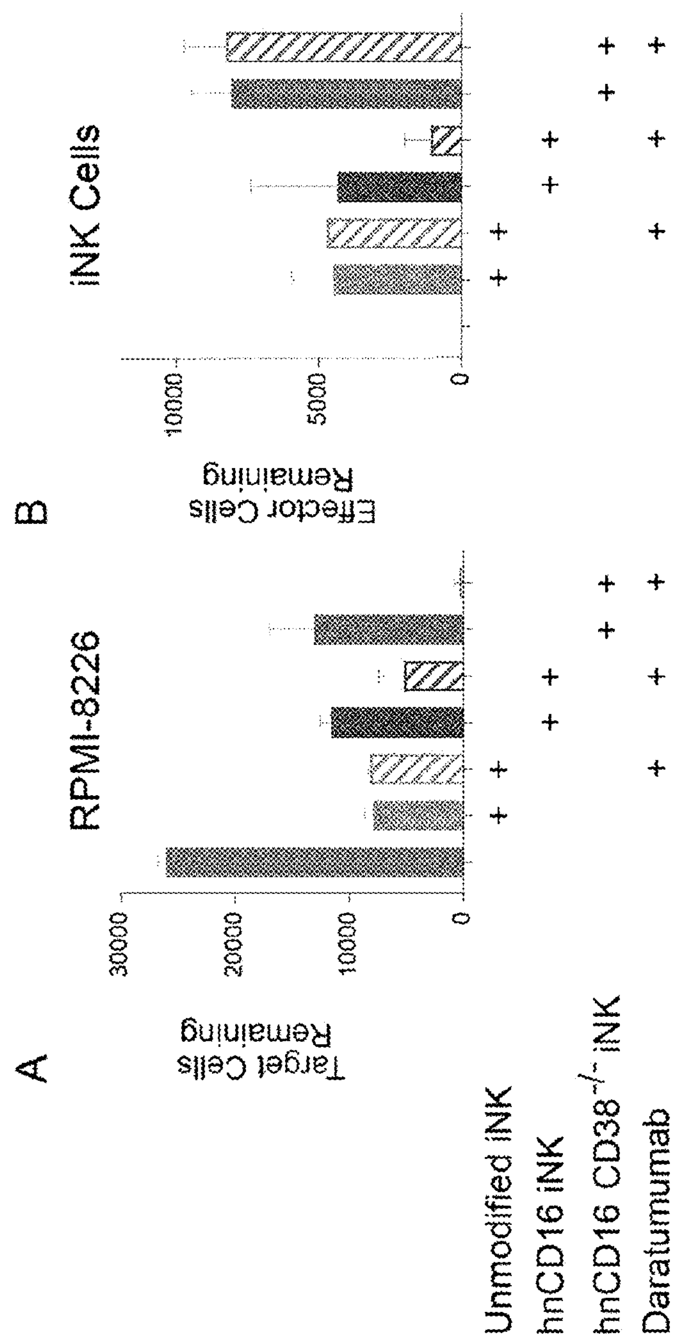
FIG. 13 shows that hnCD16 $CD38^{-/-}$ iNK Cells display enhanced long term anti-myeloma activity and persistence with daratumumab. (A) tumor cell clearance measured by the number of target cells remaining at the end of a 7-day cytotoxicity assay over a 7-day cytotoxicity assay against RMPI-8226 tumor spheroids; (B) lack of NK cell fratricide improved the survival of hnCD16 $CD38^{-/-}$ iNK over the 7-day cytotoxicity assay.
Figure 14:
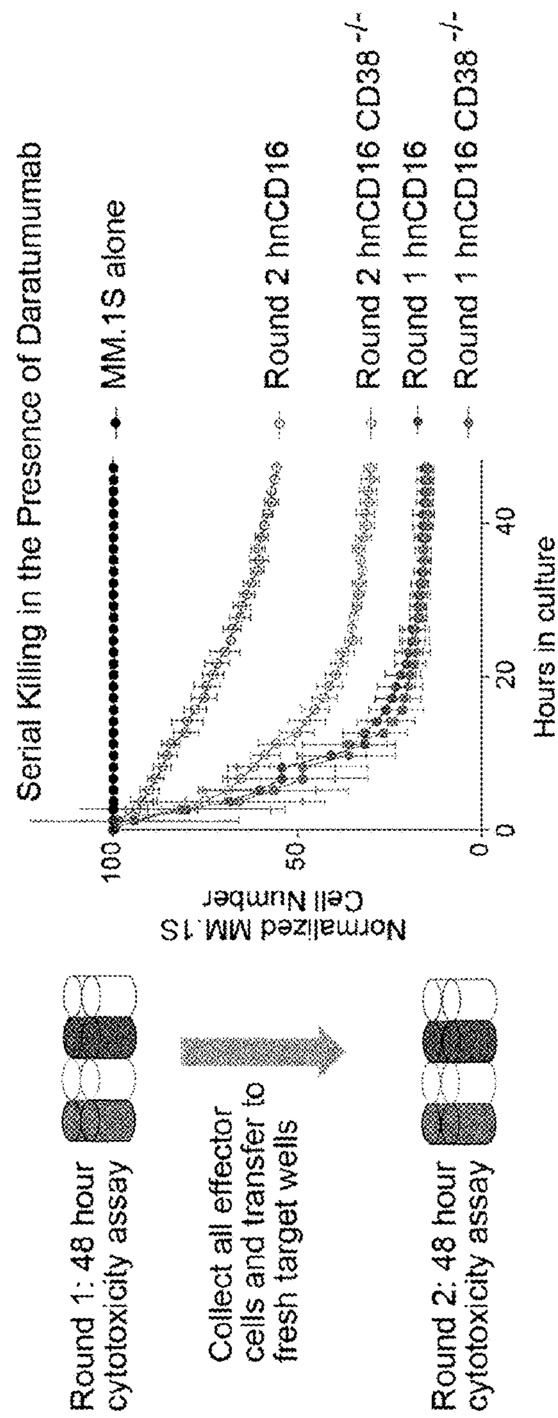
FIG. 14 shows that iNK Cells lacking CD38 possess more durable ADCC with increased serial killing potential in the presence of daratumumab.

To assess hnCD16 CD38−/− iNK cell cytotoxicity in comparison to hnCD16 iNK cells, each cell population was incubated with MM.1S myeloma target cells for 18 hours, and after which tumor cell viability was assessed by annexin V and a live/dead viability marker by flow cytometry. As shown in FIG. 12, the hnCD16 iNK cell mediate robust anti-myeloma activity with daratumumab is further augmented by CD38 loss. Further, over a 7-day cytotoxicity assay against RMPI-8226 tumor spheroids, hnCD16 CD38−/− iNK cells demonstrated superior tumor cell clearance with the presence of CD38 specific antibody, as measured by the number of target cells remaining at the end of the assay, and compared to hnCD16 iNK and unmodified iNK cells under the same condition (FIG. 13A). Moreover, lack of NK cell fratricide improved the survival of hnCD16 CD38−/− iNK cells as shown by improved persistence of these cells over the 7-day cytotoxicity assay demonstrated in FIG. 13B. Therefore, hnCD16 CD38−/− iNK cells display enhanced long term anti-myeloma activity and persistence with CD38 specific antibody such as daratumumab. hnD16 iNK cells lacking CD38 also demonstrate more durable ADCC with increased serial killing potential in the presence of CD38 specific antibody, as shown in FIG. 14. In this assay, hnCD16 or hnCD16 CD38−/− iNK cells were incubated with MM.1S myeloma target cells with daratumumab for 48 hours (Stimulation Round 1), and MM.1S cell number was quantified by Incucyte™ imaging. After 48 hours, effector cells were removed and transferred to new target cells for a second round of stimulation and target cell killing with daratumumab (Stimulation Round 2). (FIG. 14)

In light of the above, it was discovered that targeted knockout of CD38 does not affect derivative NK cell phenotype nor general cell function, and the resultant CD38 deficient derivative NK cells are protected from CD38 specific antibody, daratumumab, for example, mediated fratricide. The synergy between hnCD16 and CD38−/− provides the derivative NK cell enhanced antimyeloma activity and durable ADCC in combination with CD38 specific antagonist, including monoclonal antibody such as daratumumab. Based on these findings, a clinical strategy is proposed for the combination of off-the-shelf hnCD16CD38−/− iNK cells with daratumumab to overcome NK cell depleting effects of CD38 targeted agents and to improve myeloma patient outcome.

Example 5

Use of CD38 Specific Antagonist to Protect Allogenic Effector Cells from Allorejection iNK cells engineered with enhanced CD16 efficacy and CD38 removed are resistant to CD38-targeted antibody-induced fratricide and more potently mediate anti-myeloma activity in combination with daratumumab. It is further provided herein that due to the fact that CD38 is upregulated on activated lymphocytes such as T or B cells, by suppressing activation of these lymphocytes using CD38 specific antagonist, including monoclonal antibodies, in the recipient of allogeneic effector cells deficient in CD38, the allorejection against these effector cells would be reduced and/or prevented and thereby increasing effector cell survival and persistency. To show the feasibility of this strategy, a Mixed Lymphocyte Reaction (MLR, i.e., co-incubation of effector cell product and allogeneic PBMC) is performed to test the longevity of derivative effector cells of this invention in an allogeneic setting in the context of CD38 knockout and in the presence or absence of anti-CD38 monoclonal antibody (for example, daratumumab).

The hnCD16+ iNK cell populations (with and without CD38KO) are labelled with an intracellular dye (Celltrace Violet™ or similar Incucyte™ compatible reagent) immediately prior to assay. Different concentrations of hnCD16+ and hnCD16 CD38−/− iNK cells are incubated with a fixed number of PBMC from random healthy donors (n=3-4, not pooled), in the presence or absence of daratumumab (at effective concentration, titrated prior to assay). Survival of iNK cells in each population is monitored by Incucyte™ over time in long term culture. Survival is also monitored by flow cytometry, where a staining panel is employed to additionally trace CD38 upregulation on PBMC subpopulations, and clearance of PBMC subpopulations by iNK cells based on daratumumab mediated ADCC. Total clearance of iNK cells as control is achieved using Venetoclax (MCL-1 inhibitor, for specific removal of NK cells).

An increased longevity of hnCD16 CD38KO iNK cells versus wildtype hnCD16 iNK cells in the presence of anti-CD38, and associated clearance of CD38+ subpopulations (peripheral NK cells, activated B cells and T cells) from the PBMC samples indicate the capability of CD38 specific antagonist in suppressing the activated peripheral T or B cells by targeting their upregulated CD38, thereby reducing allorejection against the allogenic effecter cells by these activated peripheral T or B cells in the recipient of the effector cells comprising hnCD16 and CD38−/−, as provided herein. The CD38 specific antagonist is a CD38 specific antibody, a CD38 specific engager or a CD38 chimeric antigen receptor (CAR).

Figure 15:
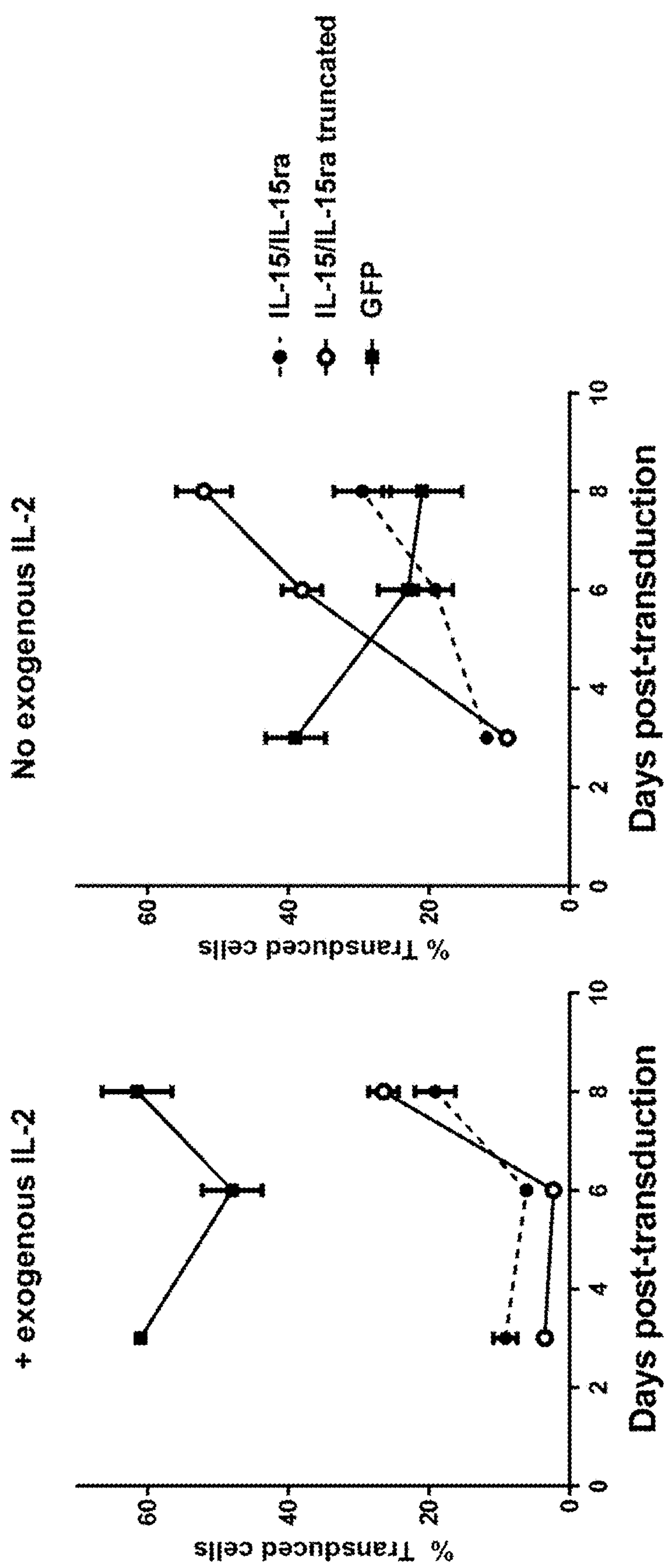
FIG. 15 shows that iNK cells with transduced with full-length IL15/IL15Rα fusion construct (filled circles; positive control), or a truncated IL15/IL15Rα fusion construct without cytoplasmic signaling domain (open circles) had a survival advantage compared to non-transduced or GFP transduced cells in the same cultures independent of exogenous soluble IL2. A: in the presence of exogenous IL2; B: without the presence of exogenous IL2.

In addition, the expression of exogenous truncated IL15/IL15Rα fusion protein lacking the intracellular domain of IL15Rα was shown to support the survival of iPSC derived NK cells in vitro independent of addition of soluble, exogenous IL2. The IL15Rα without its intracellular domain was fused to IL15 at the C-terminus through a linker to generate a truncated IL15/IL15Rα fusion construct having no signaling domain (or called "IL154" in this application). Exemplary IL15Δ as provide herein includes those having a structure such as the Design 3 or 4 of FIG. 1. As shown in FIG. 15, iNK cells were transduced with lentiviral overexpression vectors expressing either GFP (squares; negative control), full-length IL15/IL15Rα fusion construct (filled circles; positive control; Design 2 of FIG. 1), or a truncated IL15/IL15Rα fusion construct (open circles; Design 3 of FIG. 1). Neither of the IL15 constructs nor GFP showed enrichment in the presence of exogenous IL2 (FIG. 15A), indicating that transduced cells survived at comparable rates with non-transduced cells. In the absence of exogenous IL2, cells transduced with either IL15/IL15Rα fusion construct were enriched over time while GFP transduced cells were not, indicating that without IL2, cells transduced with either IL15/IL15Rα construct had a survival advantage compared to non-transduced cells in the same cultures (FIG. 15B). Moreover, since the intracellular domain of IL15Rα has been deemed as critical for the receptor to express in the IL15 responding cells and for the cells to expand and function in response, it is surprising that the intracellular domain truncated IL15/IL15Rα fusion construct not only is stably expressed in the transduced iNK cell, but also supports iNK cell at a higher expansion rate than the full-length IL15/IL15Rα fusion construct, as shown in FIG. 15B. As such, the IL15Δ as provided herein is capable of expressing and maintaining IL15 in a membrane-bound form, and can replace a full-length IL15/IL15Rα fusion protein to provide the trans-presentation of IL15 in a cell. Without fully understand the underlying mechanism, removing the intracellular domain of IL15R seems to have given the responding cells additional vigor, fitness, or certain advantage, in survival, expansion and persistence, possibly by entirely eliminating cis-presentation and/or any other potential signal transduction pathways mediated by a normal IL15R through its intracellular domain.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A cell or a population thereof, wherein (i) the cell is an NK cell obtained from differentiating a human induced pluripotent cell (iPSC), a human clonal iPSC, or a human iPSC cell line cell; and (ii) the cell comprises a CD38 knockout.

2. The cell or population thereof of claim 1, wherein the NK cell comprises longer telomeres in comparison to human NK cells obtained from peripheral blood, umbilical cord blood, or other donor blood.

3. The cell or population thereof of claim 1, wherein the NK cell comprises one or more of:

(i) B2M null or low;

(ii) CIITA null or low;

(iii) introduced expression of HLA-G or non-cleavable HLA-G;

(iv) a high affinity non-cleavable CD 16 (hnCD 16) or a variant thereof;

(v) a chimeric antigen receptor (CAR);

(vi) a partial or full peptide of a cell surface expressed exogenous cytokine and/or a partial or full peptide of a cytokine receptor;

(vii) deletion or reduced expression in at least one of TAP1, TAP2, Tapasin, NLRC5, PD1, LAG3, TIM3, RFXANK, RFX5, RFXAP, or any gene in the chromosome 6p21 region; or (viii) introduced or increased expression in at least one of HLA-E, 41 BBL, CD3, CD4, CD8, CD16, CD47, CD113, CD131, CD137, CD80, PDL1, $A_{2A}$R, CAR, TCR, Fc receptor, an engager, or surface triggering receptor for coupling with bi- or multi-specific or universal engagers.

4. The cell or population thereof of claim 1, wherein the NK cell has at least one of the following characteristics comprising:

(i) improved persistency and/or survival;

(ii) increased resistance to native immune cells;

(iii) increased cytotoxicity;

(iv) improved tumor penetration;

(v) enhanced ADCC;

(vi) enhanced ability in migrating, and/or activating or recruiting bystander immune cells, to tumor sites;

(vii) enhanced ability to reduce tumor immunosuppression;

(viii) improved ability in rescuing tumor antigen escape; or (ix) reduced fratricide, in comparison to human NK cells obtained from peripheral blood, umbilical cord blood, or other donor blood.

5. The cell or population thereof of claim 3, wherein the NK cell comprises a high affinity non-cleavable CD16 (hnCD16) or a variant thereof.

6. The cell or population thereof of claim 5, wherein the high affinity non-cleavable CD16 (hnCD16) or a variant thereof comprises at least one of:

(a) F176V and S197P in ectodomain domain of CD16;

(b) a full or partial ectodomain originated from CD64; or (c) a transmembrane domain, intracellular stimulatory domain, and/or signaling domain from a same or different non-CD16 polypeptide.

7. The cell or population thereof of claim 6, wherein (a) the transmembrane domain of the hnCD16 or variant thereof is derived from CD3D, CD3E, CD3G, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor (TCR) polypeptide;

(b) the stimulatory domain of the hnCD16 or variant thereof is derived from CD27, CD28, 4-1BB, OX40, ICOS, PD-1, LAG-3, 2B4, BTLA, DAP10, DAP12, CTLA-4, or NKG2D polypeptide;

(c) the signaling domain of the hnCD16 or variant thereof is derived from CD3ζ, 2B4, DAP10, DAP12, DNAM1, CD137 (41BB), IL21, IL7, IL12, IL15, NKp30, NKp44, NKp46, NKG2C, or NKG2D polypeptide; or (d) the transmembrane domain of the hnCD16 or variant thereof is derived from NKG2D, the stimulatory domain of the hnCD16 or variant thereof is derived from 2B4, and the signaling domain of the hnCD16 or variant thereof is derived from CD3ζ.

8. The cell or population thereof of claim 3, wherein the NK cell further comprises a chimeric antigen receptor (CAR).

9. The cell or population thereof of claim 8, wherein the CAR is:

(i) NK cell specific; or (ii) co-expressed with a partial or full peptide of a cell surface expressed exogenous cytokine or a receptor thereof, optionally in separate constructs or in a bi-cistronic construct.

10. The cell or population thereof of claim 8, wherein (i) the CAR is inserted at one of the loci comprising AAVS1, CCR5, ROSA26, collagen, HTRP, H11, beta-2 microglobulin, GAPDH, TCR, CD38, or RUNX1a; or (ii) the CAR is inserted at a CD38 locus, and wherein CD38 is knocked out by the CAR insertion.

11. The cell or population thereof of claim 3, wherein the NK cell comprises a partial or full peptide of a cell surface expressed exogenous cytokine and/or a partial or full peptide of a cytokine receptor, wherein (a) the partial or full peptide of a cell surface expressed exogenous cytokine is fused to the partial or full peptide of a cytokine receptor;

(b) the partial or full peptide of a cell surface expressed exogenous cytokine and/or a receptor thereof is transiently expressed;

(c) the partial or full peptide of a cell surface expressed exogenous cytokine and/or a receptor thereof is at least one of IL2, IL4, IL6, IL7, IL9, IL10, IL11, IL12, IL15, IL18 or IL21, and/or a receptor thereof;

(d) the partial or full peptide of a cell surface expressed exogenous cytokine is IL15 and wherein the NK cell comprises at least one of:

(i) co-expression of IL15 and IL15α by using a self-cleaving peptide;

(ii) a partial or full peptide of IL15 fused with a partial or full peptide of IL15Rα;

(iii) a partial or full peptide of IL15 fused with a partial peptide of IL15Rα, wherein the partial peptide of IL15Rα comprises a truncated intracellular domain;

(iv) a partial or full peptide of IL15 fused with a Sushi domain of IL15Rα;

(v) a partial or full peptide of IL15 fused with a partial or full peptide of IL15Rβ;

(vi) a partial or full peptide of IL15 fused with a partial or full peptide of common receptor γC, wherein the common receptor γC is native or modified; or (vii) a homodimer of a partial or full peptide of IL15Rβ.

12. The cell or population thereof of claim 4, (a) wherein the NK cell is capable of recruiting T cells to tumor sites, and (b) wherein the NK cell is capable of reducing tumor immunosuppression in the tumor site.

13. The cell or population thereof of claim 12, wherein the NK cell expresses one or more checkpoint inhibitors.

14. The cell or population thereof of claim 13, wherein the one or more checkpoint inhibitors are antagonists to one or more checkpoint molecules comprising PD-1, PDL-1, TIM-3, TIGIT, LAG-3, CTLA-4, 2B4, 4-1 BB, 4-1 BBL, A2aR, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR.

15. The cell or population thereof of claim 12, wherein the NK cell is in a composition comprising one or more checkpoint inhibitors, and wherein the one or more checkpoint inhibitors comprise:

(a) one or more of atezolizumab, avelumab, durvalumab, ipilimumab, 1PH4102, IPH43, IPH33, lirimumab, monalizumab, nivolumab, pembrolizumab, or a derivative thereof; or (b) at least one of atezolizumab, nivolumab, and pembrolizumab.

16. The cell or population thereof of claim 1, wherein the NK cell comprises a polynucleotide encoding a fusion protein of IL15 and a truncated IL15Rα, and wherein the fusion protein comprises (a) amino acids 19-151 and 178-379 of SEQ ID NO:17;

(b) amino acids 19-151 and 178-242 of SEQ ID NO:19; or (c) amino acids 19-151 and 178-375 of SEQ ID NO:21.

17. A composition comprising the cell or population thereof of claim 1.

18. The composition of claim 17, further comprising one or more therapeutic agents.

19. The composition of claim 18, wherein the one or more therapeutic agents comprise a peptide, a cytokine, a checkpoint inhibitor, a mitogen, a growth factor, a small RNA, a dsRNA (double stranded RNA), mononuclear blood cells, feeder cells, feeder cell components or replacement factors thereof, a vector comprising one or more polynucleotides of interest, an antibody, a chemotherapeutic agent, a radioactive moiety, or an immunomodulatory drug (IMiD).

20. The composition of claim 19, wherein (i) the checkpoint inhibitor comprises:

(a) one or more antagonists checkpoint molecules comprising PD-1, PDL-1, TIM-3, TIGIT, LAG-3, CTLA-4, 2B4, 4-1 BB, 4-1 BBL, A2aR, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR;

(b) one or more of atezolizumab, avelumab, durvalumab, ipilimumab, IPH4102, IPH43, IPH33, lirimumab, monalizumab, nivolumab, pembrolizumab, or a derivative thereof; or (c) at least one of atezolizumab, nivolumab, and pembrolizumab; or (ii) the therapeutic agents comprise one or more of venetoclax, azacitidine, and pomalidomide; or (iii) the antibody:

(a) comprises an anti-CD20, anti-HER2, anti-CD52, anti-EGFR, anti-CD123, anti-GD2, anti-PDL1, and/or anti-CD38 antibody;

(b) comprises daratumumab, isatuximab, or MOR202, or a humanized or Fc modified variant thereof, and wherein the NK cell optionally expresses hnCD16 or a variant thereof; or (c) is a checkpoint inhibitor.

21. A cell or a population thereof, wherein (i) the cell comprises a CD38 knockout;

(ii) the cell is (a) a human NK cell or human T cell; and (b) is obtained from differentiating a human induced pluripotent stem cell (iPSC), a human clonal iPSC, or a human iPSC cell line cell; and (iii) the cell (A) is in a composition comprising one or more checkpoint inhibitors, or (B) expresses one or more checkpoint inhibitors.

22. A population of cells, wherein:

(i) the cells comprise a CD38 knockout;

(ii) the cells are human hematopoietic cells obtained from differentiating human induced pluripotent cells (iPSCs), human clonal iPSCs, or human induced pluripotent stem cell line cells; and (iii) the population of cells comprises a longer average telomere length in comparison to their native counterpart cells obtained from peripheral blood, umbilical cord blood, or other donor blood.

* * * * *

UNITED STATES PATENT AND TRADEMARK OFFICE

CERTIFICATE OF CORRECTION

PATENT NO. : 10,927,346 B2
APPLICATION NO. : 16/576411
DATED : February 23, 2021
INVENTOR(S) : Bahram Valamehr et al.

It is certified that error appears in the above-identified patent and that said Letters Patent is hereby corrected as shown below:

In the Claims

Column 107, Line 33, In Claim 3, please delete "CD 16 (hnCD 16)" and insert --CD16 (hnCD16)--

Column 107, Line 45, In Claim 3, please delete "41 BLL" and insert --4-1BLL--

Column 109, Line 41, In Claim 14, please delete "4-1 BB" and insert --4-1BB--

Column 109, Line 41, In Claim 14, please delete "4-1 BBL" and insert --4-1BBL--

Column 109, Line 41, In Claim 14, please delete "A2aR" and insert --$A_{2a}R$--

Column 109, Line 52, In Claim 15, please delete "1PH4102" and insert --IPH4102--

Column 110, Line 19, In Claim 20, please delete "4-1 BB" and insert --4-1BB--

Column 110, Line 19, In Claim 20, please delete "4-1 BBL" and insert --4-1BBL--

Column 110, Line 19, In Claim 20, please delete "A2aR" and insert --$A_{2a}R$--

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 21

<210> SEQ ID NO 1
<211> LENGTH: 19
<212> TYPE: DNA
<213> ORGANISM: Homo sapiens
<220> FEATURE:
<223> OTHER INFORMATION: targeting sequence for CD38 Exon 1 knockout
```

(CD38-gNA-1A)

<400> SEQUENCE: 1
ttgacgcatc gcgccagga 19

<210> SEQ ID NO 2
<211> LENGTH: 19
<212> TYPE: DNA
<213> ORGANISM: Homo sapiens
<220> FEATURE:
<223> OTHER INFORMATION: targeting sequence for CD38 Exon 1 knockout (CD38-gNA-1B)

<400> SEQUENCE: 2
attcatcctg agatgaggt 19

<210> SEQ ID NO 3
<211> LENGTH: 19
<212> TYPE: DNA
<213> ORGANISM: Homo sapiens
<220> FEATURE:
<223> OTHER INFORMATION: targeting sequence for CD38 Exon 1 knockout (CD38-gNA-2A)

<400> SEQUENCE: 3
actgacgcca agacagagt 19

<210> SEQ ID NO 4
<211> LENGTH: 19
<212> TYPE: DNA
<213> ORGANISM: Homo sapiens
<220> FEATURE:
<223> OTHER INFORMATION: targeting sequence for CD38 Exon 1 knockout (CD38-gNA-2B)

<400> SEQUENCE: 4
ctggtcctga tcctcgtcg 19

<210> SEQ ID NO 5
<211> LENGTH: 19
<212> TYPE: DNA
<213> ORGANISM: Homo sapiens
<220> FEATURE:
<223> OTHER INFORMATION: targeting sequence for CD38 Exon 1 knockout (CD38-gNA-3A)

<400> SEQUENCE: 5
tcctagagag ccggcagca 19

<210> SEQ ID NO 6
<211> LENGTH: 19
<212> TYPE: DNA
<213> ORGANISM: Homo sapiens
<220> FEATURE:
<223> OTHER INFORMATION: targeting sequence for CD38 Exon 1 knockout (CD38-gNA-3B)

<400> SEQUENCE: 6
ggagagccca actctgtct 19

<210> SEQ ID NO 7
<211> LENGTH: 340
<212> TYPE: PRT
<213> ORGANISM: Artificial Sequence
<220> FEATURE:
<223> OTHER INFORMATION: 340 a.a. CD64 domain-based construction

<400> SEQUENCE: 7

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Tyr Gln Val Ser Phe Cys Leu Val Met Val Leu Leu
    290                 295                 300

Phe Ala Val Asp Thr Gly Leu Tyr Phe Ser Val Lys Thr Asn Ile Arg
305                 310                 315                 320

Ser Ser Thr Arg Asp Trp Lys Asp His Lys Phe Lys Trp Arg Lys Asp
                325                 330                 335

Pro Gln Asp Lys
            340
```

<210> SEQ ID NO 8
<211> LENGTH: 336
<212> TYPE: PRT
<213> ORGANISM: Artificial Sequence
<220> FEATURE:
<223> OTHER INFORMATION: 336 a.a. CD64 exon-based construction

<400> SEQUENCE: 8

```
Met Trp Phe Leu Thr Thr Leu Leu Leu Trp Val Pro Val Asp Gly Gln
```

-continued 1 5 10 15

Val Asp Thr Thr Lys Ala Val Ile Thr Leu Gln Pro Pro Trp Val Ser
20 25 30

Val Phe Gln Glu Glu Thr Val Thr Leu His Cys Glu Val Leu His Leu
35 40 45

Pro Gly Ser Ser Ser Thr Gln Trp Phe Leu Asn Gly Thr Ala Thr Gln
50 55 60

Thr Ser Thr Pro Ser Tyr Arg Ile Thr Ser Ala Ser Val Asn Asp Ser
65 70 75 80

Gly Glu Tyr Arg Cys Gln Arg Gly Leu Ser Gly Arg Ser Asp Pro Ile
85 90 95

Gln Leu Glu Ile His Arg Gly Trp Leu Leu Leu Gln Val Ser Ser Arg
100 105 110

Val Phe Thr Glu Gly Glu Pro Leu Ala Leu Arg Cys His Ala Trp Lys
115 120 125

Asp Lys Leu Val Tyr Asn Val Leu Tyr Tyr Arg Asn Gly Lys Ala Phe
130 135 140

Lys Phe Phe His Trp Asn Ser Asn Leu Thr Ile Leu Lys Thr Asn Ile
145 150 155 160

Ser His Asn Gly Thr Tyr His Cys Ser Gly Met Gly Lys His Arg Tyr
165 170 175

Thr Ser Ala Gly Ile Ser Val Thr Val Lys Glu Leu Phe Pro Ala Pro
180 185 190

Val Leu Asn Ala Ser Val Thr Ser Pro Leu Leu Glu Gly Asn Leu Val
195 200 205

Thr Leu Ser Cys Glu Thr Lys Leu Leu Leu Gln Arg Pro Gly Leu Gln
210 215 220

Leu Tyr Phe Ser Phe Tyr Met Gly Ser Lys Thr Leu Arg Gly Arg Asn
225 230 235 240

Thr Ser Ser Glu Tyr Gln Ile Leu Thr Ala Arg Arg Glu Asp Ser Gly
245 250 255

Leu Tyr Trp Cys Glu Ala Ala Thr Glu Asp Gly Asn Val Leu Lys Arg
260 265 270

Ser Pro Glu Leu Glu Leu Gln Val Leu Gly Leu Phe Phe Pro Pro Gly
275 280 285

Tyr Gln Val Ser Phe Cys Leu Val Met Val Leu Leu Phe Ala Val Asp
290 295 300

Thr Gly Leu Tyr Phe Ser Val Lys Thr Asn Ile Arg Ser Ser Thr Arg
305 310 315 320

Asp Trp Lys Asp His Lys Phe Lys Trp Arg Lys Asp Pro Gln Asp Lys
325 330 335

<210> SEQ ID NO 9
<211> LENGTH: 335
<212> TYPE: PRT
<213> ORGANISM: Artificial Sequence
<220> FEATURE:
<223> OTHER INFORMATION: 335 a.a. CD64 exon-based construction

<400> SEQUENCE: 9

Met Trp Phe Leu Thr Thr Leu Leu Leu Trp Val Pro Val Asp Gly Gln
1 5 10 15

Val Asp Thr Thr Lys Ala Val Ile Thr Leu Gln Pro Pro Trp Val Ser
20 25 30

Val Phe Gln Glu Glu Thr Val Thr Leu His Cys Glu Val Leu His Leu

```
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Phe Phe Pro Pro Gly Tyr
        275                 280                 285

Gln Val Ser Phe Cys Leu Val Met Val Leu Leu Phe Ala Val Asp Thr
    290                 295                 300

Gly Leu Tyr Phe Ser Val Lys Thr Asn Ile Arg Ser Ser Thr Arg Asp
305                 310                 315                 320

Trp Lys Asp His Lys Phe Lys Trp Arg Lys Asp Pro Gln Asp Lys
                325                 330                 335
```

<210> SEQ ID NO 10
<211> LENGTH: 1032
<212> TYPE: DNA
<213> ORGANISM: Artificial Sequence
<220> FEATURE:
<223> OTHER INFORMATION: exemplifying sequence encoding 340 a.a. CD64 domain-based construction

<400> SEQUENCE: 10

```
cttggagaca acatgtggtt cttgacaact ctgctccttt gggttccagt tgatgggcaa     60

gtggacacca caaaggcagt gatcactttg cagcctccat gggtcagcgt gttccaagag    120

gaaaccgtaa ccttgcattg tgaggtgctc catctgcctg ggagcagctc tacacagtgg    180

tttctcaatg gcacagccac tcagacctcg acccccagct acagaatcac ctctgccagt    240

gtcaatgaca gtggtgaata caggtgccag agaggtctct cagggcgaag tgaccccata    300

cagctggaaa tccacagagg ctggctacta ctgcaggtct ccagcagagt cttcacggaa    360
```

```
ggagaacctc tggccttgag gtgtcatgcg tggaaggata agctggtgta caatgtgctt    420

tactatcgaa atggcaaagc ctttaagttt ttccactgga attctaacct caccattctg    480

aaaaccaaca taagtcacaa tggcacctac cattgctcag gcatgggaaa gcatcgctac    540

acatcagcag gaatatctgt cactgtgaaa gagctatttc cagctccagt gctgaatgca    600

tctgtgacat ccccactcct ggaggggaat ctggtcaccc tgagctgtga aacaaagttg    660

ctcttgcaga ggcctggttt gcagctttac ttctccttct acatgggcag caagaccctg    720

cgaggcagga acacatcctc tgaataccaa atactaactg ctagaagaga agactctggg    780

ttatactggt gcgaggctgc cacagaggat ggaaatgtcc ttaagcgcag ccctgagttg    840

gagcttcaag tgcttggcct ccagttacca actcctgtct ggtttcatta ccaagtctct    900

ttctgcttgg tgatggtact cctttttgca gtggacacag gactatattt ctctgtgaag    960

acaaacattc gaagctcaac aagagactgg aaggaccata aatttaaatg gagaaaggac   1020

cctcaagaca aa                                                       1032
```

<210> SEQ ID NO 11
<211> LENGTH: 1020
<212> TYPE: DNA
<213> ORGANISM: ARTIFICIAL SEQUENCE
<220> FEATURE:
<223> OTHER INFORMATION: exemplifying sequence encoding 336 a.a. CD64 exon-based construction

<400> SEQUENCE: 11

```
cttggagaca acatgtggtt cttgacaact ctgctccttt gggttccagt tgatgggcaa     60

gtggacacca caaaggcagt gatcactttg cagcctccat gggtcagcgt gttccaagag    120

gaaaccgtaa ccttgcattg tgaggtgctc catctgcctg ggagcagctc tacacagtgg    180

tttctcaatg gcacagccac tcagacctcg acccccagct acagaatcac ctctgccagt    240

gtcaatgaca gtggtgaata caggtgccag agaggtctct cagggcgaag tgaccccata    300

cagctggaaa tccacagagg ctggctacta ctgcaggtct ccagcagagt cttcacggaa    360

ggagaacctc tggccttgag gtgtcatgcg tggaaggata agctggtgta caatgtgctt    420

tactatcgaa atggcaaagc ctttaagttt ttccactgga attctaacct caccattctg    480

aaaaccaaca taagtcacaa tggcacctac cattgctcag gcatgggaaa gcatcgctac    540

acatcagcag gaatatctgt cactgtgaaa gagctatttc cagctccagt gctgaatgca    600

tctgtgacat ccccactcct ggaggggaat ctggtcaccc tgagctgtga aacaaagttg    660

ctcttgcaga ggcctggttt gcagctttac ttctccttct acatgggcag caagaccctg    720

cgaggcagga acacatcctc tgaataccaa atactaactg ctagaagaga agactctggg    780

ttatactggt gcgaggctgc cacagaggat ggaaatgtcc ttaagcgcag ccctgagttg    840

gagcttcaag tgcttggttt gttctttcca cctgggtacc aagtctcttt ctgcttggtg    900

atggtactcc tttttgcagt ggacacagga ctatatttct ctgtgaagac aaacattcga    960

agctcaacaa gagactggaa ggaccataaa tttaaatgga gaaaggaccc tcaagacaaa   1020
```

<210> SEQ ID NO 12
<211> LENGTH: 1005
<212> TYPE: DNA
<213> ORGANISM: ARTIFICIAL SEQUENCE
<220> FEATURE:
<223> OTHER INFORMATION: exemplifying sequence encoding 335 a.a. CD64 exon-based construction

<400> SEQUENCE: 12

```
atgtggttct tgacaactct gctcctttgg gttccagttg atgggcaagt ggacaccaca      60

aaggcagtga tcactttgca gcctccatgg gtcagcgtgt tccaagagga aaccgtaacc     120

ttgcactgtg aggtgctcca tctgcctggg agcagctcta cacagtggtt tctcaatggc     180

acagccactc agacctcgac ccccagctac agaatcacct ctgccagtgt caatgacagt     240

ggtgaataca ggtgccagag aggtctctca gggcgaagtg accccataca gctggaaatc     300

cacagaggct ggctactact gcaggtctcc agcagagtct tcacggaagg agaacctctg     360

gccttgaggt gtcatgcgtg gaaggataag ctggtgtaca atgtgcttta ctatcgaaat     420

ggcaaagcct ttaagttttt ccactggaac tctaacctca ccattctgaa aaccaacata     480

agtcacaatg gcacctacca ttgctcaggc atgggaaagc atcgctacac atcagcagga     540

atatctgtca ctgtgaaaga gctatttcca gctccagtgc tgaatgcatc tgtgacatcc     600

ccactcctgg aggggaatct ggtcaccctg agctgtgaaa caaagttgct cttgcagagg     660

cctggtttgc agctttactt ctccttctac atgggcagca agaccctgcg aggcaggaac     720

acatcctctg aataccaaat actaactgct agaagagaag actctgggtt atactggtgc     780

gaggctgcca cagaggatgg aaatgtcctt aagcgcagcc ctgagttgga gcttcaagtg     840

cttggcttct ttccacctgg gtaccaagtc tctttctgct tggtgatggt actccttttt     900

gcagtggaca caggactata tttctctgtg aagacaaaca ttcgaagctc aacaagagac     960

tggaaggacc ataaatttaa atggagaaag gaccctcaag acaaa                   1005
```

```
<210> SEQ ID NO 13
<211> LENGTH: 153
<212> TYPE: PRT
<213> ORGANISM: Artificial Sequence
<220> FEATURE:
<223> OTHER INFORMATION: 153 a.a. CD28 co-stim + CD3-zeta-ITAM

<400> SEQUENCE: 13

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Val Lys Phe Ser Arg Ser
        35                  40                  45

Ala Asp Ala Pro Ala Tyr Gln Gln Gly Gln Asn Gln Leu Tyr Asn Glu
    50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Arg Arg Lys Asn Pro Gln
                85                  90                  95

Glu Gly Leu Phe Asn Glu Leu Gln Lys Asp Lys Met Ala Glu Ala Phe
            100                 105                 110

Ser Glu Ile Gly Met Lys Gly Glu Arg Arg Arg Gly Lys Gly His Asp
        115                 120                 125

Gly Leu Phe Gln Gly Leu Ser Thr Ala Thr Lys Asp Thr Phe Asp Ala
    130                 135                 140

Leu His Met Gln Ala Leu Pro Pro Arg
145                 150


<210> SEQ ID NO 14
<211> LENGTH: 219
<212> TYPE: PRT
```

```
<213> ORGANISM: Artificial Sequence
<220> FEATURE:
<223> OTHER INFORMATION: 219 a.a. CD28 hinge + CD28 TM + CD28 co-stim +
      CD3-zeta-ITAM

<400> SEQUENCE: 14

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Arg Val Lys Phe Ser
            100                 105                 110

Arg Ser Ala Asp Ala Pro Ala Tyr Gln Gln Gly Gln Asn Gln Leu Tyr
        115                 120                 125

Asn Glu Leu Asn Leu Gly Arg Arg Glu Glu Tyr Asp Val Leu Asp Lys
    130                 135                 140

Arg Arg Gly Arg Asp Pro Glu Met Gly Gly Lys Pro Arg Arg Lys Asn
145                 150                 155                 160

Pro Gln Glu Gly Leu Phe Asn Glu Leu Gln Lys Asp Lys Met Ala Glu
                165                 170                 175

Ala Phe Ser Glu Ile Gly Met Lys Gly Glu Arg Arg Arg Gly Lys Gly
            180                 185                 190

His Asp Gly Leu Phe Gln Gly Leu Ser Thr Ala Thr Lys Asp Thr Phe
        195                 200                 205

Asp Ala Leu His Met Gln Ala Leu Pro Pro Arg
    210                 215


<210> SEQ ID NO 15
<211> LENGTH: 263
<212> TYPE: PRT
<213> ORGANISM: Artificial Sequence
<220> FEATURE:
<223> OTHER INFORMATION: 263 a.a NKG2D TM + 2B4 + CD3-zeta

<400> SEQUENCE: 15

Ser Asn Leu Phe Val Ala Ser Trp Ile Ala Val Met Ile Ile Phe Arg
1               5                   10                  15

Ile Gly Met Ala Val Ala Ile Phe Cys Cys Phe Phe Phe Pro Ser Trp
            20                  25                  30

Arg Arg Lys Arg Lys Glu Lys Gln Ser Glu Thr Ser Pro Lys Glu Phe
        35                  40                  45

Leu Thr Ile Tyr Glu Asp Val Lys Asp Leu Lys Thr Arg Arg Asn His
    50                  55                  60

Glu Gln Glu Gln Thr Phe Pro Gly Gly Gly Ser Thr Ile Tyr Ser Met
65                  70                  75                  80

Ile Gln Ser Gln Ser Ser Ala Pro Thr Ser Gln Glu Pro Ala Tyr Thr
                85                  90                  95

Leu Tyr Ser Leu Ile Gln Pro Ser Arg Lys Ser Gly Ser Arg Lys Arg
            100                 105                 110
```

```
Asn His Ser Pro Ser Phe Asn Ser Thr Ile Tyr Glu Val Ile Gly Lys
        115                 120                 125

Ser Gln Pro Lys Ala Gln Asn Pro Ala Arg Leu Ser Arg Lys Glu Leu
    130                 135                 140

Glu Asn Phe Asp Val Tyr Ser Arg Val Lys Phe Ser Arg Ser Ala Asp
145                 150                 155                 160

Ala Pro Ala Tyr Lys Gln Gly Gln Asn Gln Leu Tyr Asn Glu Leu Asn
                165                 170                 175

Leu Gly Arg Arg Glu Glu Tyr Asp Val Leu Asp Lys Arg Arg Gly Arg
            180                 185                 190

Asp Pro Glu Met Gly Gly Lys Pro Arg Arg Lys Asn Pro Gln Glu Gly
        195                 200                 205

Leu Tyr Asn Glu Leu Gln Lys Asp Lys Met Ala Glu Ala Tyr Ser Glu
    210                 215                 220

Ile Gly Met Lys Gly Glu Arg Arg Arg Gly Lys Gly His Asp Gly Leu
225                 230                 235                 240

Tyr Gln Gly Leu Ser Thr Ala Thr Lys Asp Thr Tyr Asp Ala Leu His
                245                 250                 255

Met Gln Ala Leu Pro Pro Arg
            260


<210> SEQ ID NO 16
<211> LENGTH: 308
<212> TYPE: PRT
<213> ORGANISM: Artificial Sequence
<220> FEATURE:
<223> OTHER INFORMATION: 308 a.a CD8 hinge + NKG2D TM + 2B4 + CD3-zeta

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ser Asn Leu
        35                  40                  45

Phe Val Ala Ser Trp Ile Ala Val Met Ile Ile Phe Arg Ile Gly Met
    50                  55                  60

Ala Val Ala Ile Phe Cys Cys Phe Phe Phe Pro Ser Trp Arg Arg Lys
65                  70                  75                  80

Arg Lys Glu Lys Gln Ser Glu Thr Ser Pro Lys Glu Phe Leu Thr Ile
                85                  90                  95

Tyr Glu Asp Val Lys Asp Leu Lys Thr Arg Arg Asn His Glu Gln Glu
            100                 105                 110

Gln Thr Phe Pro Gly Gly Gly Ser Thr Ile Tyr Ser Met Ile Gln Ser
        115                 120                 125

Gln Ser Ser Ala Pro Thr Ser Gln Glu Pro Ala Tyr Thr Leu Tyr Ser
    130                 135                 140

Leu Ile Gln Pro Ser Arg Lys Ser Gly Ser Arg Lys Arg Asn His Ser
145                 150                 155                 160

Pro Ser Phe Asn Ser Thr Ile Tyr Glu Val Ile Gly Lys Ser Gln Pro
                165                 170                 175

Lys Ala Gln Asn Pro Ala Arg Leu Ser Arg Lys Glu Leu Glu Asn Phe
            180                 185                 190

Asp Val Tyr Ser Arg Val Lys Phe Ser Arg Ser Ala Asp Ala Pro Ala
        195                 200                 205
```

```
Tyr Lys Gln Gly Gln Asn Gln Leu Tyr Asn Glu Leu Asn Leu Gly Arg
    210                 215                 220

Arg Glu Glu Tyr Asp Val Leu Asp Lys Arg Arg Gly Arg Asp Pro Glu
225                 230                 235                 240

Met Gly Gly Lys Pro Arg Arg Lys Asn Pro Gln Glu Gly Leu Tyr Asn
                245                 250                 255

Glu Leu Gln Lys Asp Lys Met Ala Glu Ala Tyr Ser Glu Ile Gly Met
            260                 265                 270

Lys Gly Glu Arg Arg Arg Gly Lys Gly His Asp Gly Leu Tyr Gln Gly
        275                 280                 285

Leu Ser Thr Ala Thr Lys Asp Thr Tyr Asp Ala Leu His Met Gln Ala
    290                 295                 300

Leu Pro Pro Arg
305


<210> SEQ ID NO 17
<211> LENGTH: 379
<212> TYPE: PRT
<213> ORGANISM: Artificial Sequence
<220> FEATURE:
<223> OTHER INFORMATION: construct mimicking trans-presentation of IL15
      (design 3)

<400> SEQUENCE: 17

Met Asp Trp Thr Trp Ile Leu Phe Leu Val Ala Ala Ala Thr Arg Val
1               5                   10                  15

His Ser Gly Ile His Val Phe Ile Leu Gly Cys Phe Ser Ala Gly Leu
            20                  25                  30

Pro Lys Thr Glu Ala Asn Trp Val Asn Val Ile Ser Asp Leu Lys Lys
        35                  40                  45

Ile Glu Asp Leu Ile Gln Ser Met His Ile Asp Ala Thr Leu Tyr Thr
    50                  55                  60

Glu Ser Asp Val His Pro Ser Cys Lys Val Thr Ala Met Lys Cys Phe
65                  70                  75                  80

Leu Leu Glu Leu Gln Val Ile Ser Leu Glu Ser Gly Asp Ala Ser Ile
                85                  90                  95

His Asp Thr Val Glu Asn Leu Ile Ile Leu Ala Asn Asn Ser Leu Ser
            100                 105                 110

Ser Asn Gly Asn Val Thr Glu Ser Gly Cys Lys Glu Cys Glu Glu Leu
        115                 120                 125

Glu Glu Lys Asn Ile Lys Glu Phe Leu Gln Ser Phe Val His Ile Val
    130                 135                 140

Gln Met Phe Ile Asn Thr Ser Ser Gly Gly Gly Ser Gly Gly Gly Gly
145                 150                 155                 160

Ser Gly Gly Gly Gly Ser Gly Gly Gly Gly Ser Gly Gly Gly Ser Leu
                165                 170                 175

Gln Ile Thr Cys Pro Pro Pro Met Ser Val Glu His Ala Asp Ile Trp
            180                 185                 190

Val Lys Ser Tyr Ser Leu Tyr Ser Arg Glu Arg Tyr Ile Cys Asn Ser
        195                 200                 205

Gly Phe Lys Arg Lys Ala Gly Thr Ser Ser Leu Thr Glu Cys Val Leu
    210                 215                 220

Asn Lys Ala Thr Asn Val Ala His Trp Thr Thr Pro Ser Leu Lys Cys
225                 230                 235                 240

Ile Arg Asp Pro Ala Leu Val His Gln Arg Pro Ala Pro Pro Ser Thr
```

```
                245                 250                 255

Val Thr Thr Ala Gly Val Thr Pro Gln Pro Glu Ser Leu Ser Pro Ser
            260                 265                 270

Gly Lys Glu Pro Ala Ala Ser Ser Pro Ser Ser Asn Asn Thr Ala Ala
        275                 280                 285

Thr Thr Ala Ala Ile Val Pro Gly Ser Gln Leu Met Pro Ser Lys Ser
    290                 295                 300

Pro Ser Thr Gly Thr Thr Glu Ile Ser Ser His Glu Ser Ser His Gly
305                 310                 315                 320

Thr Pro Ser Gln Thr Thr Ala Lys Asn Trp Glu Leu Thr Ala Ser Ala
                325                 330                 335

Ser His Gln Pro Pro Gly Val Tyr Pro Gln Gly His Ser Asp Thr Thr
            340                 345                 350

Val Ala Ile Ser Thr Ser Thr Val Leu Leu Cys Gly Leu Ser Ala Val
        355                 360                 365

Ser Leu Leu Ala Cys Tyr Leu Lys Ser Arg Gln
    370                 375
```

```
<210> SEQ ID NO 18
<211> LENGTH: 1140
<212> TYPE: DNA
<213> ORGANISM: Artificial Sequence
<220> FEATURE:
<223> OTHER INFORMATION: an exemplary nucleic acid sequence encoding
      construct mimicking trans-presentation of IL15 (design 3)

<400> SEQUENCE: 18

atggactgga cctggattct gttcctggtc gcggctgcaa cgcgagtcca tagcggtatc     60

catgtttta ttcttgggtg tttttctgct gggctgccta agaccgaggc caactgggta     120

aatgtcatca gtgacctcaa gaaaatagaa gaccttatac aaagcatgca cattgatgct    180

actctctaca ctgagtcaga tgtacatccc tcatgcaaag tgacggccat gaaatgtttc    240

ctcctcgaac ttcaagtcat atctctggaa agtggcgacg cgtccatcca cgacacggtc    300

gaaaacctga taatactcgc taataatagt ctctcttcaa atggtaacgt aaccgagtca    360

ggttgcaaag agtgcgaaga gttggaagaa aaaaacataa aggagttcct gcaaagtttc    420

gtgcacattg tgcagatgtt cattaatacc tctagcggcg gaggatcagg tggcggtgga    480

agcggaggtg gaggctccgg tggaggaggt agtggcggag gttctcttca aataacttgt    540

cctccaccga tgtccgtaga acatgcggat atttgggtaa aatcctatag cttgtacagc    600

cgagagcggt atatctgcaa cagcggcttc aagcggaagg ccggcacaag cagcctgacc    660

gagtgcgtgc tgaacaaggc caccaacgtg gcccactgga ccacccctag cctgaagtgc    720

atcagagatc ccgccctggt gcatcagcgg cctgcccctc caagcacagt gacaacagct    780

ggcgtgaccc cccagcctga gagcctgagc ccttctggaa aagagcctgc cgccagcagc    840

cccagcagca acaatactgc cgccaccaca gccgccatcg tgcctggatc tcagctgatg    900

cccagcaaga gccctagcac cggcaccacc gagatcagca gccacgagtc tagccacggc    960

accccatctc agaccaccgc caagaactgg gagctgacag ccagcgcctc tcaccagcct   1020

ccaggcgtgt accctcaggg ccacagcgat accacagtgg ccatcagcac ctccaccgtg   1080

ctgctgtgtg gactgagcgc cgtgtcactg ctggcctgct acctgaagtc cagacagtga   1140

<210> SEQ ID NO 19
<211> LENGTH: 242
<212> TYPE: PRT
```

<213> ORGANISM: Artificial Sequence
<220> FEATURE:
<223> OTHER INFORMATION: fused IL15/mb-Sushi construct (design 4)

<400> SEQUENCE: 19

```
Met Asp Trp Thr Trp Ile Leu Phe Leu Val Ala Ala Ala Thr Arg Val
1               5                   10                  15

His Ser Gly Ile His Val Phe Ile Leu Gly Cys Phe Ser Ala Gly Leu
            20                  25                  30

Pro Lys Thr Glu Ala Asn Trp Val Asn Val Ile Ser Asp Leu Lys Lys
        35                  40                  45

Ile Glu Asp Leu Ile Gln Ser Met His Ile Asp Ala Thr Leu Tyr Thr
    50                  55                  60

Glu Ser Asp Val His Pro Ser Cys Lys Val Thr Ala Met Lys Cys Phe
65                  70                  75                  80

Leu Leu Glu Leu Gln Val Ile Ser Leu Glu Ser Gly Asp Ala Ser Ile
                85                  90                  95

His Asp Thr Val Glu Asn Leu Ile Ile Leu Ala Asn Asn Ser Leu Ser
            100                 105                 110

Ser Asn Gly Asn Val Thr Glu Ser Gly Cys Lys Glu Cys Glu Glu Leu
        115                 120                 125

Glu Glu Lys Asn Ile Lys Glu Phe Leu Gln Ser Phe Val His Ile Val
    130                 135                 140

Gln Met Phe Ile Asn Thr Ser Ser Gly Gly Gly Ser Gly Gly Gly Gly
145                 150                 155                 160

Ser Gly Gly Gly Gly Ser Gly Gly Gly Gly Ser Gly Gly Gly Ser Leu
                165                 170                 175

Gln Ile Thr Cys Pro Pro Pro Met Ser Val Glu His Ala Asp Ile Trp
            180                 185                 190

Val Lys Ser Tyr Ser Leu Tyr Ser Arg Glu Arg Tyr Ile Cys Asn Ser
        195                 200                 205

Gly Phe Lys Arg Lys Ala Gly Thr Ser Ser Leu Thr Glu Cys Val Leu
    210                 215                 220

Asn Lys Ala Thr Asn Val Ala His Trp Thr Thr Pro Ser Leu Lys Cys
225                 230                 235                 240

Ile Arg
```

<210> SEQ ID NO 20
<211> LENGTH: 726
<212> TYPE: DNA
<213> ORGANISM: Artificial Sequence
<220> FEATURE:
<223> OTHER INFORMATION: an exemplary nucleic acid sequence encoding fused IL15/mb-Sushi construct (design 4)

<400> SEQUENCE: 20

```
atggactgga cctggattct gttcctggtc gcggctgcaa cgcgagtcca tagcggtatc     60

catgttttta ttcttgggtg tttttctgct gggctgccta agaccgaggc caactgggta    120

aatgtcatca gtgacctcaa gaaaatagaa gaccttatac aaagcatgca cattgatgct    180

actctctaca ctgagtcaga tgtacatccc tcatgcaaag tgacggccat gaaatgtttc    240

ctcctcgaac ttcaagtcat atctctggaa agtggcgacg cgtccatcca cgacacggtc    300

gaaaacctga taatactcgc taataatagt ctctcttcaa atggtaacgt aaccgagtca    360

ggttgcaaag agtgcgaaga gttggaagaa aaaaacataa aggagttcct gcaaagtttc    420

gtgcacattg tgcagatgtt cattaatacc tctagcggcg gaggatcagg tggcggtgga    480
```

```
agcggaggtg gaggctccgg tggaggaggt agtggcggag gttctcttca aataacttgt    540

cctccaccga tgtccgtaga acatgcggat atttgggtaa aatcctatag cttgtacagc    600

cgagagcggt atatctgcaa cagcggcttc aagcggaagg ccggcacaag cagcctgacc    660

gagtgcgtgc tgaacaaggc caccaacgtg gcccactgga ccacccctag cctgaagtgc    720

atcaga                                                               726


<210> SEQ ID NO 21
<211> LENGTH: 375
<212> TYPE: PRT
<213> ORGANISM: Artificial Sequence
<220> FEATURE:
<223> OTHER INFORMATION: protein construct further modified from SEQ ID
      NO. 17

<400> SEQUENCE: 21

Met Asp Trp Thr Trp Ile Leu Phe Leu Val Ala Ala Ala Thr Arg Val
1               5                   10                  15

His Ser Gly Ile His Val Phe Ile Leu Gly Cys Phe Ser Ala Gly Leu
            20                  25                  30

Pro Lys Thr Glu Ala Asn Trp Val Asn Val Ile Ser Asp Leu Lys Lys
        35                  40                  45

Ile Glu Asp Leu Ile Gln Ser Met His Ile Asp Ala Thr Leu Tyr Thr
    50                  55                  60

Glu Ser Asp Val His Pro Ser Cys Lys Val Thr Ala Met Lys Cys Phe
65                  70                  75                  80

Leu Leu Glu Leu Gln Val Ile Ser Leu Glu Ser Gly Asp Ala Ser Ile
                85                  90                  95

His Asp Thr Val Glu Asn Leu Ile Ile Leu Ala Asn Asn Ser Leu Ser
            100                 105                 110

Ser Asn Gly Asn Val Thr Glu Ser Gly Cys Lys Glu Cys Glu Glu Leu
        115                 120                 125

Glu Glu Lys Asn Ile Lys Glu Phe Leu Gln Ser Phe Val His Ile Val
    130                 135                 140

Gln Met Phe Ile Asn Thr Ser Ser Gly Gly Gly Ser Gly Gly Gly Gly
145                 150                 155                 160

Ser Gly Gly Gly Gly Ser Gly Gly Gly Gly Ser Gly Gly Gly Ser Leu
                165                 170                 175

Gln Ile Thr Cys Pro Pro Pro Met Ser Val Glu His Ala Asp Ile Trp
            180                 185                 190

Val Lys Ser Tyr Ser Leu Tyr Ser Arg Glu Arg Tyr Ile Cys Asn Ser
        195                 200                 205

Gly Phe Lys Arg Lys Ala Gly Thr Ser Ser Leu Thr Glu Cys Val Leu
    210                 215                 220

Asn Lys Ala Thr Asn Val Ala His Trp Thr Thr Pro Ser Leu Lys Cys
225                 230                 235                 240

Ile Arg Asp Pro Ala Leu Val His Gln Arg Pro Ala Pro Pro Ser Thr
                245                 250                 255

Val Thr Thr Ala Gly Val Thr Pro Gln Pro Glu Ser Leu Ser Pro Ser
            260                 265                 270

Gly Lys Glu Pro Ala Ala Ser Ser Pro Ser Ser Asn Asn Thr Ala Ala
        275                 280                 285

Thr Thr Ala Ala Ile Val Pro Gly Ser Gln Leu Met Pro Ser Lys Ser
    290                 295                 300
```

-continued

```
Pro Ser Thr Gly Thr Thr Glu Ile Ser Ser His Glu Ser Ser His Gly
305                 310                 315                 320

Thr Pro Ser Gln Thr Thr Ala Lys Asn Trp Glu Leu Thr Ala Ser Ala
                325                 330                 335

Ser His Gln Pro Pro Gly Val Tyr Pro Gln Gly His Ser Asp Thr Thr
            340                 345                 350

Val Ala Ile Ser Thr Ser Thr Val Leu Leu Cys Gly Leu Ser Ala Val
        355                 360                 365

Ser Leu Leu Ala Cys Tyr Leu
    370                 375
```